US011008630B2

(12) United States Patent
Kelleher et al.

(10) Patent No.: US 11,008,630 B2
(45) Date of Patent: May 18, 2021

(54) METHODS FOR DISCRIMINATING BETWEEN HIV-1 AND LENTIVIRAL VECTORS

(71) Applicants: CSL Behring Gene Therapy, Inc., Pasadena, CA (US); CSL Gene Therapy Pty Ltd., Parkville (AU); St. Vincent's Hospital Sydney Limited, Darlinghurst (AU); Newsouth Innovations PTY Limited, Sydney (AU)

(72) Inventors: Anthony Dominic Kelleher, Bangor (AU); Kazuo Suzuki, Sydney (AU); Geoffrey Phillip Symonds, Rose Bay (AU)

(73) Assignees: CSL Behring Gene Therapy, Inc., Pasadena, CA (US); CSL Gene Therapy Pty Ltd., Parkville (AU); St. Vincent's Hospital Sydney Limited, Darlinghurst (AU); Newsouth Innovations Pty Limited, Sydney (AU)

( * ) Notice: Subject to any disclaimer, the term of this patent is extended or adjusted under 35 U.S.C. 154(b) by 0 days.

(21) Appl. No.: 16/267,404

(22) Filed: Feb. 5, 2019

(65) Prior Publication Data

US 2019/0153551 A1 May 23, 2019

Related U.S. Application Data

(63) Continuation of application No. 15/810,254, filed on Nov. 13, 2017, now Pat. No. 10,240,214, which is a
(Continued)

(51) Int. Cl.
*C12Q 1/68* (2018.01)
*C12Q 1/70* (2006.01)
*C12N 7/00* (2006.01)

(52) U.S. Cl.
CPC ............... *C12Q 1/703* (2013.01); *C12N 7/00* (2013.01); *C12N 2740/16021* (2013.01); *C12N 2740/16043* (2013.01)

(58) Field of Classification Search
None
See application file for complete search history.

(56) References Cited

U.S. PATENT DOCUMENTS

2010/0113566 A1* 5/2010 Chono ............... A61K 31/7088
514/44 R
2016/0076055 A1 3/2016 Allen et al.

FOREIGN PATENT DOCUMENTS

WO 2011008348 A2 1/2011
WO 2011011584 A1 1/2011

OTHER PUBLICATIONS

Krebs et al., Lentiviral LTR-directed expression, sequence variation, and disease pathogenesis, Los Alamos National Laboratory HIV Sequence Compendium, Dec. 2002.*

(Continued)

*Primary Examiner* — Aaron A Priest
(74) *Attorney, Agent, or Firm* — Charney IP Law LLC; Thomas M. Finetti

(57) ABSTRACT

The present disclosure provides compositions (i.e., amplification primers and probes), methods, and kits that are particularly useful for detecting and/or quantifying nucleic acids present in a sample, such as those derived from HIV or a lentiviral vector.

9 Claims, 43 Drawing Sheets
Specification includes a Sequence Listing.

Related U.S. Application Data continuation-in-part of application No. PCT/US2016/032767, filed on May 16, 2016.

(60) Provisional application No. 62/163,327, filed on May 18, 2015.

(56) References Cited

OTHER PUBLICATIONS

Burke et al., CCRS as a Natural and Modulated Target for Inhibition of HIV, Viruses. Jan. 2014; 6(1): 54-68. Published online Dec. 30, 2013.*

Sanchez et al., Accumulation of defective viral genomes in peripheral blood mononuclear cells of human immunodeficiency virus type 1-infected individuals, J Virol. Mar. 1997;71(3):2233-40.*

International Search Report and Written Opinion, dated Aug. 1, 2016.

Wolstein et al., "Preclinical safety and efficacy of an anti-HIV-1 lentiviral vector containing a short hairpin RNA to CCR5 and the C46 fusion inhibitor", Molecular Therapy—Methods & Clinical Development, vol. 1, Feb. 12, 2014, p. 11.

Bryan Burke et al: "CCR5 as a Natural and Modulated Target for Inhibition of HIV", Viruses, vol. 6, No. 1, Dec. 30, 2013 (Dec. 30, 2013), CH, pp. 54-68, XP055287500, ISSN: 1999-4915, DOI: 10.3390/v6010054.

Bryan P Burke et al: "Engineering Cellular Resistance to HIV-1 Infection In Vivo Using a Dual Therapeutic Lentiviral Vector", Molecular Therapy-Nucleic Acids, vol. 4, No. 4, Apr. 14, 2015 (Apr. 14, 2015), p. e236.

Database EMBL [online] Jun. 22, 2005 (Jun. 22, 2005), "Sequence 20 from Patent WO2005051986.", XP002759935, retrieved from EBI accession No. EM_PAT:CS108612 Database accession No. CS108612.

Database Geneseq [online] Apr. 1, 1997 (Apr. 1, 1997), "HIV TAR fragment detection probe 1, (TAR loop probe).", XP002759931, retrieved from EBI accession No. GSN:AAT58845 Database accession No. AAT58845.

Database Geneseq [online] Mar. 25, 2003 (Mar. 25, 2003), "Human immunodeficiency virus region 1 probe," XP002759932, retrieved from EBI accession No. GSN:AAT15554 Database accession No. AAT15554.

Database Geneseq [online] Mar. 25, 2003 (Mar. 25, 2003), "Viral DNA R2 primer.", XP002759930, retrieved from EBI accession No. GSN:AAQ31821 Database accession No. AAQ31821.

Database Geneseq [online] Dec. 29, 2005 (Dec. 29, 2005), "HIV-1 5' LTR TATA box/TAR sequence, from AF102206-G.", XP002759934, retrieved from EBI accession No. GSN:AED60207 Database accession No. AED60207.

Database Geneseq [online] Dec. 6, 2012 (Dec. 6, 2012), "Human immunodeficiency virus 1 U3 region coding sequence, SEQ ID 21.", XP002759933, retrieved from EBI accession No. GSN:BAD81538 Database accession No. BAD81538.

Borislav Savkovic, et. al., "A Quantitative Comparison of Anti-HIV Gene Therapy Delivered to Hematopoietic Stem Cells versus CD4+ T Cells," PLOS Computational Biology, Jun. 2014, vol. 10, Issue 6, e1003681.

* cited by examiner

FIG. 1D
B
Junction probe
cATTTcATcAcATGGCCCGAGAGCTGCATCCGGA
cATTTcATcAcATGGCCCGAGAGCTGCATCCGGAGTACTTCAAGAATGCTGAC
Cal-1 LV vector was generated by removal of 132 bases from HXB2 (HIV-1 wide type)
Cal-1 U3 region
Cal-1 R start region
U3 region HXB2a

FIG. 16A

HIVγ 1 DNA analysis (A)

HIV DNA Copies / 1,000 Cells

| Animal ID | Spleen |
|---|---|
| Ctrl 01 | 10.53 |
| Ctrl 07 | 33.79 |
| Ctrl 10 | 10.29 |
| Ctrl 11 | 13.00 |
| Ctrl 21 | 21.18 |
| Ctrl 27 | 3.97 |
| Ctrl 28 | 6.23 |
| CAL-1 04 | 0.15 |
| CAL-1 06 | 0.00 |
| CAL-1 08 | 0.00 |
| CAL-1 12 | 0.00 |
| CAL-1 16 | 0.62 |
| CAL-1 17 | 0.00 |

FIG. 16B

HIVγ 1 DNA analysis (B)

HIV-1 copy per 10(3) Actin copy

| Spleen |
|---|
| 2.41 |
| 12.84 |
| 1.74 |
| 2.42 |
| 6.47 |
| 0.53 |
| 2.07 |
| 0.00 |
| 0.00 |
| 0.02 |
| 0.00 |
| 0.16 |
| 0.00 |

Calγ 1 DNA analysis (A)

Vector Copy Number Per Cell

| Animal ID | Spleen |
|---|---|
| Ctrl 01 | 0.00 |
| Ctrl 07 | 0.00 |
| Ctrl 10 | 0.00 |
| Ctrl 11 | 0.00 |
| Ctrl 21 | 0.00 |
| Ctrl 27 | 0.00 |
| Ctrl 28 | 0.00 |
| CAL-1 04 | 0.81 |
| CAL-1 06 | 1.50 |
| CAL-1 08 | 1.11 |
| CAL-1 12 | 1.09 |
| CAL-1 16 | 1.62 |
| CAL-1 17 | 1.24 |

FIG. 16C

Calγ 1 DNA analysis (B)

Cal-1 copy per 10(3) Actin copy

| Spleen |
|---|
| 0.000 |
| 0.000 |
| 0.000 |
| 0.000 |
| 0.000 |
| 0.000 |
| 0.000 |
| 38.631 |
| 54.656 |
| 50.488 |
| 55.066 |
| 59.012 |
| 52.007 |

FIG. 16D 2016-0514 HIV CAL ACTIN assay for BLT

| Pos | Name | Cp | HIV-1 Concentration | Actin | HIV-1 copy per 10(3) Actin copy | Cp | Cal-1 Concentration | Actin | Cal-1 copy per 10(3) Actin copy |
|---|---|---|---|---|---|---|---|---|---|
| A2 | NC | | 0 | | | | 0 | | |
| B2 | HIV standard | 38.02 | 4 | | | 37.14 | 2 | | |
| C2 | HIV standard | 35.57 | 40 | | | 36.78 | 20 | | |
| D2 | HIV standard | 31.88 | 400 | | | 33.67 | 200 | | |
| E2 | HIV standard | 28.72 | 4000 | | | 30.09 | 2000 | | |
| F2 | HIV standard | 25.25 | 40000 | | | 26.74 | 20000 | | |
| G2 | HIV standard | 21.88 | 400000 | | | 23.5 | 200000 | | |
| H2 | HIV standard | 18.26 | 4000000 | | | 20.31 | 2000000 | | |
| | slope= -3.695 r=1.865 | | | | | | | | |
| A3 | Ctrl 01 | 27.80 | 6540.00 | 2708170 | 2.415 | | | 2708170 | 0.000 |
| B3 | Ctrl 07 | 26.99 | 11400.00 | 887742.6 | 12.842 | | | 887742.6 | 0.000 |
| C3 | Ctrl 10 | 28.59 | 3800.00 | 2178513 | 1.744 | | | 2178513 | 0.000 |
| D3 | Ctrl 11 | 27.91 | 6080.00 | 2512961 | 2.419 | | | 2512961 | 0.000 |
| E3 | Ctrl 21 | 26.55 | 15500.00 | 2396134 | 6.469 | | | 2396134 | 0.000 |
| F3 | Ctrl 27 | 30.57 | 965.00 | 1837894 | 0.525 | | | 1837894 | 0.000 |
| G3 | Ctrl 28 | 27.65 | 7270.00 | 3504253 | 2.075 | | | 3504253 | 0.000 |
| A4 | CAL-1 04 | | | 1837894 | 0.000 | 25.1 | 71000 | 1837894 | 38.631 |
| B4 | CAL-1 06 | 41.70 | 0.44 | 2049174 | 0.000 | 24.51 | 112000 | 2049174 | 54.656 |
| C4 | CAL-1 08 | 35.00 | 45.10 | 1980661 | 0.023 | 24.65 | 100000 | 1980661 | 50.488 |
| D4 | CAL-1 12 | | | 3650190 | 0.000 | 23.74 | 201000 | 3650190 | 55.066 |
| E4 | CAL-1 16 | 31.35 | 560.00 | 3456915 | 0.162 | 23.72 | 204000 | 3456915 | 59.012 |
| F4 | CAL-1 17 | | | 2653475 | 0.000 | 24.23 | 138000 | 2653475 | 52.007 |
| H3 | NO.1 control <MOLT4 w Cal1> with HIV day 14 | 24.18 | 80200 | 44300 | 1,810 | 27.02 | 16300 | 44300 | 368 |
| G4 | NO.2 control <MOLT4 (w/o Cal1)> with HIV day14 | | | 119000 | 0 | | 0 | 119000 | 0 |
| H4 | NO.3control <80% MOLT4 20% MOLT4-Cal1> with HIV day 14 | 27.14 | 10300 | 77100 | 134 | 31.52 | 511 | 77100 | 7 |

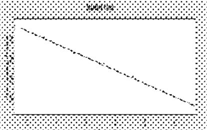
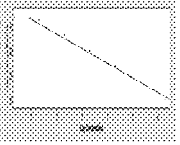

FIG. 17

SEQUENCE LISTING

```
<160> NUMBER OF SEQ ID NOS: 17

<210> SEQ ID NO 1
<211> LENGTH: 24
<212> TYPE: DNA
<213> ORGANISM: Artificial Sequence
<220> FEATURE:
<223> OTHER INFORMATION: Synthetic: sequence within the U3 region that
      the NuAf primer hybridizes to

<400> SEQUENCE: 1
```

ggtttcttct gttctatagg aact 24

<210> SEQ ID NO 2
<211> LENGTH: 25
<212> TYPE: DNA
<213> ORGANISM: Artificial Sequence
<220> FEATURE:
<223> OTHER INFORMATION: Synthetic: NuAf primer

<400> SEQUENCE: 2
ccaaagaaga caagatatcc ttgac 25

<210> SEQ ID NO 3
<211> LENGTH: 22
<212> TYPE: DNA
<213> ORGANISM: Artificial Sequence
<220> FEATURE:
<223> OTHER INFORMATION: Synthetic: sequence within the U3 region that the TATA primer hybridizes to

<400> SEQUENCE: 3
gacgaatata cgtcgtagac tc 22

<210> SEQ ID NO 4
<211> LENGTH: 22
<212> TYPE: DNA
<213> ORGANISM: Artificial Sequence
<220> FEATURE:
<223> OTHER INFORMATION: Synthetic: TATA primer

<400> SEQUENCE: 4
ctcagatgct gcatataagc ag 22

<210> SEQ ID NO 5
<211> LENGTH: 18
<212> TYPE: DNA
<213> ORGANISM: Artificial Sequence
<220> FEATURE:
<223> OTHER INFORMATION: Synthetic: sequence within the R region that the LTR-rev primer hybridizes to

<400> SEQUENCE: 5
ccactgctta agcctcaa 18

<210> SEQ ID NO 6
<211> LENGTH: 18
<212> TYPE: DNA
<213> ORGANISM: Artificial Sequence
<220> FEATURE:
<223> OTHER INFORMATION: Synthetic: LTR-rev primer

<400> SEQUENCE: 6
ttgaggctta agcagtgg 18

<210> SEQ ID NO 7
<211> LENGTH: 29
<212> TYPE: DNA
<213> ORGANISM: Artificial Sequence
<220> FEATURE:
<223> OTHER INFORMATION: Synthetic: sequence within the 3'LTR that the TAR-probe hybridizes

<400> SEQUENCE: 7
aatctggtct agactcggac cctcgagag 29

-continued

<210> SEQ ID NO 8
<211> LENGTH: 29
<212> TYPE: DNA
<213> ORGANISM: Artificial Sequence
<220> FEATURE:
<223> OTHER INFORMATION: Synthetic: TAR-probe

<400> SEQUENCE: 8
ttagaccaga tctgagcctg ggagctctc 29

<210> SEQ ID NO 9
<211> LENGTH: 25
<212> TYPE: DNA
<213> ORGANISM: Artificial Sequence
<220> FEATURE:
<223> OTHER INFORMATION: Synthetic: sequence within the 3'LTR that the TATA-probe hybridizes to

<400> SEQUENCE: 9
gccctcagat cctgcatata agcag 25

<210> SEQ ID NO 10
<211> LENGTH: 25
<212> TYPE: DNA
<213> ORGANISM: Artificial Sequence
<220> FEATURE:
<223> OTHER INFORMATION: Synthetic: TATA-probe

<400> SEQUENCE: 10
ctgcttatat gcaggatctg agggc 25

<210> SEQ ID NO 11
<211> LENGTH: 5
<212> TYPE: DNA
<213> ORGANISM: Artificial Sequence
<220> FEATURE:
<223> OTHER INFORMATION: Synthetic: TATA box sequence

<400> SEQUENCE: 11 tataa 5

<210> SEQ ID NO 12
<211> LENGTH: 21
<212> TYPE: DNA
<213> ORGANISM: Artificial Sequence
<220> FEATURE:
<223> OTHER INFORMATION: Synthetic: Sequence within U3 region in which the junction probe hybridizes

<400> SEQUENCE: 12
cgacgtaggc ctgacatgac c 21

<210> SEQ ID NO 13
<211> LENGTH: 6
<212> TYPE: DNA
<213> ORGANISM: Artificial Sequence
<220> FEATURE:
<223> OTHER INFORMATION: Synthetic: Sequence within R region in which the junction probe hybridizes

<400> SEQUENCE: 13 cagaga 6

<210> SEQ ID NO 14
<211> LENGTH: 27
<212> TYPE: DNA
<213> ORGANISM: Artificial Sequence -continued

```
<220> FEATURE:
<223> OTHER INFORMATION: Synthetic: Junction probe sequence

<400> SEQUENCE: 14

gctgcatccg gactgtactg ggtctct                                          27


<210> SEQ ID NO 15
<211> LENGTH: 322
<212> TYPE: DNA
<213> ORGANISM: Artificial Sequence
<220> FEATURE:
<223> OTHER INFORMATION: Synthetic: U3 sequence of Cal-1

<400> SEQUENCE: 15

tggaagggct aattcactcc caacgaagac aagatatcct tgatctgtgg atctaccaca      60

cacaaggcta cttccctgat tggcagaact acacaccagg gccagggatc agatatccac     120

tgacctttgg atggtgctac aagctagtac cagttgagca agagaaggta gaagaagcca     180

atgaaggaga gaacacccgc ttgttacacc ctgtgagcct gcatgggatg gatgacccgg     240

agagagaagt attagagtgg aggtttgaca gccgcctagc atttcatcac atggcccgag     300

agctgcatcc ggactgtact gg                                              322


<210> SEQ ID NO 16
<211> LENGTH: 454
<212> TYPE: DNA
<213> ORGANISM: HIV-1
<220> FEATURE:
<221> NAME/KEY: misc_feature
<223> OTHER INFORMATION: Wildtype U3 sequence

<400> SEQUENCE: 16

tggaagggct aattcactcc caacgaagac aagatatcct tgatctgtgg atctaccaca      60

cacaaggcta cttccctgat tagcagaact acacaccagg gccagggatc agatatccac     120

tgacctttgg atggtgctac aagctagtac cagttgagcc agagaagtta gaagaagcca     180

acaaaggaga gaacaccagc ttgttacacc ctgtgagcct gcatggaatg gatgacccgg     240

agagagaagt gttagagtgg aggtttgaca gccgcctagc atttcatcac atggcccgag     300

agctgcatcc ggagtacttc aagaatgctg acatcgagct tgctacaagg gactttccgc     360

tggggacttt ccagggaggc gtggcctggg cgggactggg gagtggcgag ccctcagatc     420

ctgcatataa gcagctgctt tttgcctgta ctgg                                 454


<210> SEQ ID NO 17
<211> LENGTH: 96
<212> TYPE: DNA
<213> ORGANISM: Artificial Sequence
<220> FEATURE:
<223> OTHER INFORMATION: Synthetic: R region of Cal-1

<400> SEQUENCE: 17

gtctctctgg ttagaccaga tctgagcctg ggagctctct ggctaactag ggaacccact      60

gcttaagcct caataaagct tgccttgagt gcttca                                96
```

METHODS FOR DISCRIMINATING BETWEEN HIV-1 AND LENTIVIRAL VECTORS

CROSS-REFERENCE TO RELATED APPLICATIONS

This application is a continuation of U.S. patent application Ser. No. 15/810,254 filed on Nov. 13, 2017, which is a continuation-in-part of International Application No. PCT/US2016/032767, filed May 16, 2016, and which claims the benefit of the filing date of U.S. Provisional Patent Application No. 62/163,327 filed May 18, 2015, the disclosures of which are hereby incorporated by reference herein in their entireties.

FIELD OF DISCLOSURE

This disclosure generally relates to the fields of molecular biology and virology. In particular, the disclosure relates to methods for discriminating between HIV-1 and lentiviral vectors.

STATEMENT OF INDUSTRIAL APPLICABILITY

The present disclosure has industrial applicability in the field of gene therapeutics and medical diagnostics.

SEQUENCE LISTING

The nucleic and amino acid sequences provided herein are shown using standard letter abbreviations for nucleotide bases, and three letter code for amino acids, as defined in 37 C.F.R. 1.822. The sequence listing is submitted as an ASCII text file, named "2016-05-15_Cal-004WO_ST25.txt" created on May 16, 2016, 5 KB, which is incorporated by reference herein.

BACKGROUND OF THE DISCLOSURE

HIV-1 is the causative agent of Acquired Immunodeficiency Syndrome (AIDS) with of the order of 30 million individuals infected world-wide. HIV causes the immune system to fail and increases the probability of death due to opportunistic infections. HIV infection is a major global health problem as evidenced by its designation as a pandemic by the World Health Organization. Most people who are infected with HIV, particularly in the developing world, eventually develop AIDS, which claims the lives of more than one million people every year.

HIV-1 belongs to the retroviridae family of viruses, and is an enveloped virus whose genome consists of two single stranded RNA molecules (ssRNA). The primary target of HIV-1 is CD4+ expressing cells, such as CD4+ T cells. Glycoprotein of the HIV-1 virus interacts with the CD4 molecule of target cells and with chemokine co-receptors, CCRS or CXCR4 on the surface of target cells. Following fusion and entry into the target cell, the nucleocapsid containing the viral genome dissociates, releasing the contents of the virus, including the ssRNA, into the cytoplasm. A reverse transcriptase (RT) enzyme of HIV-1 synthesizes viral double stranded DNA (dsDNA) from the ssRNA genome. Following synthesis of the double stranded HIV-1 DNA molecule, the HIV-1 DNA is integrated into the host genome.

The integrated HIV-1 DNA is flanked by identical 5' and 3' long terminal repeat sequences (LTR) from which HIV-1 can initiate transcription of the integrated HIV-1 genome. Transcription of the viral DNA requires transcription factors, such as NF-kB, which are upregulated in activated T cells. As a consequence, viral transcription is most active in the T cell following activation of the T cell, such as during infection. Viral RNA resulting from transcription of the integrated HIV-1 genome is subsequently translated and packaged into virus particles which then exit the cell to become infectious virus.

Therapy for HIV-1 infection includes combination antiretroviral therapy (cART). cART, which includes combinations of nucleoside analogue reverse transcriptase inhibitors, protease inhibitors, non-nucleoside reverse transcriptase inhibitors, integrase and fusion inhibitors, slows HIV progression. This, in turn, dramatically decreases the morbidity and mortality rate from HIV/AIDS in regions of the world where the therapy is available. However, cART does not cure or completely eliminate all the symptoms of HIV/AIDS. Also, cART therapy can be compromised by drug resistant mutations, and has a range of side effects which can be serious and which appear to be cumulative. Further, interruption of cART therapy almost invariably leads to the re-emergence of detectable viral replication and the progression to AIDS and has been shown to be associated with an increased incidence of all causes of mortality and serious non AIDS events. For these reasons, as well as the high cost of cART and need for strict adherence, such therapy can be relatively ineffective for a large number of patients.

HIV-based lentiviral vectors are rapidly becoming the retrovirus vector system of choice for research and clinical gene transfer applications. The enhanced ability of lentiviral vectors to transduce both quiescent stem cells and non-dividing terminally differentiated cells has led to the development of a wide range of therapeutic gene delivery vectors, as well as promising research tools, such as short hairpin RNA (shRNA) gene knockdown libraries and vectors for induction of pluripotency in terminally differentiated cells. Early gamma-retroviral clinical gene therapy vectors restored immune function in patients with X-linked severe combined immunodeficiency (SCID-X1), but they were subsequently found to cause proliferative disorders via transactivation of proto-oncogenes. Newer lentiviral vector designs may significantly reduce that risk, and they await clinical testing for final validation of their predicted safety. The field remains in flux and the outcomes of the clinical testing are unpredictable.

When anti-HIV-1 lentivirus based gene therapy (e.g. a dual-combination anti-HIV-1 lentiviral vector (Cal-1, LVsh5/C46)) is used to inhibit HIV-1 replication it is essential to quantify the cells containing Cal-1 DNA and those containing wild-type HIV DNA. This is particularly true for cells obtained from HIV-1 infected patients. We face the difficulty of distinguishing HIV-1 and Cal-1 at the DNA level. Current commercially available PCR based assays are unable to distinguish between HIV-1 integrated DNA and the Cal-1 transgene integrated DNA. There is an assay reported to identify HIV-1 DNA (Burke B P, et al: Mol Ther Nucleic Acids 2015, 4:e236) based on PCR to the pol region, where primers are used to detect HIV-1 sequences, which are not present within lentiviral vectors. There is also a possible assay reported to identify Cal-1 transgene DNA using C46 primer region, which are not present within HIV-1 (Wolstein O, et al: Mol Ther Methods & Clinical Development 2014, 1, 11).

SUMMARY OF THE DISCLOSURE

In one aspect of the present disclosure is a composition comprising (a) a probe comprising a nucleotide sequence having at least 80% identity to that of SEQ ID NO: 14, the probe conjugated to a reporter moiety; (b) a forward primer comprising a nucleotide sequence having at least 90% identity to that of SEQ ID NO: 2; and (c) a reverse primer comprising a nucleotide sequence having at least 80% identity to that of SEQ ID NO: 6; wherein each of the forward and reverse primers are capable of annealing to a target sequence to amplify the target sequence.

In another aspect of the present disclosure is a composition comprising (a) a probe comprising a nucleotide sequence having at least 80% identity to that of SEQ ID NO: 10; the probe conjugated to a reporter moiety; (b) a forward primer comprising a nucleotide sequence having at least 90% identity to that of SEQ ID NO: 2; and (c) a reverse primer comprising a nucleotide sequence having at least 80% identity to that of SEQ ID NO: 6; wherein each of the forward and reverse primers are capable of annealing to a target sequence to amplify the target sequence.

In another aspect of the present disclosure is a composition comprising (a) a probe comprising a nucleotide sequence having at least 80% identity to that of SEQ ID NO: 8, the probe conjugated to a reporter moiety; (b) a forward primer comprising a nucleotide sequence having at least 90% identity to that of SEQ ID NO: 4; and (c) a reverse primer comprising a nucleotide sequence having at least 80% identity to that of SEQ ID NO: 6; wherein each of the forward and reverse primers are capable of annealing to a target sequence to amplify the target sequence.

In another aspect of the present disclosure is a kit comprising a first composition and a second composition, wherein the first composition comprises (a) a probe comprising a nucleotide sequence having at least 80% identity to that of SEQ ID NO: 14, the probe conjugated to a reporter moiety; (b) a forward primer comprising a nucleotide sequence having at least 90% identity to that of SEQ ID NO: 2; and (c) a reverse primer comprising a nucleotide sequence having at least 80% identity to that of SEQ ID NO: 6; wherein each of the forward and reverse primers are capable of annealing to a target sequence to amplify the target sequence; and the second composition comprises one of (i) a composition comprising (a) a probe comprising a nucleotide sequence having at least 80% identity to that of SEQ ID NO: 10; the probe conjugated to a reporter moiety; (b) a forward primer comprising a nucleotide sequence having at least 90% identity to that of SEQ ID NO: 2; and (c) a reverse primer comprising a nucleotide sequence having at least 80% identity to that of SEQ ID NO: 6; wherein each of the forward and reverse primers are capable of annealing to a target sequence to amplify the target sequence; or (ii) a composition comprising (a) a probe comprising a nucleotide sequence having at least 80% identity to that of SEQ ID NO: 8, the probe conjugated to a reporter moiety; (b) a forward primer comprising a nucleotide sequence having at least 90% identity to that of SEQ ID NO: 4; and (c) a reverse primer comprising a nucleotide sequence having at least 80% identity to that of SEQ ID NO: 6; wherein each of the forward and reverse primers are capable of annealing to a target sequence to amplify the target sequence.

In another aspect of the present disclosure is a method of quantifying a first target sequence comprising contacting a first sample comprising the first target sequence with a composition comprising (a) a probe comprising a nucleotide sequence having at least 80% identity to that of SEQ ID NO: 14, the probe conjugated to a reporter moiety; (b) a forward primer comprising a nucleotide sequence having at least 90% identity to that of SEQ ID NO: 2; and (c) a reverse primer comprising a nucleotide sequence having at least 80% identity to that of SEQ ID NO: 6; performing a real-time polymerase chain reaction using the first target sequence as the template; and quantifying an amount of a generated first amplicon.

In some embodiments, the method further comprises quantifying a second target sequence within a second sample. In some embodiments, the second target sequence is detected using a composition comprising (a) a probe comprising a nucleotide sequence having at least 80% identity to that of SEQ ID NO: 10; the probe conjugated to a reporter moiety; (b) a forward primer comprising a nucleotide sequence having at least 90% identity to that of SEQ ID NO: 2; and (c) a reverse primer comprising a nucleotide sequence having at least 80% identity to that of SEQ ID NO: 6; wherein each of the forward and reverse primers are capable of annealing to a target sequence to amplify the target sequence. In other embodiments, the second target sequence is quantified using a composition comprising (a) a probe comprising a nucleotide sequence having at least 80% identity to that of SEQ ID NO: 8, the probe conjugated to a reporter moiety; (b) a forward primer comprising a nucleotide sequence having at least 90% identity to that of SEQ ID NO: 4; and (c) a reverse primer comprising a nucleotide sequence having at least 80% identity to that of SEQ ID NO: 6; wherein each of the forward and reverse primers are capable of annealing to a target sequence to amplify the target sequence.

In some embodiments, the first and second samples are derived from the same source and wherein the quantification of the first and second target sequences takes place in a single reaction chamber. In some embodiments, the first and second samples are derived from the same source and wherein the quantification of the first and second target sequences takes place in separate reaction chambers. In some embodiments, the first target sequence is a lentiviral nucleic acid sequence and wherein the second target sequence is a HIV nucleic acid sequence. In some embodiments, the step of quantifying the amount of the generated first amplicon comprises detecting signals from a first reporter moiety; and wherein the step of quantifying the amount of the generated second amplicon comprises detecting signals from a second reporter moiety, wherein the first and second reporter moieties are different. In some embodiments, the method further comprises assessing an efficacy of gene transfer from a lentiviral vector by comparing (i) a first ratio of the quantified amount of the generated first amplicon to the quantified amount of the generated second amplicon at a first time point; (ii) to a second ratio of the quantified amount of the generated first amplicon to the quantified amount of the generated second amplicon at a second time point. In some embodiments, an increasing ratio of lentiviral nucleic acid to HIV nucleic acid is indicative of therapeutic efficacy.

In another aspect of the present disclosure is a method of detecting a lentiviral nucleic acid and/or a HIV nucleic acid in a sample, the method comprising: (a) performing multiplex real-time PCR with a lentiviral nucleic acid template and a HIV nucleic acid template in the sample using: (i) a first forward primer having a nucleotide sequence having at least 90% identity to that of SEQ ID NO: 2, a first reverse primer having a nucleotide sequence having at least 90% identity to that of SEQ ID NO: 6, and a first probe having a nucleotide sequence having at least 90% identity to that of SEQ ID NO:14, the first probe having a first reporter moiety; (ii) a second forward primer having a nucleotide sequence having at least 90% identity to that of SEQ ID NO: 2, a second reverse primer having a nucleotide sequence having at least 90% identity to that of SEQ ID NO: 6, and a second probe having a nucleotide sequence having at least 90% identity to that of SEQ ID NO: 10, the second probe having a second reporter moiety, where the first and second reporter moieties are different; (b) detecting an amplicon generated by (i) the first forward and reverse primers, and (ii) the second forward and reverse primers; and wherein detecting comprises detecting first and second signals from the first and second reporter moieties.

In another aspect of the present disclosure is a method of detecting a lentiviral nucleic acid and/or a HIV nucleic acid in a sample, the method comprising: (a) performing multiplex real-time PCR with a lentiviral nucleic acid template and a HIV nucleic acid template in the sample using: (i) a first forward primer having a nucleotide sequence having at least 90% identity to that of SEQ ID NO: 2, a first reverse primer having a nucleotide sequence having at least 90% identity to that of SEQ ID NO: 6, and a first probe having a nucleotide sequence having at least 90% identity to that of SEQ ID NO: 14, the first probe having a first reporter moiety; (ii) a second forward primer having a nucleotide sequence having at least 90% identity to that of SEQ ID NO: 4, a second reverse primer having a nucleotide sequence having at least 90% identity to that of SEQ ID NO: 6, and a second probe having a nucleotide sequence having at least 90% identity to that of SEQ ID NO: 8, the second probe having a second reporter moiety, where the first and second reporter moieties are different; (b) detecting an amplicon generated by (i) the first forward and reverse primers, and (ii) the second forward and reverse primers; and wherein detecting comprises detecting first and second signals from the first and second reporter moieties.

In another aspect is a method of detecting an amount of a lentiviral nucleic acid in a sample comprising: (a) contacting the sample with a first forward primer and a first reverse primer; (b) contacting the sample with a junction probe specific for a junction site within the 3'LTR of the lentiviral nucleic acid, wherein the junction probe comprises a first portion which is capable of hybridizing to at least a portion of a sequence within the U3 region of the lentiviral nucleic acid 3'LTR and a second portion which is capable of hybridizing to at least a portion of a sequence within the R region of the lentiviral nucleic acid 3'LTR, and wherein the junction probe comprises a first detectable moiety; and detecting signals from the first detectable moiety. In some embodiments, the first portion of the junction probe hybridizes to a nucleotide sequence having at least 80% identity to that of SEQ ID NO: 12. In some embodiments, the second portion of the junction probe hybridizes to a nucleotide sequence of SEQ ID NO: 13. In some embodiments, the junction probe comprises a nucleotide sequence having at least 80% identity to that of SEQ ID NO: 14. In some embodiments, the junction probe comprises a nucleotide sequence having at least 90% identity to that of SEQ ID NO: 14.

In some embodiments, the method further comprises detecting an amount of an HIV nucleic acid in the sample. In some embodiments, the detection of the amount of the lentiviral nucleic acid and the amount of HIV nucleic acid in the sample takes place in the same reaction tube. In some embodiments, the detection of the amount of the HIV nucleic acid comprises contacting the sample with a second probe specific for a TATA-box sequence within a 3'LTR of an HIV nucleic acid sequence, the second probe conjugated to a second detectable moiety; and detecting signals from the second detectable moiety. In some embodiments, the second probe has a nucleotide sequence having at least 90% identity to that of SEQ ID NO: 10. In some embodiments, the first forward primer is a NuAf primer and the first reverse primer is a LTR-rev primer. In some embodiments, the NuAf primer has the sequence of SEQ ID NO: 2. In some embodiments, the LTR-rev primer has the sequence of SEQ ID NO: 6.

In some embodiments, the detection of the amount of the lentiviral nucleic acid and the amount of HIV nucleic acid in the sample takes place in different reaction tubes. In some embodiments, the detection of the amount of the HIV nucleic acid comprises contacting the sample with a second forward primer, a second reverse primer, and a second probe having a nucleotide sequence having at least 90% identity to that of SEQ ID NO: 8, wherein the second probe comprises a second detectable moiety; and detecting signals from the second detectable moiety. In some embodiments, second forward primer hybridizes to a nucleotide sequence of SEQ ID NO: 3. In some embodiments, the second forward primer comprises a nucleotide sequence having at least 80% identity to that of SEQ ID NO: 4. In some embodiments, the second reverse primer comprises the sequence of SEQ ID NO: 6.

In another aspect of the present disclosure is a method of detecting a lentiviral nucleic acid in a sample comprising: (a) contacting the sample with a first forward primer and a first reverse primer; (b) contacting the sample with a junction probe specific for a junction site within a 3'LTR of the lentiviral nucleic acid, wherein the 3'LTR of the lentiviral nucleic acid does not comprise a TATA-box sequence, and wherein the junction site spans a portion of the U3 region of the lentiviral nucleic acid 3'LTR and a portion of the R region of the lentiviral nucleic acid 3'LTR, and wherein at least a portion of the junction probe hybridizes to a nucleotide sequence of SEQ ID NO: 13. In some embodiments, the method further comprises contacting the sample with a second probe specific for a TATA-box sequence within a 3'LTR of an HIV nucleic acid sequence, the second probe having a second detectable moiety, wherein the first and second detectable moieties are different, and detecting signals from the second detectable moiety. In some embodiments, the method further comprises contacting the sample with a second forward primer, a second reverse primer, and a second probe having a nucleotide sequence having at least 80% identity to that of SEQ ID NO: 8, wherein the second probe comprises a second detectable moiety, wherein the first and second detectable moieties are different; and detecting signals from the second detectable moiety.

In another aspect of the present disclosure is a method of quantifying an amount of a lentiviral nucleic acid and an amount of an HIV nucleic acid in a sample, the lentiviral nucleic acid and the HIV nucleic acid comprising different 3'LTRs, the method comprising amplifying both the lentiviral nucleic acid and the HIV nucleic acid with a forward primer which hybridizes to a sequence within both the 3'LTR of the lentiviral nucleic acid and the 3'LTR of the HIV nucleic acid, and a reverse primer which hybridizes to a sequence within both the 3'LTR of the lentiviral nucleic acid and the 3'LTR of the HIV nucleic acid, and wherein the amplification of both the lentiviral nucleic acid and the HIV nucleic acid occur in a single reaction tube. In some embodiments, the 3'LTR of the lentiviral nucleic acid comprises at least 50 nucleotides less than the 3'LTR of the HIV nucleic acid. In some embodiments, the 3'LTR of the lentiviral nucleic acid does not comprise a TATA-box sequence. In some embodiments, amplification produces a lentiviral nucleic acid amplicon having a first size and a HIV nucleic acid amplicon having a second size, wherein the amplicon of the lentiviral nucleic acid is smaller than the amplicon of the HIV nucleic acid. In some embodiments, an electrophoretic separation is used to separate the lentiviral nucleic acid amplicon and the HIV nucleic acid amplicon. In some embodiments, the lentiviral nucleic acid 3'LTR comprises a U3 region having a nucleotide sequence of SEQ ID NO: 15. In some embodiments, the HIV nucleic acid 3'LTR comprises a U3 region having a nucleotide sequence of SEQ ID NO: 16.

In another aspect of the present disclosure is an amplicon obtainable by amplification from a lentiviral nucleic acid-containing sample with a pair of primers, the primers having SEQ ID NO: 2 and SEQ ID NO: 6, the amplicon comprising a 3'LTR that does not comprise a TATA-box sequence.

In another aspect of the present disclosure is an isolated nucleic acid sequence comprising a nucleotide sequence having at least 90% identity to that of SEQ ID NO: 14.

In another aspect of the present disclosure is an isolated nucleic acid sequence comprising a nucleotide sequence having at least 90% identity to that of SEQ ID NO: 15.

In another aspect of the present disclosure is an isolated nucleic acid sequence comprising a nucleotide sequence having at least 70% identity to that of SEQ ID NO: 14 and capable of hybridizing to a fragment of a nucleotide sequence of SEQ ID NO: 15.

In another aspect of the present disclosure is an isolated nucleic acid sequence having a first portion capable of hybridizing to a nucleotide sequence having at least 70% identity to that of SEQ ID NO:12, and a second portion capable of hybridizing to a nucleotide sequence of SEQ ID NO: 13.

In another aspect of the present disclosure is a method of quantifying an amount of a lentiviral nucleic acid in a sample, the lentiviral nucleic acid having deletions in a 3'LTR as compared with a wild-type 3'LTR, comprising amplifying the lentiviral nucleic acid using a probe specific for the deletions in the the 3'LTR of the lentiviral nucleic acid. In some embodiments, the probe specific for the deletions in the 3'LTR of the lentiviral nucleic acid comprises a first portion which hybridizes to a sequence within a U3 region of the 3'LTR of the lentiviral nucleic acid and a second portion which hybridizes to a sequence within a R region of the 3'LTR of the lentiviral nucleic acid. In some embodiments, the sequence within the U3 region of the 3'LTR of the lentiviral nucleic acid comprises a sequence selected from the group consisting of (i) a sequence having at least 90% identity to that of SEQ ID NO: 12; and (ii) SEQ ID NO: 12. In some embodiments, the sequence within the R region of the 3'LTR of the lentiviral vector comprises that of SEQ ID NO: 13. In some embodiments, the probe specific for the deletions in the 3'LTR of the lentiviral nucleic acid comprises a sequence selected from the group consisting of (i) a sequence having at least 90% identity to that of SEQ ID NO: 14; and (ii) SEQ ID NO: 14.

In some embodiments, the amplifying of the lentiviral vector nucleic acid further comprises introducing forward and reverse primers specific to sequences within the 3'LTR of the lentiviral vector nucleic acid. In some embodiments, the forward primer comprises the sequence of SEQ ID NO: 2. In some embodiments, the reverse primer comprises the sequence of SEQ ID NO: 4. In some embodiments, the method further comprises quantifying an amount of a wild-type HIV nucleic acid present in the sample. In some embodiments, the quantifying of the amount of the HIV nucleic acid present in the sample comprises amplifying the wild-type HIV nucleic acid, and wherein amplification of the wild-type HIV nucleic acid takes place in the same reaction tube as the amplification of the lentiviral nucleic acid. In some embodiments, the amplifying of the HIV nucleic acid utilizes a probe specific for a TATA-box sequence within a U3 region of the wild-type HIV nucleic acid 3'LTR. In some embodiments, the amplifying of the HIV nucleic acid comprises the same forward and reverse primers used in the amplification of the lentiviral vector nucleic acid. In some embodiments, the probe specific for the 3'LTR of the lentiviral vector nucleic acid and the probe specific for the TATA-box sequence within the U3 region of the wild-type HIV nucleic acid are each conjugated to a different detectable moiety.

In some embodiments, the amplifying of the wild-type HIV nucleic acid present in the sample takes place in a different reaction tube as the amplification of the lentiviral vector nucleic acid. In some embodiments, the amplifying of the wild-type HIV nucleic acid utilizes a probe specific for a sequence within a R region of the 3'LTR of the wild-type HIV nucleic acid. In some embodiments, the amplifying of the HIV nucleic acid comprises the same reverse primer as used in the amplification of the lentiviral vector nucleic acid. In some embodiments, the amplifying of the wild-type HIV nucleic acid comprises a forward primer specific for a TATA-box sequence within a U3 region of the 3'LTR of the wild-type HIV nucleic acid. In some embodiments, the probe specific for the 3'LTR of the lentiviral vector nucleic acid and the probe specific for a sequence within the R region of the wild-type HIV nucleic acid are each conjugated to a different detectable moiety.

In another aspect of the present disclosure is a method of discriminating between a lentiviral nucleic acid and an HIV nucleic acid present in a sample, the lentiviral nucleic acid comprising a 3'LTR having a U3 region that does not contain a TATA-box sequence, comprising amplifying the lentiviral nucleic acid with a first probe specific to a sequence within the 3'LTR of the lentiviral nucleic acid and amplifying the HIV nucleic acid with a second probe specific to a sequence within a 3'LTR of the HIV nucleic acid.

BRIEF DESCRIPTION OF THE DRAWINGS

FIG. 1B illustrates that there is no TATA-box in the Cal-1 U3 region, which indicates a mismatched sequence between the U3 region of Cal-1 and HXB2. The mismatched sequences are denoted by dots. FIG. 1C also illustrates the R region of the 3'LTR of Cal-1, where the R region of Cal-1 and HIV have the same sequence. FIG. 1C illustrates a "junction site" of Cal-1, the junction site bridging a sequence which would be present in a wild-type U3 region. FIG. 1C again illustrates the differences between the U3 region of Cal-1 and a wild-type U3 region, such as in HIV. FIGS. 1D through 1I further illustrates the difference between the U3 regions of Cal-1 and HIV.

FIG. 5A showed reverse transcriptase (RT) assay data. FIGS. 5B and 5C show quantification results of HIV-1 RNA and Cal-1 RNA copy number using a single tube assay in accordance with a Multiplexed Method-1 described herein.

FIG. 16A summarizes HIV DNA copies per 1,000 human spleen cells, the data obtained through a BLT infectious model.

FIG. 16B summarizes HIV DNA copies per 10^3 (actin copy) human spleen cells, the data obtained through a BLT infectious model.

FIG. 16C summarizes vector copy number per 1,000 human spleen cells, the data obtained through a BLT infectious model.

FIG. 16D summarizes vector copy number per 10^3 (actin copy) human spleen cells, the data obtained through a BLT infectious model.

FIG. 17 provides data used to generate the summary tables of FIGS. 16A through 16D, including standard curves.

DETAILED DESCRIPTION

Figure 1A:
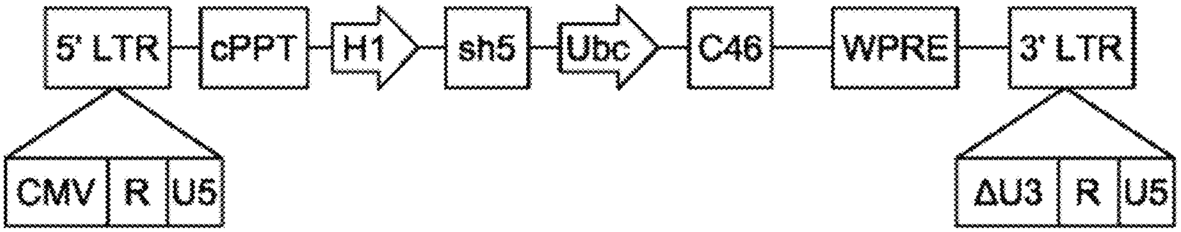
FIG. 1A is a schematic representation of the LVsh5/C46 lentiviral vector, where CCR5 shRNA (sh5) is under the human H1 RNA polymerase III promoter; and C46 is under the Ubiquitin C promoter (UbC). Other components of the LVsh5/C46 vector include 5' and 3' modified HIV-1 long terminal repeats (LTRs), a central polypurine tract (cPPT), and a woodchuck hepatitis virus posttranscriptional regulatory element (WPRE). Notably, the TATA-box of U3 region was deleted in LVsh5/C46, as described further herein, which distinguishes it from a wild-type U3 region.
Figure 1B:
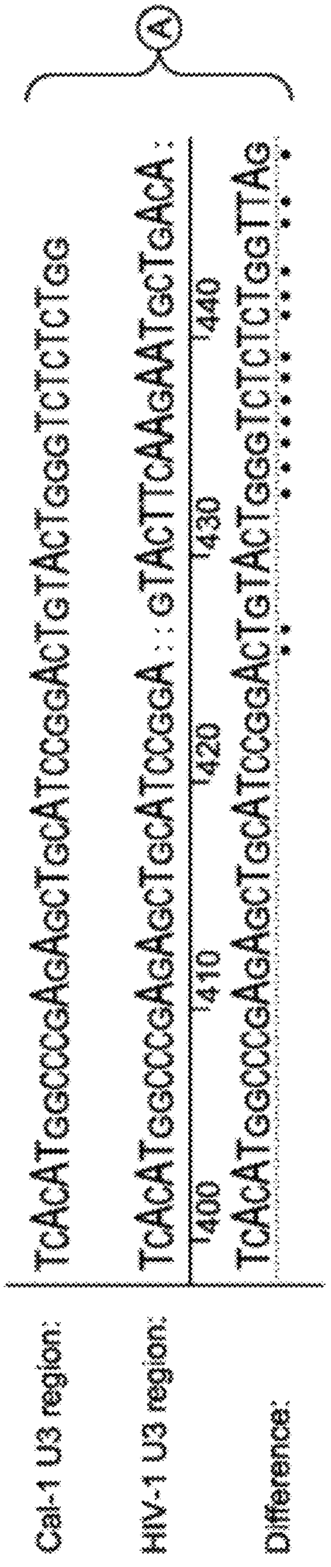
FIGS. 1B through 1I provide alignments between the U3 region of the 3'LTR of one particular lentiviral vector, namely Cal-1, and a U3 region of a wild-type 3'LTR, such as found in HIV-1 (HXB2).

In general, the present disclosure provides compositions (i.e., amplification primers and probes), methods, and kits that are particularly useful for detecting and/or quantifying nucleic acids present in a sample, such as those derived from HIV or a lentiviral vector.

Definitions

As used herein, the singular terms "a," "an," and "the" include plural referents unless the context clearly indicates otherwise. Similarly, the word "or" is intended to include "and" unless the context clearly indicates otherwise.

As used herein, An "amplicon" is defined as any nucleic acid molecule produced by a nucleic acid amplification technique. In particular, an amplicon comprises a sequence that hybridizes with a primer when contacted therewith, and that can be either an entire molecule or a portion thereof.

"Amplification" of a target nucleic acid sequence shall mean an in vitro target amplification technique whereby target sequences are copied, producing amplicons which serve as templates for further cycles of amplification.

As used herein, "Cal-1" refers to a lentiviral vector comprising a short hairpin RNA CCR5 and a C46 fusion inhibitor. Further details regarding Cal-1 are described in co-pending the the co-pending application published as US Publication No. US2012/0201794, the disclosure of which is incorporated by reference herein in its entirety.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c.

Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein, the term "human immunodeficiency virus" (HIV) refers to any HIV including laboratory strains, wild type strains, mutant strains and any biological sample comprising at least one HIV virus, such as, for example, an HIV clinical isolate. HIV strains compatible with the present methods are any such strains that are capable of infecting mammals, particularly humans. Examples are HIV-1, HIV-2, and SIV.

As used herein, the term "lentiviral vector" is used to denote any form of a nucleic acid derived from a lentivirus and used to transfer genetic material into a cell via transduction. The term encompasses lentiviral vector nucleic acids, such as DNA and RNA, encapsulated forms of these nucleic acids, and viral particles in which the viral vector nucleic acids have been packaged.

As used herein, the term "long terminal repeat" (LTR) is used in reference to domains of base pairs located at the ends of retroviral DNAs. These LTRs may be several hundred base pairs in length. LTRs often provide functions fundamental to the expression of most eukaryotic genes (e.g., promotion, initiation and polyadenylation of transcripts). In general, the LTR comprises enhancer and promoter regions for gene expression (U3), and the RNA start site, and the untranslated RNA sequences (R/U5) such as the genomic repeat and polyadenylation sites.

As used herein, the term "primer" refers a short segment of DNA or DNA-containing nucleic acid molecule, which (i) anneals under amplification conditions to a suitable portion of a DNA or RNA sequence to be amplified, and (ii) initiates, and is itself physically extended, via polymerase-mediated synthesis.

As used herein, the term "probe" refers to an oligonucleotide (i.e. a sequence of nucleotides), whether occurring naturally as in a purified restriction digest or produced synthetically, which is capable of hybridizing to another oligonucleotide of interest. Probes are useful in the detection, identification and isolation of particular gene sequences. It is contemplated that any probe used in the present disclosure will be labelled with a "reporter molecule" or "detectable moiety" such that is detectable in any detection system, including, but not limited to enzyme (e.g., ELISA, as well as enzyme-based histochemical assays), fluorescent, radioactive, calorimetric, and luminescent systems.

As used herein, the term "TAR" refers to the "trans-activation response" genetic element located in the R region of the LTR. This element mediates the action of tat, by physically binding to the viral trans-activator tat.

As used herein, the phrases "target sequence" or "target nucleic acid" each refer to a region of a nucleic acid which is to be amplified, detected, or otherwise analyzed.

As used herein, "Tat" refers to the virally encoded trans-activating protein which functions as an elongation factor. Tat is essential for viral replication as the key viral element for increasing HIV gene expression.

As used herein, the term "TATA box" is used in reference to a segment of DNA, located approximately 19-27 base pairs upstream from the start point of eukaryotic structural genes, to which RNA polymerase binds. The TATA box is approximately 7 base pairs in length, often comprising the sequence "TATAAAA." The TATA box is also sometimes referred to as the "Hogness box."

As used herein, the terms "transduce" or "transduction" refers to the delivery of a gene(s) using a viral or retroviral vector by means of infection rather than by transfection. For example, an anti-HIV gene carried by a retroviral vector (a modified retrovirus used as a vector for introduction of nucleic acid into cells) can be transduced into a cell through infection and provirus integration. Thus, a "transduced gene" is a gene that has been introduced into the cell via lentiviral or vector infection and provirus integration. Viral vectors (e.g., "transducing vectors") transduce genes into "target cells" or host cells.

As used herein, the term "transgene" is a nucleic acid sequence within a lentiviral vector that is not normally present in a cell to be transduced with the lentiviral vector. The lentiviral vector serves to introduce this sequence into the transduced cell.

As used herein, the term "vector" is used in reference to nucleic acid molecules that transfer nucleic acid (e.g., DNA) segment(s) from one cell to another.

As used herein thee term "wild-type" refers to a gene or nucleic acid sequence which is most frequently observed in a population and is thus arbitrarily designed the "normal" or "wild-type" form of the gene or nucleic acid sequence.

Lentiviral Vectors

In some embodiments, the lentiviral vector comprises an inactivated or self-inactivating 3'LTR. A "self-inactivating 3'LTR" is a 3'LTR that contains a mutation, substitution or deletion that prevents the LTR sequences from driving expression of a downstream gene. It is believed that a copy of the U3 region from the 3'LTR acts as a template for the generation of LTRs in the integrated provirus. Thus, when the 3'LTR with an inactivating deletion or mutation integrates as the 5'LTR of the provirus, no transcription from the 5'LTR is possible. This eliminates competition between the viral enhancer/promoter and any internal enhancer/promoter. Self-inactivating 3'LTRs are described, for example, in Zufferey et al., J. Virol., Vol. 72:9873-9880, 1998; Miyoshi et at, J. Virol., Vol. 72:8150-8157, 1998; and Iwakuma et al., Virology, Vol. 261:120-132, 1999. The 3'LTR may be made self-inactivating by any method known in the art. In one embodiment, the U3 element or region of the 3'LTR contains a deletion of its enhancer sequence, preferably the TATA box, Spl and NF-kappa B sites. As a result of the self-inactivating 3'LTR, the provirus that is integrated into the host cell genome will comprise an inactivated 5'LTR. The viral expression vectors of the disclosure preferably do not inhibit vector production in producer cells.

In general, self-inactivating recombinant lentiviral vectors (SIN) of the present disclosure comprise a 3'LTR which has been rendered substantially transcriptionally inactive by virtue of deletions of sequences within the U3 region. In some embodiments, the lentiviral vectors comprise deletions in the U3 region of the 3'LTR, including removal of a TATA-box sequence (e.g. the sequence of SEQ ID NO: 11 is missing from the U3 region of the 3'LTR of a lentiviral vector). In the case of HIV-based lentiviral vectors, such vectors tolerate significant U3 deletions, including the removal of the LTR TATA box, without significant reductions in vector titers. Therefore, in some embodiments, the lentiviral vectors comprise the removal of between about 100 and about 160 nucleotides from the U3 region of the 3'LTR as compared with a wild-type U3 3'LTR region. In other embodiments, the lentiviral vectors comprise the removal of between about 120 and about 140 nucleotides from the U3 region of the 3'LTR as compared with a wild-type U3 3'LTR region. In some embodiments, the lentiviral vectors comprise the removal of about 132 nucleotides from the U3 region of the 3'LTR as compared with a wild-type U3 3'LTR region.

By way of example, SEQ ID NO. 16 provides a wild-type U3 3'LTR region (also referred to herein as "wild-type U3 region" or "wild-type HIV"); while SEQ ID NO. 15 provides a modified U3 region, such as found in a lentiviral vector. When SEQ ID NO: 15 and SEQ ID NO: 16 are compared, the skilled artisan will appreciate that about 132 nucleotides were deleted in the U3 region of the lentiviral vector 3'LTR, including the removal of the TATA-box. In some embodiments, the R region of the 3'LTR is unaltered, i.e. a wild-type R region (see, for example, SEQ ID NO: 17).

One example of a lentiviral vector having a U3 region devoid of a TATA-box is the "Cal-1" (LVsh5/C46) lentiviral vector depicted in FIG. 1A. As illustrated in FIGS. 1B and 1D through 1I, Cal-1 comprises deletions within the U3 region of the 3'LTR spanning from nucleotide 423 to 556, and such deletions extend through the TATA-box (namely the sequence of SEQ ID NO: 11). In comparison to Cal-1, the wild-type U3 region of the 3'LTR of HIV comprises an intact TATA-box (see, for example, FIGS. 1B and 1D through 1I). In fact, the U3 region of wild-type HIV contains the enhancer and promoter elements that modulate basal and induced expression of the HIV genome in infected cells and in response to cell activation. Of course, the skilled artisan will appreciate that Cal-1 merely illustrates a single lentiviral vector and that other vectors may have a different 3'LTR region, e.g. including U3 regions having different sequences or comprising different nucleotide deletions as compared with a wild-type U3 region, and these different lentiviral vectors may be detected according to the methods disclosed herein.

Overview of Method

The assay methods disclosed herein exploit the differences in the U3 regions of the 3'LTRs of lentiviral vectors and wild-type HIV, and thus allow for specifically designed primers and/or probes to hybridize to lentiviral vectors but not to wild-type HIV, and vice-versa, as described herein.

Primers

Those skilled in the art will understand that primer sequences with suitable hybridization characteristics can be designed based on the the structures of the 3'LTR of lentiviral vectors and HIV. For example, the skilled artisan will understand that primers may be designed with suitable hybridization characteristics based on the sequences of the 3'LTR of lentiviral vectors. The primers disclosed herein are particularly contemplated as components of multiplex amplification reactions wherein several amplicon species can be produced from the target-specific primers described herein.

In some embodiments, a forward primer is selected such that it hybridizes to a sequence within a U3 region of the 3'LTR of the lentiviral vector and/or HIV. In some embodiments, and as described in further detail herein, the same forward primer is used in the amplification of both the lentiviral vector and HIV (see FIGS. 2 and 4). In other embodiments, different forward primers are used to amplify the lentiviral vector and HIV (see FIG. 3).

In some embodiments, the forward primer is selected such that it hybridizes to a sequence within a U3 region of a 3'LTR having at least 85% identity to that of SEQ ID NO: 1. In other embodiments, the forward primer is selected such that it hybridizes to a sequence within a U3 region of a 3'LTR having at least 90% identity to that of SEQ ID NO: 1. In yet other embodiments, the forward primer is selected such that it hybridizes to a sequence within a U3 region of a 3'LTR having at least 95% identity to that of SEQ ID NO: 1.

In some embodiments, the forward primer is selected such that it hybridizes to a sequence within a U3 region of a 3'LTR having at least 85% identity to that of SEQ ID NO: 3. In other embodiments, the forward primer is selected such that it hybridizes to a sequence within a U3 region of a 3'LTR having at least 90% identity to that of SEQ ID NO: 3. In yet other embodiments, the forward primer is selected such that it hybridizes to a sequence within a U3 region of a 3'LTR having at least 95% identity to that of SEQ ID NO: 3.

One forward primer suitable for use with the assays described herein is a NuAf primer. The skilled artisan will appreciate that, depending on the U3 sequences of the lentiviral vector and HIV, that the NuAf primer is capable of hybridizing to both lentiviral vectors and HIV. In some embodiments, the NuAf primer comprises the sequence of SEQ ID NO: 2 or a sequence having at least 90% identity to that of the sequence of SEQ ID NO: 2 (see FIGS. 2 and 4).

Another forward primer suitable for use with the assays disclosed herein is a TATA primer. The TATA primer is capable of hybridizing to HIV, but not to lentiviral vectors missing or devoid of a TATA-box sequence in the U3 region of the 3'LTR. The TATA primer comprises the sequence of SEQ ID NO:4 or a sequence having at least 90% identity to that of the sequence of SEQ ID NO: 4 (see FIG. 3).

In some embodiments, a reverse primer is selected such that it hybridizes to a sequence within a R region of a 3'LTR. In other embodiments, a reverse primer is selected such that it hybridizes to a sequence at the 5' end of the R region of the 3'LTR. As will be described further herein, in some embodiments, the same reverse primer is used in the amplification of both the lentiviral vector and wild-type HIV, i.e. the reverse primer is designed to a sequence common within the R region of both the lentiviral vector and wild-type HIV.

In some embodiments, the reverse primer is selected such that it hybridizes to a sequence within a R region of a 3'LTR having at least 85% identity to that of SEQ ID NO: 5. In other embodiments, the reverse primer is selected such that it hybridizes to a sequence within a R region of a 3'LTR having at least 90% identity to that of SEQ ID NO: 5. In yet other embodiments, the reverse primer is selected such that it hybridizes to a sequence within a R region of a 3'LTR having at least 95% identity to that of SEQ ID NO: 5.

One reverse primer suitable for use with the disclosed assays is a LTR-rev primer. The LTR-rev primer comprises the sequence of SEQ ID NO: 6. The LTR-rev primer is capable of hybridizing to both lentiviral vectors and HIV.

Probes

In general, the probes utilized in the methods disclosed herein belong to a class of probes called "FRET probes" (Förster or fluorescence resonance energy transfer), i.e. those containing a fluorescent reporter and quencher pair. In some embodiments, the probes utilized in the methods described herein are TAQMAN® probes. The TAQMAN® probes (Heid et al., 1996) use the fluorogenic 5' exonuclease activity of Taq polymerase to measure the amount of target sequences in nucleic acid samples. TAQMAN® probes are oligonucleotides that contain a fluorescent dye usually at or near the 5' base, and a quenching moiety typically at or near the 3' base. The quencher moiety may be a dye such as TAMRA or may be a non-fluorescent molecule such as 4-(4-dimethylaminophenylazo)benzoic acid (DABCYL). When irradiated, the excited fluorescent dye transfers energy to the nearby quenching dye molecule rather than fluorescing (FRET, as noted above). Thus, the close proximity of the reporter and quencher prevents emission of any fluorescence while the probe is intact. TAQMAN® probes are designed to anneal to an internal region of a PCR product. When the polymerase replicates a template on which a TAQMAN® probe is bound, its 5' exonuclease activity cleaves the probe. This ends the activity of quencher (no FRET) and the reporter dye starts to emit fluorescence which increases in each cycle proportional to the rate of probe cleavage. Accumulation of PCR products is detected by monitoring the increase in fluorescence of the reporter dye (in this process, only the probes are FRET labeled and primers are not labeled). The TAQMAN® assay uses universal thermal cycling parameters and PCR reaction conditions. Because the cleavage occurs only if the probe hybridizes to the target, the fluorescence detected originates from specific amplification. The process of hybridization and cleavage does not interfere with the exponential accumulation of the product.

In other embodiments, the probes utilized in the disclosed methods are molecular beacons. Molecular beacons are probes for the identification of specific nucleotide sequences present within cells (Tyagi et al., (1998) Nature Biotechnology 16:49-53). The molecular beacon can be composed of nucleic acid only such as DNA or RNA, or it can be composed of a peptide nucleic acid (PNA) conjugate. Binding of the molecular beacon to specific nucleotide sequences allows for the identification of the presence of those sequences either in vitro or in vivo. A molecular beacon includes a conjugate (e.g., a structure such as a quantum dot-tagged bead), a probe, a fluorophore, and a quenching moiety. The probe is a single-stranded oligonucleotide comprising a stem and loop structure wherein a hydrophilic attachment group is attached to one end of the single-stranded oligonucleotide and the quenching moiety is attached to the other end of the single-stranded oligonucleotide. The fluorophore can be any fluorescent organic dye or a single quantum dot such that its emission does not overlap with that of the quantum dot-tagged bead. The quenching moiety desirably quenches the luminescence of the fluorophore. Any suitable quenching moiety that quenches the luminescence of the fluorophore can be used in the conjugate described above.

In yet other embodiments, the probes utilized in the disclosed methods are dual hybridization probes. In general, dual hybridization probes use two sequence-specific oligonucleotide probes in addition to two sequence-specific DNA primers. The two probes are designed to bind to adjacent sequences in the target. The dual hybridization probes are labeled with a pair of dyes that exhibit FRET. The donor dye is attached to the 3' end of the first probe, while the acceptor dye is attached to the 5' end of the second probe.

During real-time PCR, excitation is performed at a wavelength specific to the donor dye, and the reaction is monitored at the emission wavelength of the acceptor dye. At the annealing step, the probes hybridize to their target sequences in a head-to-tail arrangement. This annealing brings the donor and acceptor dyes into proximity, allowing FRET to occur, resulting in fluorescent emission by the acceptor. The increasing amount of acceptor fluorescence is proportional to the amount of PCR product present.

Those skilled in the art will appreciate that probes with suitable hybridization characteristics can be designed based on the structures and sequences of the lentiviral vectors and wild-type HIV. For example, the skilled artisan will understand that probes may be designed based on the sequences of the U3 and R regions of the 3'LTR that are unique to the lentiviral vector or HIV. For example, a probe may be designed that hybridizes to a lentiviral vector U3 region to the exclusion of a wild-type U3 3'LTR region and vice-versa. As noted herein, certain lentiviral vectors comprise a U3 region that, as compared with a wild-type U3 region, comprise certain deletions within the U3 sequence, and the skilled artisan will be able to design a probe to hybridize to these lentiviral vector U3 regions, but not to wild-type U3 regions.

Figure 1C:
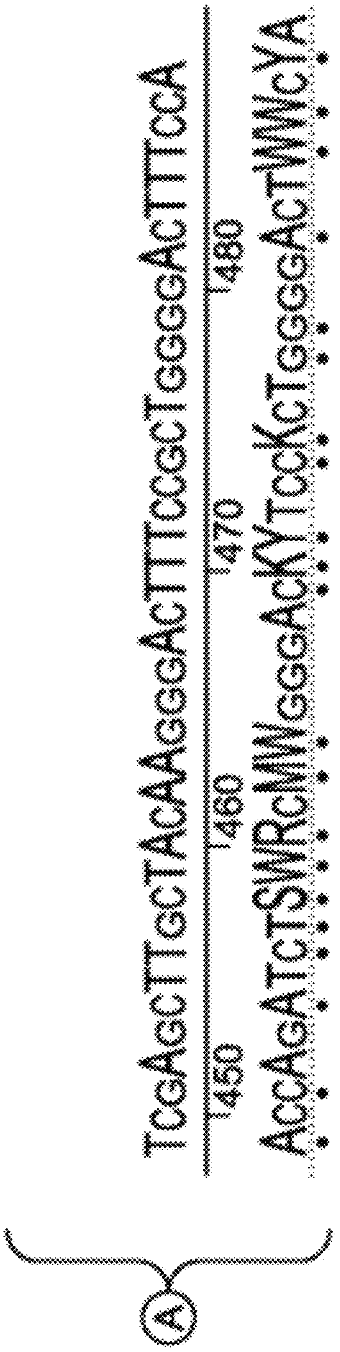
Figure 1D:
Figure 1E:
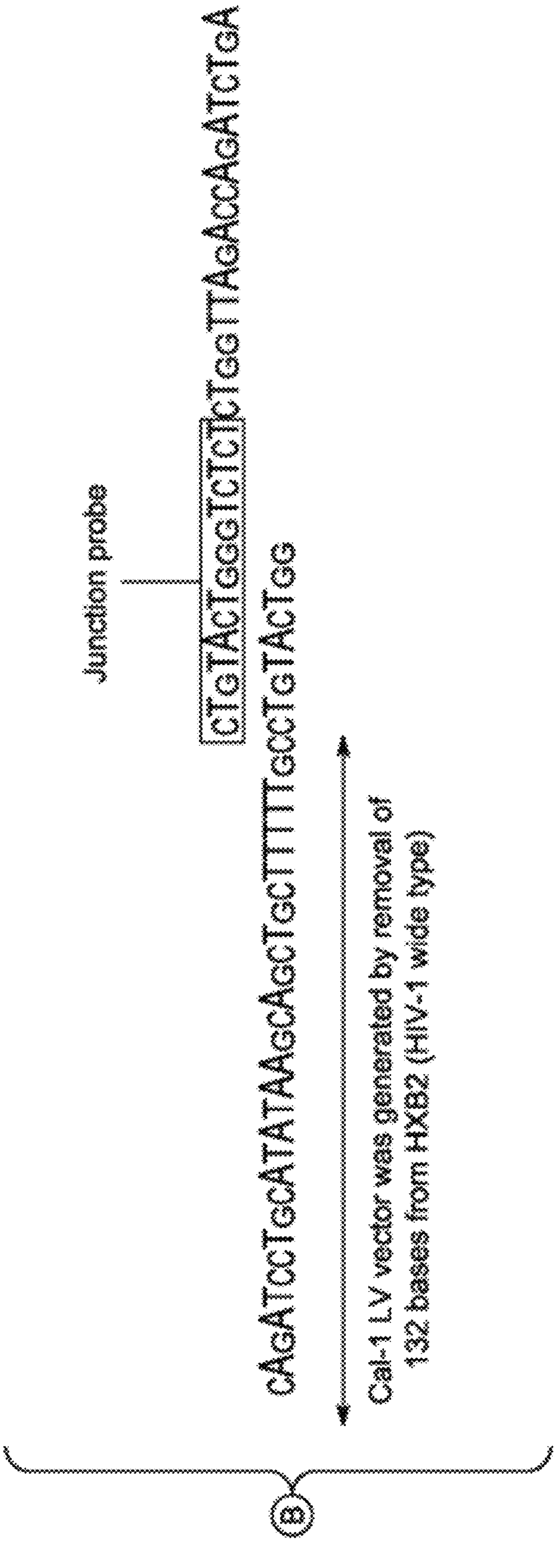
Figure 1F:
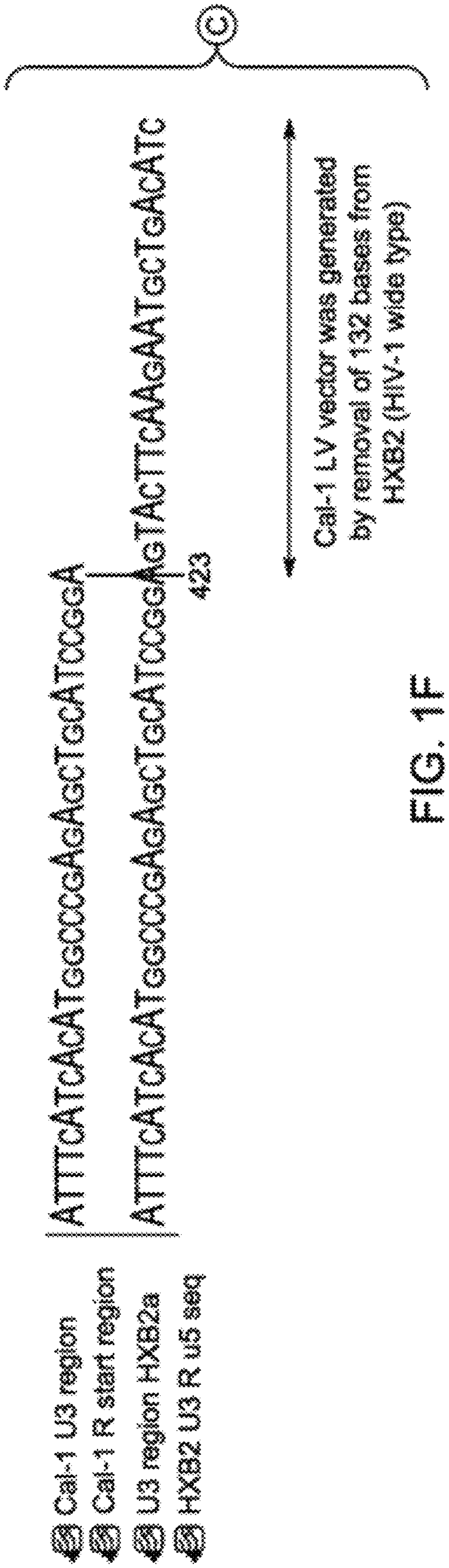
Figure 1G:
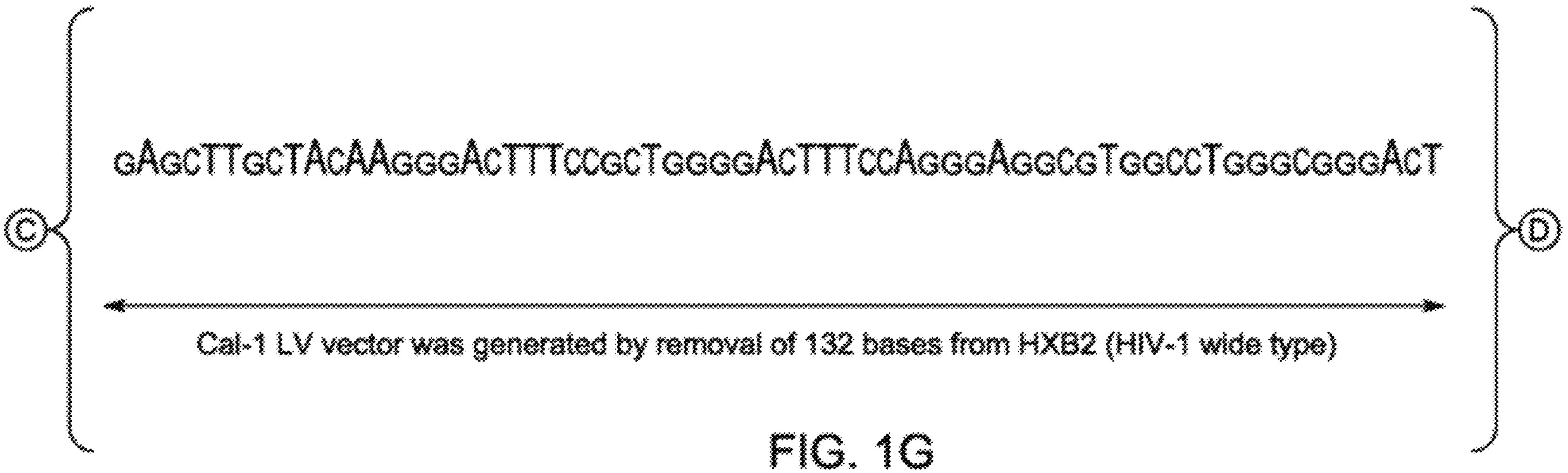
Figure 1H:
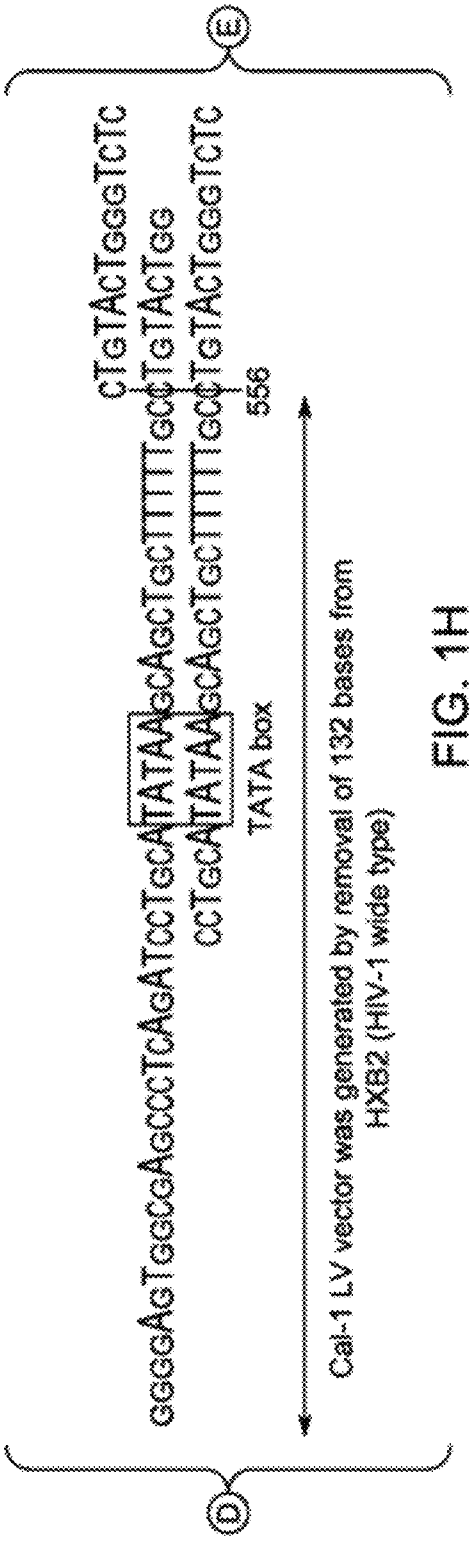
Figure 1I:
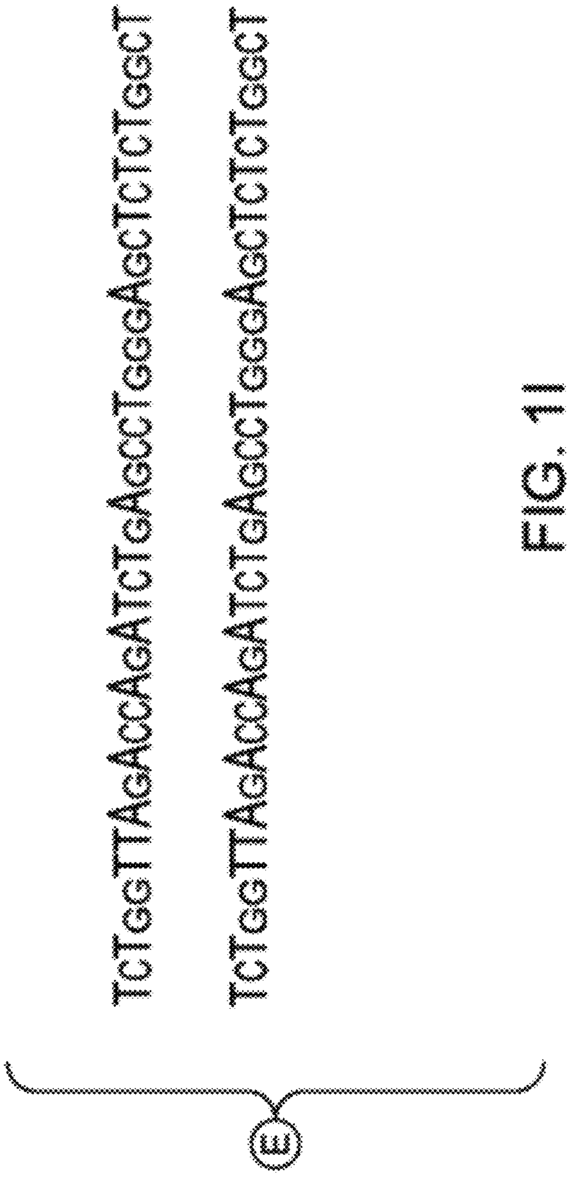

In some embodiments, the methods disclosed herein utilize a junction probe that anneals to sequences spanning the U3 region and the R region of the 3'LTR of the lentiviral vector (i.e. a "junction site"). FIG. 1C illustrates a junction site of a lentiviral vector, the junction site comprising a U3 region that comprises certain deletions compared to a wild-type U3 region. An appropriately designed junction probe may comprise a portion which hybridizes to this junction site or to a portion or fragment of this junction site. In some embodiments, the junction probe comprises a first portion and a second portion, wherein the first portion is designed to hybridize to a portion or a fragment of a nucleotide sequence within the U3 region of the 3'LTR of the lentiviral vector; and wherein the second portion is designed to hybridize to a portion or a fragment of a nucleotide sequence within the R region of the 3'LTR.

In some embodiments, the U3 region of the 3'LTR in which the junction probe hybridizes comprises a sequence having at least 80% identify to that of SEQ ID NO: 12. In other embodiments, the U3 region of the 3'LTR of the lentiviral vector in which the junction probe hybridizes comprises a sequence having at least 90% identify to that of SEQ ID NO: 12. In further embodiments, the U3 region of the 3'LTR of the lentiviral vector in which the junction probe hybridizes comprises a sequence having at least 95% identify to that of SEQ ID NO: 12. In yet further embodiments, the U3 region of the 3'LTR of the lentiviral vector in which the junction probe hybridizes comprises the sequence of SEQ ID NO: 12.

In some embodiments, the R region of the 3'LTR of the lentiviral vector in which the junction probe hybridizes comprises a sequence having at least 90% identify to that of SEQ ID NO: 13. In other embodiments, the R region of the 3'LTR of the lentiviral vector in which the junction probe hybridizes comprises the sequence of SEQ ID NO: 13.

The skilled artisan will recognize that any junction probe may be designed to accommodate the different U3 regions and R regions of any lentiviral vector. In some embodiments, the junction probe comprises the sequence of SEQ ID NO: 14, or a sequence having at least 90% identity to that of SEQ ID NO: 14. In some embodiments, the junction probe is conjugated to a detectable moiety, such as a fluorescent reporter. In some embodiments, the fluorescent reporter is selected from the group consisting of Tex-615, Tye-563, Tye-665, Joe, Cy3, Max, Rox, Tet, Texas Red-X, Tamara, & Yakima Yellow. In other embodiments, the fluorescent reporter comprises a cyanine dye, such as indodicarbocynanine (Cy5TM).

Another probe suitable for use with the disclosed assays is a TAR-probe, i.e. a probe specific to the TAR element in the 3'LTR of HIV. In some embodiments, the TAR-probe is a TaqMan® probe, such as described herein. In some embodiments, the probe is selected such that it hybridizes to a sequence within the 3'LTR having at least 85% identity to that of SEQ ID NO: 7. In other embodiments, the TAR-probe is selected such that it hybridizes to a sequence within the 3'LTR having at least 90% identity to that of SEQ ID NO: 7. In yet other embodiments, the TAR-probe is selected such that it hybridizes to a sequence within the 3'LTR having at least 95% identity to that of SEQ ID NO: 7. In some embodiments, the TAR-probe comprises the sequence of SEQ ID NO: 8. In some embodiments, the TAR-probe is conjugated to a detectable moiety, such as a fluorescent reporter. In some embodiments, the fluorescent reporter is selected from the group consisting of Tex-615, Tye-563, Tye-665, Joe, Cy3, Max, Rox, Tet, Texas Red-X, Tamara, & Yakima Yellow. In other embodiments, the TAR-probe contains a fluorescent reporter and a quencher. In some embodiments, the fluorescent reporter is fluorescein (CAS 2321-07-5).

Another probe suitable for use with the disclosed assays is a TATA-probe, i.e. a probe specific to the TATA-box in the U3 region of a wild-type 3'LTR. In some embodiments, the TATA-probe is a TaqMan® probe. In some embodiments, the TATA-probe hybridizes (anti-sense strand targeted) to U3 sequences of the 3'LTR. In some embodiments, the TATA-probe probe is selected such that it hybridizes to a sequence within the 3'LTR having at least 85% identity to that of SEQ ID NO: 9. In other embodiments, the TATA-probe is selected such that it hybridizes to a sequence within the U3 region of the 3'LTR having at least 90% identity to that of SEQ ID NO: 9. In yet other embodiments, the TATA-probe is selected such that it hybridizes to a sequence within the U3 region of the 3'LTR having at least 95% identity to that of SEQ ID NO: 9. In some embodiments, the TATA-probe comprises the sequence of SEQ ID NO: 10. In some embodiments, the TATA-probe contains a fluorescent reporter and a quencher. In some embodiments, the fluorescent reporter is selected from the group consisting of Tex-615, Tye-563, Tye-665, Joe, Cy3, Max, Rox, Tet, Texas Red-X, Tamara, and Yakima Yellow. In other embodiments, the TAR-probe contains a fluorescent reporter and a quencher. In some embodiments, the fluorescent reporter is fluorescein (CAS 2321-07-5).

Assay Methods

Samples may be collected using standard DNA extraction kits available on the market and known to those of ordinary skill in the art. In some embodiments, the DNA extraction kit is a BioLine DNA extraction kit (available from BioLine, Taunton, Mass.). In some embodiments, non-limiting sources for samples include blood samples, plasma samples, tissue samples, biopsy samples, or samples created after sorting by flow cytometry.

DNA, e.g. proviral DNA or transgene DNA, may be extracted from the sample using methods known by the skilled in the art such as the procedure described by Maniatis et al., Molecular cloning: A laboratory manual, (Cold Spring Harbor Laboratory, Cold Spring Harbor, N.Y.), 1982, the disclosure of which is hereby incorporated by reference herein in its entirety. The procedure involves the preparation of a cell lysate followed by digestion with proteinase K, obtaining DNA purification by a multi-step phenol extraction, ethanol precipitation and ribonuclease digestion.

Instead of DNA, RNA may be used in the assay methods described herein. When RNA is used, reverse transcription into complementary DNA (cDNA) by a suitable reverse transcriptase is needed. The methods which follow describing the amplification and subsequent analysis of DNA are therefore amenable for RNA analysis. In some embodiments, viral RNA may be isolated using known methods such as that described in Boom, R. et al. (J. Clin. Microbiol. 28(3): 495-503 (1990); incorporated herein by reference), or through other conventional methods such as the acid phenol method (e.g., the acid guanidinum-phenol-chloroform (AGPC) method), the guanidinium isothiocyanate procedure, thus employing the method of Chomczynski and Sacchi (Anal. Biochem. 162, 156-159 (1987)). In some embodiments, cDNA may be synthetized with SENSISCRIPT® RT (Qiagen). In some embodiments, a one-step reverse transcriptase and Taq-polymerase kit is utilized. In other embodiments, cDNA is synthesized, followed by a real-time DNA PCR method.

Amplification

Techniques for the amplification of nucleic acid sequences are known to those of ordinary skill in the art. One method of amplifying a target sequence is with a polymerase mediated technique called polymerase chain reaction (PCR). In general, PCR is a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers are then annealed to their complementary sequences within the target molecule. Following annealing, the primers are extended with a polymerase (e.g. DNA polymerase) so as to form a new pair of complementary strands. The steps of denaturation, primer annealing and polymerase extension can be repeated many times (i.e., denaturation, annealing and extension constitute one “cycle”; there can be numerous “cycles”) to obtain a high concentration of an amplified segment (the amplicon) of the desired target sequence. The length of the amplified segment of the desired target sequence is determined by the relative positions of the primers with respect to each other, and therefore, this length is a controllable parameter. Polymerase chain reaction (“PCR”) is described, for example, in U.S. Pat. Nos. 4,683,202; 4,683,195; 4,000,159; 4,965,188; 5,176,995), the disclosures of each are hereby incorporated by reference herein in their entirety.

PCR may be used qualitatively or quantitatively. One known quantitative amplification technique is “real time PCR.” The term “real time PCR” as used herein means that a signal emitted from the PCR assay is monitored during the reaction as an indicator of amplicon production during each PCR amplification cycle, i.e. in “real time,” as opposed to conventional PCR methods, in which an assay signal is detected at the endpoint of the PCR reaction. Real time PCR is generally based on the detection and quantitation of a fluorescent reporter, such as those described herein. The signal of the reporter increases in direct proportion to the amount of PCR product in a reaction. Therefore, by recording the amount of fluorescence emission at each cycle, it is possible to monitor the PCR reaction during an exponential phase where the first significant increase in the amount of PCR product correlates to the initial amount of target template. For a general description of “real time PCR” see Dehee et al. J. Virol. Meth. 102:37-51 (2002); and Aldea et al. J. Clin. Microbiol., 40:1060-1062 (2002), the disclosures of which are hereby incorporated by reference herein in their entirety.

Reverse transcriptase-polymerase chain reaction refers to generating complementary DNA from an RNA template, and further using the complementary DNA as a template for performing PCR to duplicate, described above, and amplify DNA. In the reverse-transcriptase reaction, the reaction mixtures are incubated at a temperature sufficient to synthesize a DNA molecule complementary to all or portion of the RNA template. After the reverse transcription reaction, the reaction is incubated at a temperature sufficient to amplify the synthesized DNA molecule.

Amplification of a Lentiviral Nucleic Acid

In one aspect of the present disclosure is a method of amplifying a lentiviral nucleic acid, e.g. a lentiviral transgene. In some embodiments, amplification of the lentiviral nucleic acid utilizes a forward primer which hybridizes to a portion of the U3 region of the 3'LTR and a reverse primer which hybridizes to a portion of the R region of the 3'LTR. In some embodiments, amplification of the lentiviral nucleic acid utilizes a NuAf forward primer and a LTR-rev reverse primer. In some embodiments, the amplicon produced from amplification comprise between about 100 and about 600 nucleic acids. In some embodiments, an amount of the produced amplicon is quantified.

In some embodiments, the amplification of the lentiviral nucleic acid comprises the employment of a probe specific to a sequence within the 3'LTR of the lentiviral vector, i.e. the probe will only hybridize to the 3'LTR of the lentiviral vector and will not hybridize to a wild-type 3'LTR, such as the 3'LTR of HIV. In some embodiments, the probe is optimized for the deletions in the U3 region of the 3'LTR of the lentiviral vector, as compared with a wild-type 3'LTR that does not comprise such deletions. In some embodiments, the deletions include the deletion of a TATA-box sequences (again as compared with a wild-type U3 region). In some embodiments, the probe optimized for the deletions in the U3 region of the 3'LTR is designed to span a portion of the U3 region of the 3'LTR of the lentiviral vector and a portion of the R region of the 3'LTR of the lentiviral vector. In some embodiments, the probe optimized for the deletions in the U3 region of the 3'LTR is a junction probe. In some embodiments, the junction probe comprises a sequence having at least 90% identify to that of SEQ ID NO: 14. In some embodiments, the amplification of the lentiviral nucleic acid or lentiviral transgene comprises quantifying an amount of an amplified nucleic acid, such as by detecting an amount of a fluorescent reporter conjugated the probe.

In some embodiments, the amplification of the lentiviral nucleic acid comprises introducing to a sample a forward primer, a reverse primer, and a junction probe and performing PCR according to procedures known to those of ordinary skill in the art. In some embodiments, the forward primer is NuAf, the reverse primer is LTR-rev, and the junction probe comprises the sequence of SEQ ID NO: 14. In some embodiments, 45-50 cycles of PCR are conducted. In some embodiments, the PCR method is real-time PCR or quantitative real-time PCR. In some embodiments, the nucleic acid is RNA and the RNA is first converted to cDNA. In some embodiments, the nucleic acid is RNA and either reverse-transcriptase PCR or quantitative reverse-transcriptase PCR is utilized.

General Multiplex Assay Methodology

In another aspect of the present disclosure is a multiplex method of detecting and/or quantifying a lentiviral nucleic acid and an HIV nucleic in a sample. In some embodiments, the multiplex method takes place in a single reaction system or chamber (hereinafter "reaction tube"). In other embodiments, the multiplex method takes place in separate reaction tubes. In some embodiments, the lentiviral nucleic acid is a lentiviral transgene. In some embodiments, the HIV nucleic acid is proviral DNA. In some embodiments, the lentiviral nucleic acid and/or the HIV nucleic acid are RNA, and the RNA is first converted (e.g. via a reverse transcription process) to cDNA prior to amplification.

In some embodiments, the multiplex method utilizes forward primers capable of hybridizing to sequences within the U3 regions of the 3'LTR of the lentiviral vector and/or HIV. In some embodiments, the multiplex method utilizes reverse primers capable of hybridizing to sequences within the R regions of the 3'LTR of the lentiviral vector and/or HIV. In some embodiments, the multiplex method utilizes the same forward and reverse primers for both the amplification of the lentiviral nucleic acid and for the amplification of the HIV nucleic acid. In these cases, the skilled artisan will be able to select a forward primer capable of hybridizing to the same sequence within the U3 region of both wild-type HIV nucleic acid and the lentiviral vector nucleic acid. In other embodiments, the multiplex method utilizes different forward primers, but the same reverse primers. In some embodiments, the forward primers are selected from a NuAf primer and a TATA primer. In some embodiments, the reverse primer is a LTR-rev primer.

In some embodiments, a first probe specific for the lentiviral nucleic acid is employed in a PCR process (e.g. a real-time PCR process) to amplify and/or quantify an amount of lentiviral nucleic acid, and a second probe specific for HIV is employed in a PCR process to amplify and/or quantify an amount of an HIV nucleic acid, wherein the first and second probes comprise different detectable moieties. In some embodiments, the first probe is one capable of hybridizing to a sequence within the 3'LTR of the lentiviral vector but not to a sequence within the 3'LTR of wild-type HIV. In some embodiments, the first probe is optimized for sequence deletions in the 3'LTR of a lentiviral vector nucleic acid as compared with the wild-type 3'LTR sequence.

In some embodiments, the first probe is a junction probe specific to a 3'LTR of the lentiviral vector, e.g. a junction site within the 3'LTR. In some embodiments, the junction probe is one which is capable of hybridizing to at least a portion of a sequence within the U3 region of the lentiviral vector and capable of hybridizing to at least a portion of a sequence within the R region of the lentiviral vector. In some embodiments, the junction probe comprises a first portion capable of hybridizing to a first sequence having at least 90% identity to that of SEQ ID NO: 12; and a second portion capable of hybridizing to the sequence of SEQ ID NO: 13.

In some embodiments, the second probe is selected from a TATA probe or a TAR-probe.

In some embodiments, the amplification of the lentiviral nucleic acid and HIV nucleic acid comprises quantifying an amount of the amplified nucleic acids, such as by detecting signals corresponding to different fluorescent reporters conjugated to the probes employed. In other embodiments, an amount of a lentiviral nucleic acid amplicon and an amount of an HIV nucleic acid amplicon is quantified following electrophoretic separation of the lentiviral nucleic acid amplicons and HIV nucleic acid amplicons.

In some embodiments, the multiplex methods comprise determining a ratio of an amount of a lentiviral nucleic acid to an amount of an HIV nucleic acid present in a sample. In some embodiments, the determined ratio is used to assess the efficacy of treatment or gene therapy, such as with stem cells transduced with a lentiviral vector. In some embodiments, the quantities of lentiviral and HIV nucleic acids may be determined over a course of treatment, i.e. over several different time points to assess the therapeutic efficacy of the treatment (where, for example, a first assessment time point and a second assessment time point may be compared, where an increased amount of lentiviral nucleic acid compared to HIV nucleic acid from the first assessment time point to the second assessment time point is indicative of therapeutic efficiency). In some embodiments, additional treatment is administered depending on the assessment provided.

Multiplex "Method 1"

Figure 2:
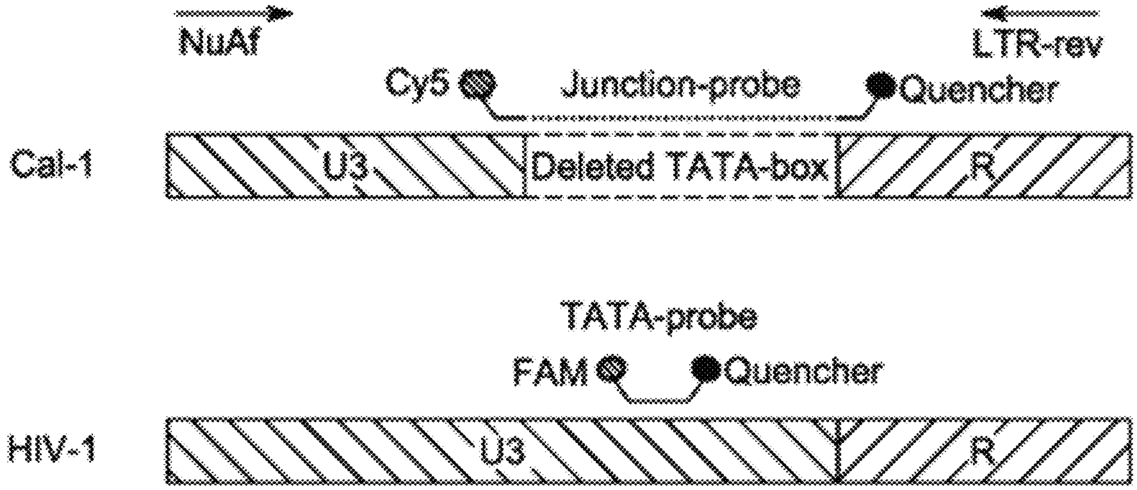
FIG. 2 illustrates an alignment of the Cal-1 U3 region and HIV-1(HXB2) and the location of primers and probes, according to a multiplexed "Method-1" as disclosed herein. Notably, the Cy5 labelled probe is designed to the unique junction sites of the U3 and R regions of the Cal-1 construct, which is not present in HIV-1; the FAM labelled probe if designed to the TATA-box region in HIV-1, which is not present in Cal-1.

With reference to FIG. 2, in one aspect of the present disclosure is a multiplex method of detecting and/or quantifying a lentiviral nucleic acid and a HIV nucleic acid in a sample and in the same reaction tube ("Method 1"). In some embodiments, the method first comprises preparing nucleic acids present in a sample, i.e. DNA or RNA, for amplification. If RNA is the starting material within the sample, then the RNA is converted to cNDA, according to means know to those of ordinary skill in the art.

Once the nucleic acids are prepared, forward and reverse primers are introduced to the sample. In this particular method, the same forward and reverse primers are used for amplification of both the lentiviral nucleic acid and the HIV nucleic acid (see FIG. 2). In some embodiments, the forward primer is a NuAf primer. In some embodiments, the forward primer has the sequence of SEQ ID NO: 2. In some embodiments, the reverse primer hybridizes to a sequence within the R region of the 3'LTR of both the lentiviral nucleic acid and the HIV nucleic acid. In some embodiments, the reverse primer is a LTR-rev primer. In some embodiments, the reverse primer has the sequence of SEQ ID NO: 6. Without wishing to be bound by any particular theory, it is believed that the specificity of this particular assay method is based on the forward primer. Again, without wishing to be bound by any particular theory, it is believed that, due to the single primer set, amplification efficiency of both the lentiviral nucleic acid and the HIV nucleic acid is the same.

Following introduction of the primers to the sample, two different probes are introduced, where a first probe comprising a first detectable moiety is specific to the lentiviral nucleic acid, and where a second probe comprising a second detectable moiety is specific to the HIV nucleic acid (see FIG. 2). In some embodiments, the first probe specific to the lentiviral nucleic acid is optimized for the deletions within the U3 region of the 3'LTR of the lentiviral vector as compared with a wild-type HIV nucleic acid (such that the first probe may hybridize to the lentiviral nucleic acid but not to the HIV nucleic acid). In some embodiments, the probe is a junction probe specific to a junction site within the 3'LTR of the lentiviral nucleic acid, e.g. a junction site that spans a U3 and R region of a 3'LTR. In some embodiments, the junction probe is capable of hybridizing to first region within the 3'LTR and to a second region within the 3'LTR. In some embodiments, the junction probe is capable of hybridizing to a portion or a fragment of a nucleotide sequence within an U3 region of the 3'LTR; and to a portion or a fragment of a nucleotide sequence within a R region of the 3'LTR. In some embodiments, the junction probe comprises a first portion capable of hybridizing to a first sequence having at least 90% identity to that of SEQ ID NO: 12; and a second portion capable of hybridizing to the sequence of SEQ ID NO: 13. In some embodiments, the junction probe comprises a sequence having at least 80% identify to that of SEQ ID NO: 14. In other embodiments, the junction probe comprises a sequence having at least 90% identify to that of SEQ ID NO: 14. In yet other embodiments, the junction probe comprises a sequence having at least 95% identify to that of SEQ ID NO: 14.

In some embodiments, the second probe specific to the HIV nucleic acid is a TATA-probe. In some embodiments, the second probe has the sequence of SEQ ID NO: 10 or a sequence having at least 90% identity to that of SEQ ID NO: 10. In some embodiments, the first probe is labeled with Cy5. In some embodiments, the second probe is labeled with FAM.

Following introduction of the probes, amplification according to standard protocols is allowed to take place. In some embodiments, between about 45 and about 50 PCR cycles are allowed to take place. In some embodiments, the PCR is real-time PCR. Where RNA is a starting material, and as an alternative to first converting the RNA to cDNA, reverse-transcriptase PCR or real-time reverse transcriptase may be utilized.

In some embodiments, the amounts of lentiviral nucleic acid and HIV nucleic acid are quantified, such as by detecting signals from the different detectable moieties conjugated to the different probes. In some embodiments, a ratio of an amount of a lentiviral nucleic acid to an amount of an HIV nucleic acid. In some embodiments, the determined ratio is used to assess the efficacy of treatment or gene therapy, such as with stem cells transduced with a lentiviral vector. In some embodiments, the quantities of lentiviral and HIV nucleic acids may be determined over a course of treatment, i.e. over several different time points to assess the therapeutic efficacy of the treatment (where, for example, a first assessment time point and a second assessment time point may be compared, where an increased amount of lentiviral nucleic acid compared to HIV nucleic acid from the first assessment time point to the second assessment time point is indicative of therapeutic efficiency). In some embodiments, additional treatment is administered depending on the assessment provided.

Dual-Tube "Method 2"

Figure 3:
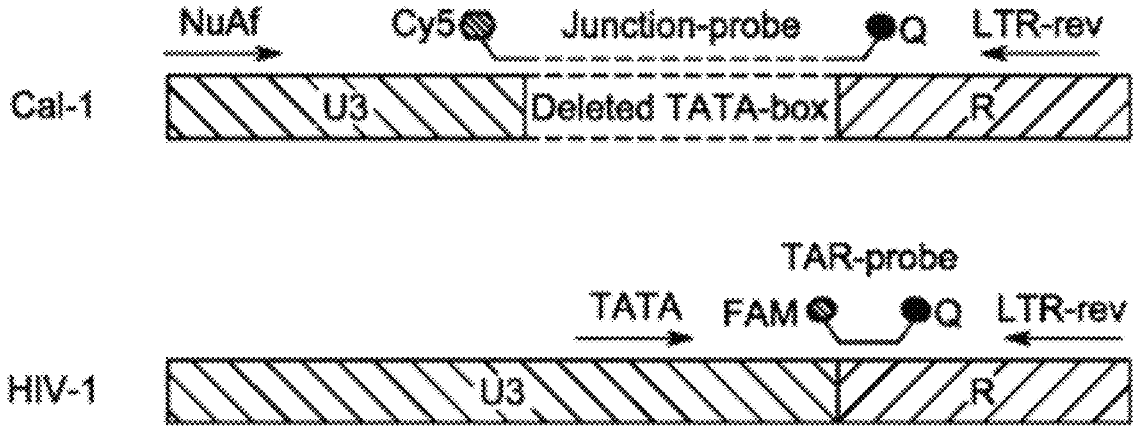
FIG. 3 illustrates an alignment of the Cal-1 U3 region and HIV-1(HXB2) and the location of primers and probes, according to a dual-tubed "Method-2" as disclosed herein. Notably, the forward primer (NUAf) and reverse primer (LTR-rev) is able to amplify Cal-1; and the Cy5 labelled probe is designed to a unique junction site of the U3 and R regions of the Cal-1 construct, which is not present in HIV-1. Likewise, the forward primer (TATA) and LTR-rev primer is able to amply only HIV-1; the FAM labelled probe is able to amplify HIV sequences.

With reference to FIG. 3, in one aspect of the present disclosure is a multiplex method of detecting and/or quantifying a lentiviral nucleic acid and a HIV nucleic acid in a sample, where the multiplex method takes place in two separate reaction tubes ("Method 2"). A first reaction tube comprises all of the components necessary for amplification of a lentiviral nucleic acid. A second reaction tube comprises all of the components necessary for amplification of a HIV nucleic acid. Like the "Method 1" described above, this assay again exploits the difference between the 3'LTR lentiviral nucleic acid structure and the wild-type 3'LTR HIV nucleic acid structure and, in particular, utilizes the TATA-box as an amplification start site for the HIV nucleic acid.

As with the earlier method, the method first comprises preparing nucleic acids present in a sample, i.e. DNA or RNA, for amplification. If RNA is the starting material within the sample, then the RNA is converted to cNDA. Once the nucleic acids are prepared, forward and reverse primers are introduced. In this particular method, different forward primers are used in the amplification of both the lentiviral nucleic acid and the HIV nucleic acid (see FIG. 3). For amplification of the lentiviral nucleic acid, the forward primer is a NuAf primer. In some embodiments, the forward primer has the sequence of SEQ ID NO: 2. For amplification of the HIV nucleic acid, the forward primer is a TATA primer. In some embodiments, the forward primer has the sequence of SEQ ID NO: 4.

In some embodiments, the same reverse primer is used in the amplification of both the lentiviral nucleic acid and the HIV nucleic acid. In some embodiments, the reverse primer hybridizes to a sequence within the R region of the 3'LTR of both the lentiviral nucleic acid and the HIV nucleic acid. In some embodiments, the reverse primer is a LTR-rev primer. In some embodiments, the reverse primer has the sequence of SEQ ID NO: 6. Without wishing to be bound by any particular theory, it is believed that the specificity of this particular assay method is based on the forward primer. Again, without wishing to be bound by any particular theory, it is believed that, due to the single primer set, amplification efficiency of both the lentiviral nucleic acid and the HIV nucleic acid is the same.

Without wishing to be bound by any particular theory, it is believed that the specificity of the reaction in the first reaction tube (amplification of the lentiviral vector nucleic acid) is based upon the specific probe being utilized. Without wishing to be bound by any particular theory, it is believed that the specificity of the reaction in the second reaction tube (amplification of the HIV nucleic acid) is based upon the forward primer utilizes. Again, without wishing to be bound by any particular theory, it is believed that since these assays are based on a common reverse primer (e.g. LTR-rev), and the position of the forward primer is separated within a few hundred bases, amplification efficiency is relatively identical such that the assay may provide reliable, comparative data in both LV nucleic acid and HIV nucleic acid detection and/or quantification.

Following introduction of the primers to the sample, two different probes are introduced, where a first probe comprising a first detectable moiety is specific to the lentiviral nucleic acid, and where a second probe comprising a second detectable moiety is specific to the HIV nucleic acid (see FIG. 3). In some embodiments, the first probe specific to the lentiviral nucleic acid is optimized for the deletions within the U3 region of the 3'LTR of the lentiviral vector as compared with a wild-type HIV nucleic acid (such that the first probe may hybridize to the lentiviral nucleic acid but not to the HIV nucleic acid). In some embodiments, the probe is a junction probe specific to a junction site within the 3'LTR of the lentiviral nucleic acid, e.g. a junction site that spans a U3 and R region of a 3'LTR. In some embodiments, the junction probe is capable of hybridizing to first region within the 3'LTR and to a second region within the 3'LTR. In some embodiments, the junction probe is capable of hybridizing to a portion or a fragment of a nucleotide sequence within an U3 region of the 3'LTR; and to a portion or a fragment of a nucleotide sequence within a R region of the 3'LTR. In some embodiments, the junction probe comprises a first portion capable of hybridizing to a first sequence having at least 90% identity to that of SEQ ID NO: 12; and a second portion capable of hybridizing to the sequence of SEQ ID NO: 13. In some embodiments, the junction probe comprises a sequence having at least 80% identify to that of SEQ ID NO: 14. In other embodiments, the junction probe comprises a sequence having at least 90% identify to that of SEQ ID NO: 14. In yet other embodiments, the junction probe comprises a sequence having at least 95% identify to that of SEQ ID NO: 14.

In some embodiments, the second probe specific to the HIV nucleic acid is a TAR-probe. In some embodiments, the second probe has the sequence of SEQ ID NO: 8, or at least 90% identity to a sequence of SEQ ID NO: 8. In some embodiments, the first probe is labeled with Cy5. In some embodiments, the second probe is labeled with FAM.

Following introduction of the probes, amplification according to standard protocols is allowed to take place. In some embodiments, between about 45 and about 50 PCR cycles are allowed to take place. In some embodiments, the PCR is real-time PCR. Where RNA is a starting material, and as an alternative to first converting the RNA to cDNA, reverse-transcriptase PCR or real-time reverse transcriptase may be utilized.

In some embodiments, the amounts of lentiviral nucleic acid and HIV nucleic acid are quantified, such as by detecting signals from the different detectable moieties conjugated to the different probes. In some embodiments, a ratio of an amount of a lentiviral nucleic acid to an amount of an HIV nucleic acid. In some embodiments, the determined ratio is used to assess the efficacy of treatment or gene therapy, such as with stem cells transduced with a lentiviral vector. In some embodiments, the quantities of lentiviral and HIV nucleic acids may be determined over a course of treatment, i.e. over several different time points to assess the therapeutic efficacy of the treatment (where, for example, a first assessment time point and a second assessment time point may be compared, where an increased amount of lentiviral nucleic acid compared to HIV nucleic acid from the first assessment time point to the second assessment time point is indicative of therapeutic efficiency). In some embodiments, additional treatment is administered depending on the assessment provided.

Multiplex “Method 3”

Figure 4:
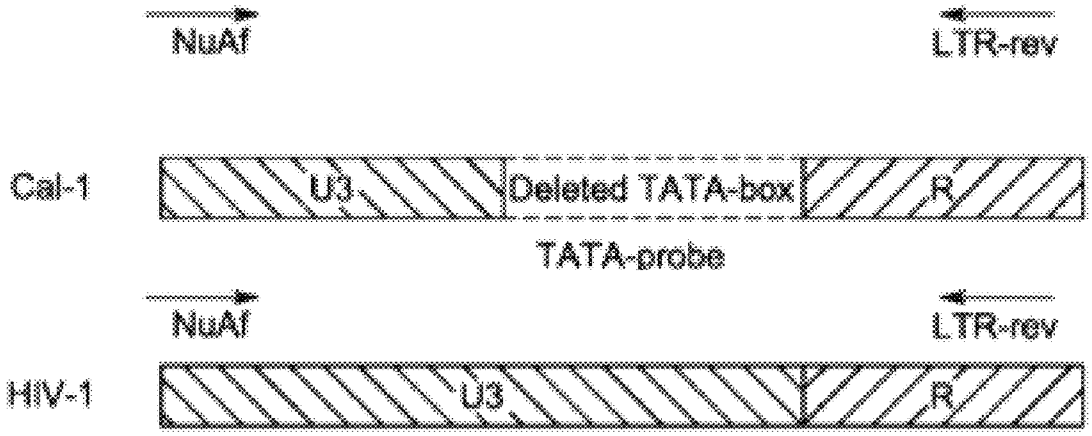
FIG. 4 illustrates an alignment of the Cal-1 U3 region and HIV-1(HXB2) and the location of primers and probes, according to a Multiplexed "Method-3" method as disclosed herein. Notably, the forward primer (NUAf) and reverse primer (LTR-rev) are able to amplify both Cal-1 and HIV-1. The PCR amplified band from Cal-1 is shorter than the PCR amplified band from HIV-1. The quantification of the differently sized amplicons enables generation of data relating to the copy number of the Cal-1 and HIV-1 within the reaction.

With reference to FIG. 4, in one aspect of the present disclosure is a multiplex method of detecting and/or quantifying a lentiviral nucleic acid and a HIV nucleic acid in a sample, where the multiplex method takes place in a single reaction tube (“Method 3”). In some embodiments, the method first comprises preparing nucleic acids present in a sample, i.e. DNA or RNA, for amplification. If RNA is the starting material within the sample, then the RNA is converted to cNDA.

Once the nucleic acids are prepared, forward and reverse primers are introduced. In this particular method, the same forward and reverse primers are used for amplification of both the lentiviral nucleic acid and the HIV nucleic acid (see FIG. 4). In some embodiments, the forward primer is a NuAf primer. In some embodiments, the forward primer has the sequence of SEQ ID NO: 2. In some embodiments, the reverse primer hybridizes to a sequence within the R region of the 3'LTR of both the lentiviral nucleic acid and the HIV nucleic acid. In some embodiments, the reverse primer is a LTR-rev primer. In some embodiments, the reverse primer has the sequence of SEQ ID NO: 6. In this particular method, and as compared with Method 1 and Method 2 herein, no probes are utilized. Without wishing to be bound by any particular theory, it is believed that because of the single primer set, amplification efficiency of both the LV nucleic acid and the HIV nucleic acid is the same.

Figure 7:
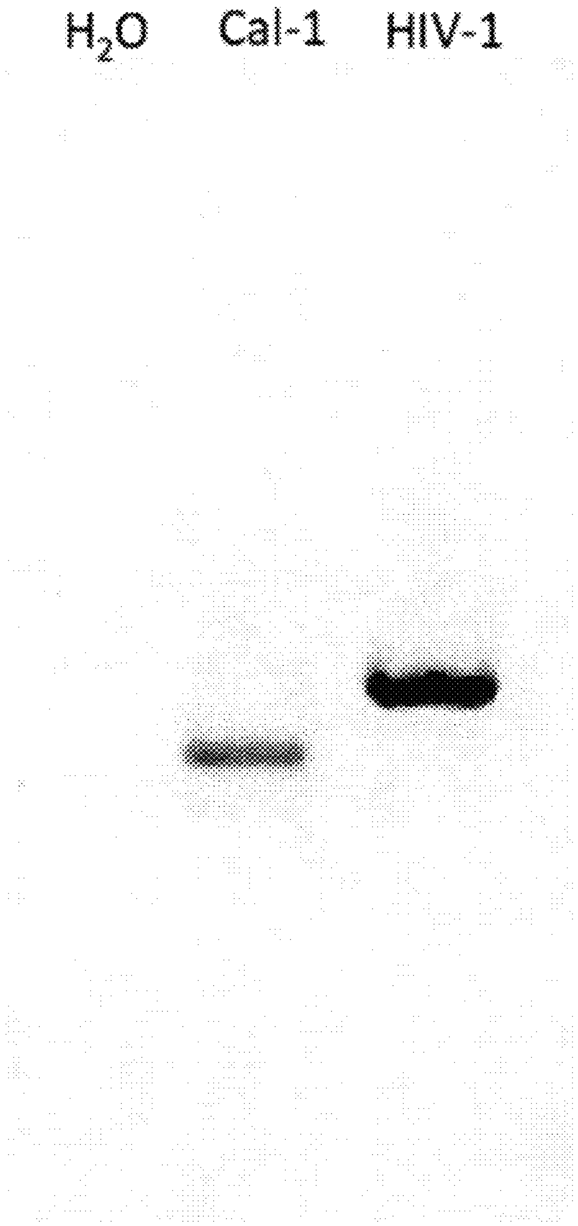
FIG. 7 illustrates the comparative sizes of amplicons from Cal-1 and HIV-1 using a single tube assay in accordance with Method 3, as described herein.

In this method, amplification produces a lentiviral nucleic acid amplicon and a HIV nucleic acid amplicon having different sizes (see FIG. 7, which shows the relative sizes of the amplicons from extracted DNA from Example 1, herein). In some embodiments, the size difference between the two amplicons ranges from between about 100 and about 560 base pairs, with the lentiviral vector amplicon being shorter (i.e. having comparatively less bases or a lower molecular weight) than the HIV amplicon. In other embodiments, the size difference between the two amplicons ranges from between about 100 and about 550 base pairs, with the lentiviral vector amplicon being shorter (i.e. having comparatively less bases or a lower molecular weight) than the HIV amplicon. The different sized amplicons can be distinguished and/or separated from one another by using any standard electrophoretic separation method (e.g. electrophoresis separation with an Agarose gel in conjunction with a DNA staining procedure, such as Sybr-green, EvaGreen). The separated amplicons may then be quantitated such that amounts of lentiviral vector nucleic acid and HIV nucleic in the sample may be derived.

In some embodiments, Droplet Digital PCR (BioRad) may be used to separate the size of the band with EvaGreen dye instantly with accurate quantitative detection and allow for the generation of absolute quantitation of copy number of LV nucleic acid and HIV nucleic acid simultaneously with a simple PCR primer set.

Droplet Digital PCR technology is a digital PCR method utilizing a water-oil emulsion droplet system. Droplets are formed in a water-oil emulsion to form the partitions that separate the template DNA molecules. The droplets serve essentially the same function as individual test tubes or wells in a plate in which the PCR reaction takes place, albeit in a much smaller format. Without wishing to be bound by any particular theory, it is believed that the Droplet Digital PCR System partitions nucleic acid samples into thousands of nanoliter-sized droplets, and PCR amplification is carried out within each droplet.

The droplets support PCR amplification of the template molecules they contain and use reagents and workflows similar to those used in a conventional real time PCR method based on EvaGreen staining od double-stranded DNA. Following PCR, each droplet is analyzed or read in a similar idea as in flow cytometer to determine the fraction of PCR-positive droplets in the original sample. Two amplicon sides are different in LV amplicon and HIV-1 amplicon, when we used in the method described in FIG. 4. The intercalating dyes, EvaGreen, bind to double-stranded DNA. Longer double-stranded DNA amplicon, in case of HIV-1, produce much higher intensity and that generated from shorter double-stranded DNA amplicon, in case of Cal-1. These data are then analyzed using Poisson statistics to determine the target DNA template concentration in the original sample. By this method, we could identify how many copies of HIV-1 and Cal-1 amplicon in the original sample.

Kits

In another aspect of the present disclosure are kits for carrying out the claimed methods. In some embodiments, the kits of the present disclosure provide at least one forward primer, at least one reverse primer, and at least one probe. In some embodiments, the kits of the present disclosure include a NuAf primer, a LTR-rev primer, and a probe specific to a lentiviral vector. In other embodiments, the kits of the present disclosure include a NuAf primer, a LTR-rev primer, and a probe having the sequence of SEQ ID NO: 14. In yet other embodiments, the kits of the present disclosure include a NuAf primer, a LTR-rev primer, a probe specific to a lentiviral vector and a TATA-probe. In further embodiments, the kits of the present disclosure include a NuAf primer, a LTR-rev primer, a probe having the sequence of SEQ ID NO: 14, and a TATA-probe.

In other embodiments, the kits of the present disclosure comprise a NuAf primer, a TATA-primer, a LTR-rev primer, a probe specific to a lentiviral vector, and a TAR-probe. In other embodiments, the kits of the present disclosure comprise a NuAf primer, a TATA-primer, a LTR-rev primer, a probe having SEQ ID NO: 14, and a TAR-probe.

The kits of the present disclosure may further comprise other components including reaction tubes, instructions, buffers, reagents, and oligonucleotides.

EXAMPLES

Disclosed herein are a series of non-limiting examples further illustrating certain embodiments of the present disclosure.

Example 1

Three sets of samples were prepared based on MOLT-4 cells: an initial in-vitro experiments based on MOLT-4 Cells.

a) MOLT-4 cells only without any transduction of Cal-1 lentivirus;

b) 80% of MOLT-4 cells and 20% of MOLT-4 cells with transduction of Cal-1 lentivirus. The degree of transduced cells was determined by flow cytometry analysis of C46 expression. This experimental setting was for determining the transgene effect of a mixture population of original MOLT-4 cells (80%) and Cal-1 transduced MOLT-4 cells (20%);

c) MOLT4 Cal-1 (100%). 100% of Cells are transduced with Cal-1 as determined by C46 expression on Flow cytometry.

Figure 5A:
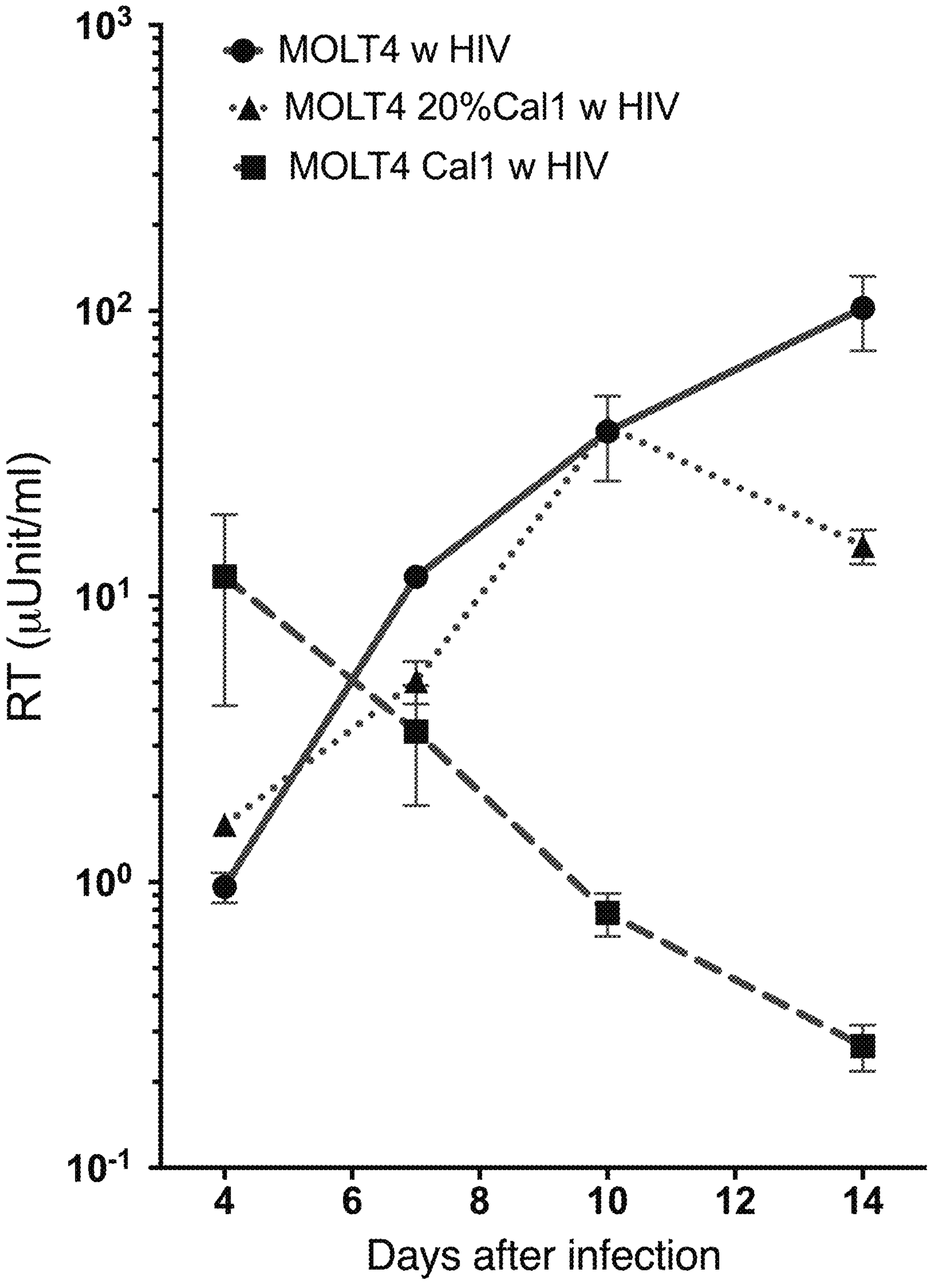
FIGS. 5A, 5B, and 5C provides graphs showing the results of initial in-vitro experiments based on MOLT-4 Cells transduced with lenti-Cal-1 with MOI 2.5.
Figure 5B:
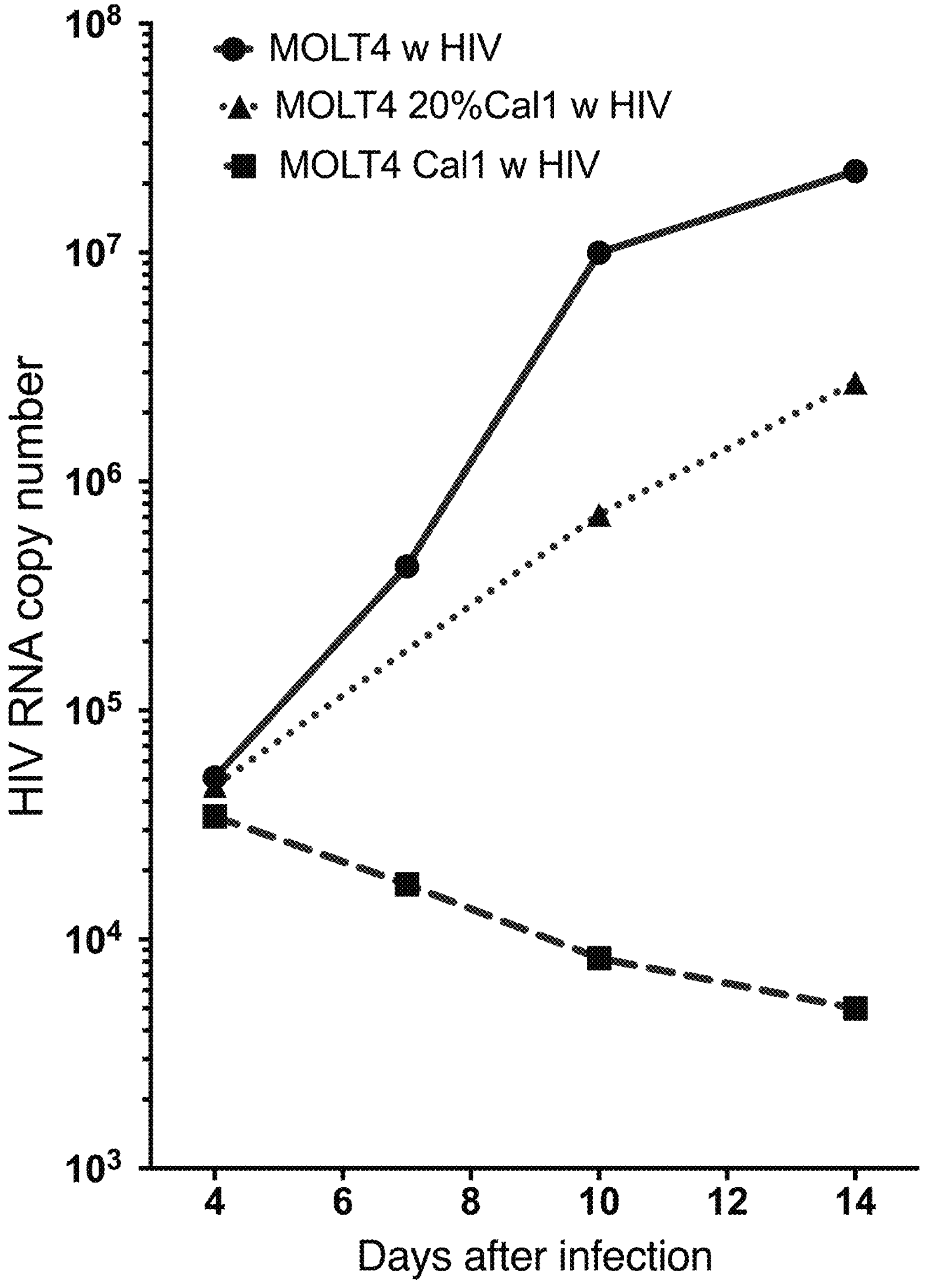

About 0.5 million of these cells were infected with HIV-1 BaL. These cells were cultured in a 25-cm2 culture flask using 10 mL of a standard RPMI-1640 based medium containing 10% FBS with of 1× glutamax supplement in $CO_2$ incubator. Cultured supernatant samples (1 mL) were taken at day 4, 7, 10, 14 for analysis of both RT assay (FIG. 5A) and reverse transcriptase real-time (RT)-PCR assay (FIGS. 5B and C). Cultured cell samples were also prepared at day 4, 7, 10, 14 for analysis of both Intracellular analyses of DNA (FIG. 6AB) and RNA (FIG. 6C). At each time point, 0.6 mL of the cultured cell suspension for DNA analysis and 0.4 mL of the cultured cell suspension for RNA analysis were transferred 2.0 mL of standard Eppendorf tubes. These tubes were centrifuged at 900 g for 3 min. The supernatant was then removed. One mL of PBS was added to each tube, followed by centrifuging at 900 g for 3 min. The supernatant was again removed. The cell pellets were used for RNA and DNA analysis.

Reverse Transcriptase assay (RT assay) (FIG. 5A) was used to measure the amount of lentivirus in 10 μL of culture supernatant released from infected MOLT-4. The RT assay was able to detect HIV-1 and lentivirus vector in the cultured supernatants (see Suzuki K, et al: Poly A-linked non-isotopic microtiter plate reverse transcriptase assay for sensitive detection of clinical human immunodeficiency virus isolates. J Virol Methods 1995, 55:347-356, the disclosure of which is hereby incorporated by reference herein in its entirety).

MOLT-4 (●) showed highly increased RT level on Day 10, Day 14, indicating high production of HIV-1 released from infected MOLT-4 along culture day. This data indicated the infection experiment of this set went very well;

MOLT4 Ca120% (▲) showed a good reduction (10 hold) of HIV-1 released from the infected MOLT-4 on day-14;

MOLT4 Cal-1 (■) showed a great reduction of HIV-1 released from the infected cells;

The RT assay was able to detect RT activity of HIV-1 and the RT assay was also able to detect Cal-1 lentivirus, which was believed to be a carry-over from the process of MOLT-4 transfection. At day-4 analysis, RT activity of MOLT4 Cal-1 (■) was higher than that of MOLT4 (●). RT activity of MOLT4 Ca120% (▲) was also just slightly higher than that of MOLT4 (●).

HIV-1 specific RNA detection (FIG. 5B) was performed based on a single tube assay in accordance with the assay method using a single tube assay in accordance with a Multiplexed Method-1 described herein. RNA was extracted from 500 μL of cultured supernatant using an automated extraction system (EasyMag, bioMerieux) with 60 μL of elution volume setting.

Note: LightCycler 480 (Roche) and the white 96-well plate for LightCycler-480 were used in one step reverse transcriptase real-time (RT)-PCR analysis.

A Master mix per protocol was made for 8 standards and samples analysis.

Master mix: for dual detection detecting HIV-1 RNA and Cal-1 RNA

TABLE 1

A master mix for dual detection of HIV-1 RNA and Cal-1 RNA, where a total volume of the mix was 34 microliters.

| | |
|---|---|
| DNase RNase free water | 10.60 |
| 2 × B (from kit) | 20.00 |
| NuAf (20 μM) | 0.50 |
| Imai-LTR-Rev (20 μM) | 0.50 |
| HIV-1 Tata Probe (5 μM) with FAM label | 0.60 |
| Cal-1 Probe (5 μM) with Cy5 label | 0.60 |
| RT enzyme (from Kit) | 0.40 |
| RNase Inhibitor (from kit) | 0.80 |

Figure 15A:
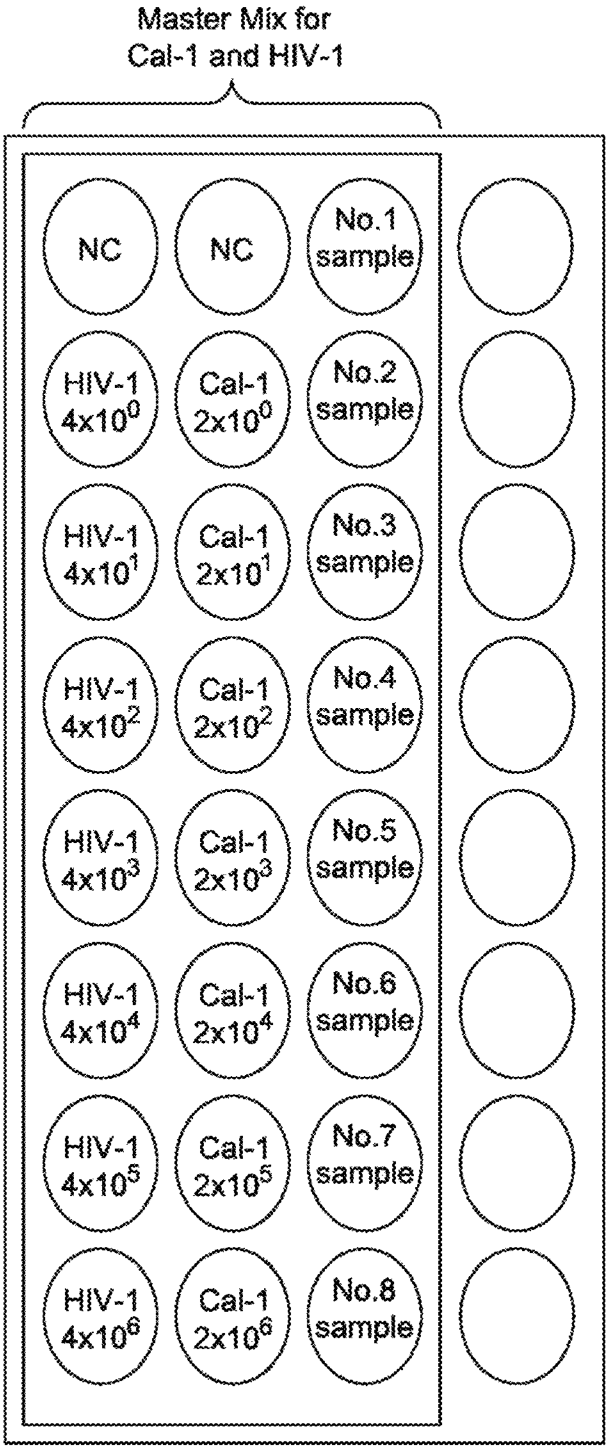
FIGS. 15A through 15E set forth examples of different reagents provided in different wells of 96-well plates.

An aliquot of 34 μL of Master mix was dispensed into the each well of a 96-well plate (see FIG. 15A) of the designed position as in an assay format below. After addition of 6 μL of both HIV-1 and Cal-1 standards and test samples for each well of the designed position, RT-PCR was performed using the following conditions: 45° C.-20 min, 95° C.-2 min 45 cycles of (94° C.-7 sec, 60° C.-30 sec).

Reagents

SensiFAST Probe One step kit (BioLine #BIO-76005)

Standards

HIV-1 standards: 0, 4, 4x10, 4x102, 4x103, 4x104, 4x105, 4x106 copies/μL

Cal-1 standards: 0, 2, 2x10, 2x102, 2x103, 2x104, 2x105, 2x106 copies/μL

HIV-1 specific RNA detection data (FIG. 5B) revealed that at day-4, all three experiments showed the same level of HIV-1 in the RNA extracted from supernatant, using a single tube assay in accordance with Method-1. The amount of HIV-1 in MOLT4 Cal-1 (■) showed a greater than 1000 fold reduction of HIV-1 released from the infected MOLT-4 (●) on day 10 and day 14. MOLT4 Cal20% (▲) showed about a 10 fold reduction of HIV-1 released from the infected MOLT-4 on day-14, which was identical to RT assay data.

Figure 5C:
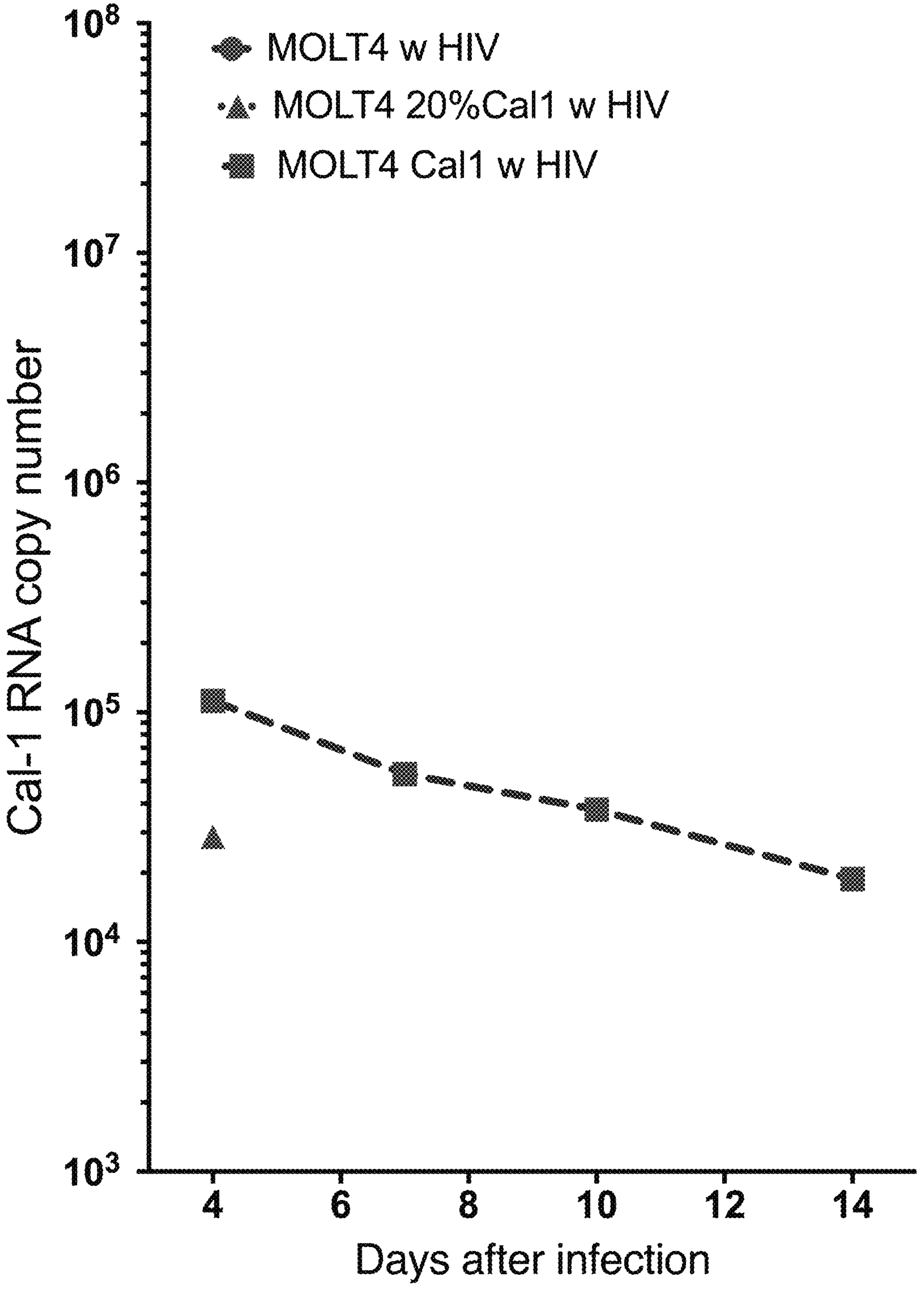

Cal-1 specific RNA detection (FIG. 5C), using a single tube assay in accordance with Method-1, indicated that reduction of Cal-1 RNA level over time in culture was observed in Cal-1 transduced MOLT4 cells (■). The amount of Cal-1 was likely the result of carried-over lentivirus when MOLT-4 cells were transduced with Cal-1 on day-0. There was no detection of Cal-1 RNA in untransduced MOLT-4 cells. Only a small amount of Cal-1 RNA was detected on day 4 from MOLT4 Cal20% (▲) group at day-4.

RT data showed slightly elevated RT levels of MOLT4 Cal-1 (■) as compared to MOLT4 cell alone (●) on day 4. This could have been attributed to lentivirus carry over. A very small level of elevated RT was also observed in MOLT4 Cal20% (▲), compared with MOLT-4 infection. This slightly elevated RT could have been indicative of low level of contribution from lentivirus carry-over. The levels of Cal-1 RNA in the supernatant at day-14 samples was about 1/1000 of HIV-1 RNA level in the cultured supernatant, indicating extremely minor level of Cal-1 RNA carry-over.

Example 2A

HIV-1 integrated DNA (FIG. 6A) and Cal-1 integrated DNA (FIG. 6B) were generated based on a single tube assay in accordance with a Method-1 and as further described herein. DNA was extracted from the cell pellets prepared at day 4, 7, 10, 14 using PurLink Genomic DNA kits (ThermoFisher) with 604, of elution volume.

Note: LightCycler 480 (Roche) and a white 96-well plate for LightCycler-480 were used in this analysis one step real-time PCR analysis.

Two Master mixes per protocol were made for 8 standards and samples analysis.

i) Master mix 1 is for dual detection detecting HIV-1 DNA and Cal-1 DNA ii) Master mix 2 is for Actin detection

TABLE 2

PCR Master 1 mix:
Master mix is for dual detection detecting HIV-1 DNA and Cal-1 DNA.

| | |
|---|---|
| DNase RNase free water | 11.7 |
| 10 × B | 2.0 |
| $MgSO_4$ (5 mM) | 0.8 |
| NuAf (20 μM) | 0.25 |
| Imai-LTR-Rev (20 μM) | 0.25 |
| Tata Probe (5 μM) with FAM label | 0.3 |
| Cal-1 Probe (5 μM) with Cy5 label | 0.3 |
| ACCUPRIME TAQ | 0.4 |

TABLE 3

PCR Master mix 2 is for ACTIN detection.

| | |
|---|---|
| DNase RNase free water | 12.0 |
| 10 × B | 2.0 |
| $MgSO_4$ (5 mM) | 0.8 |
| Actin forward primer (20 μM) | 0.25 |
| Actin forward primer (20 μM) | 0.25 |
| Actin Taq Probe (5 μM) Cy5 label | 0.3 |
| ACCUPRIME TAQ | 0.4 |

Figure 15B:
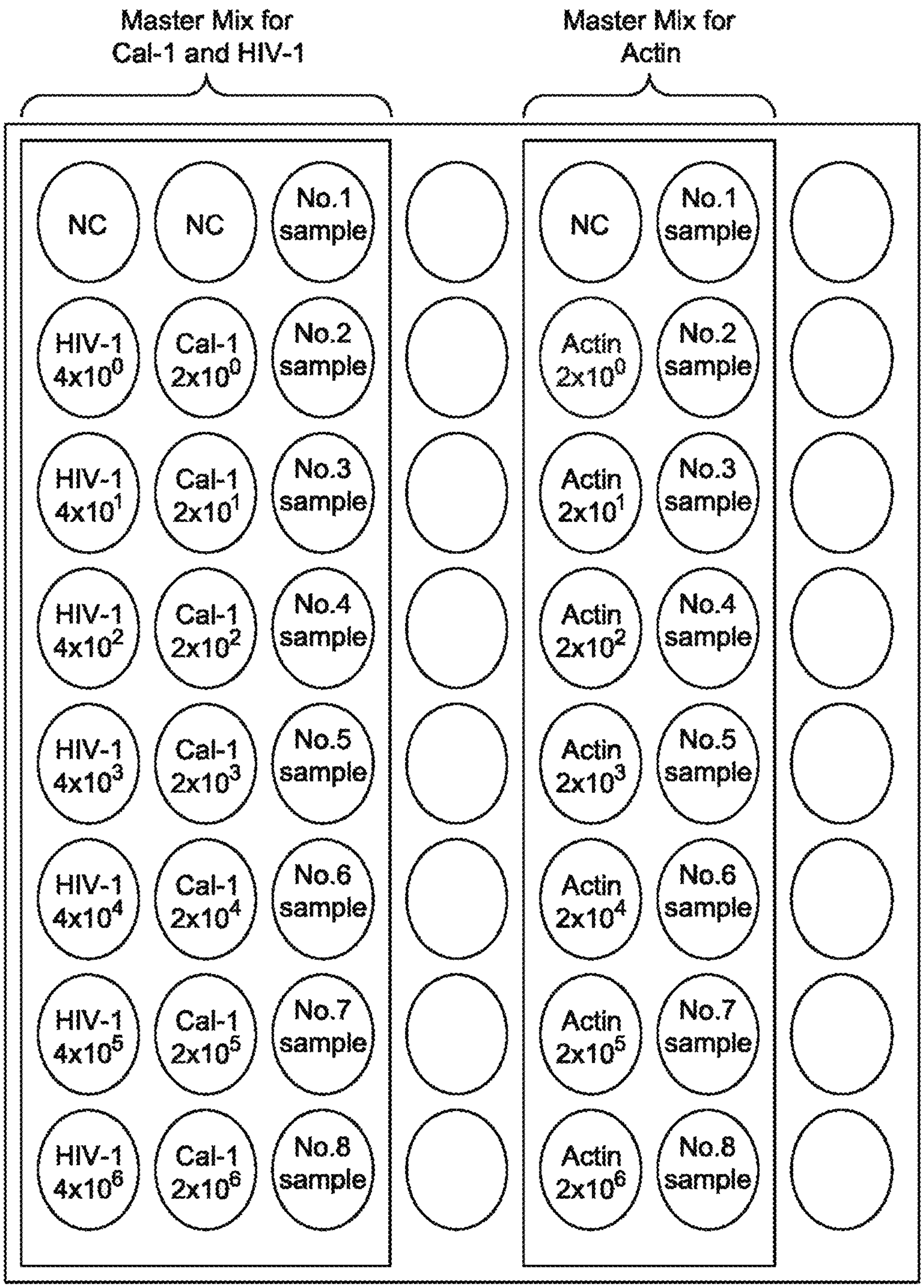

An aliquot of 34 μL of Master mix-1 (HIv-1 and Cal-1 detection) was dispensed into the each well of a 96-well plate of the designed position as in an assay format below and an aliquot of 16 μL of Master 2 mix (Actin detection) was dispensed into each well of a separate 96-well plate as in an assay format below (see FIG. 15B).

After addition of 6 μL of both HIV-1 and Cal-1 standards and test samples for each well of the designed position and 3 μL of Actin standards and test samples for each well of the designed position, PCR was started with the following condition: 95° C.-2 min, 45 cycles of (94° C.-15 sec, 60° C.-30 sec)

Reagents

ACCUPRIME TAQ (Life-Technology #12339016)

Standards

HIV-1 standards: 0, 4, 4x10, 4x102, 4x103, 4x104, 4x105, 4x106 copies/μL

Cal-1 standards: 0, 2, 2x10, 2x102, 2x103, 2x104, 2x105, 2x106 copies/μL

Actin standards: 0, 2, 2x10, 2x102, 2x103, 2x104, 2x105, 2x106 copies/μL

Figure 6A:
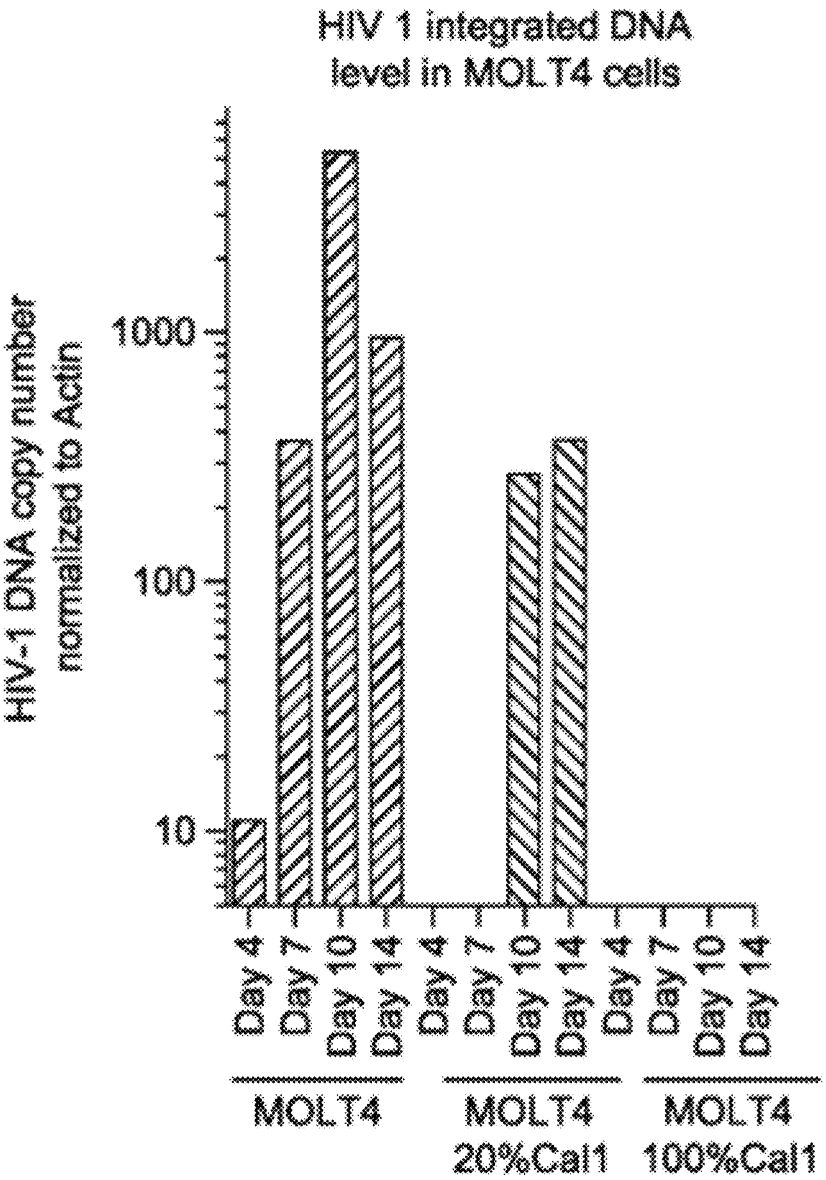
FIGS. 6A, 6B, and 6C provide graphs showing the results of experiments enabling the identification of HIV-1 DNA and Cal-1 DNA copy number using a single tube assay in accordance with a Method 1, as described herein.

HIV-1 integrated DNA data was normalized with 106 copies of GAPDH (FIG. 6A). Significant increase in HIV-1 DNA levels was observed in MOLT4 cells during the culture period. This is indicative of a high level of HIV-1 integration in MOLT4 cells.

MOLT4 Cal-1-20% showed that HIV-1 DNA was detectable on day 10 and day 14. However, the level of HIV-1 DNA was observed to be about 10-50 fold lower as compared to MOLT4 cells alone. HIV-1 DNA was not detected in HIV-challenged Cal-1 100% transduced MOLT4 cells. It is believed that transduced Cal-1 vector protected MOLT-4 cells from HIV-1 infection.

Figure 6B:
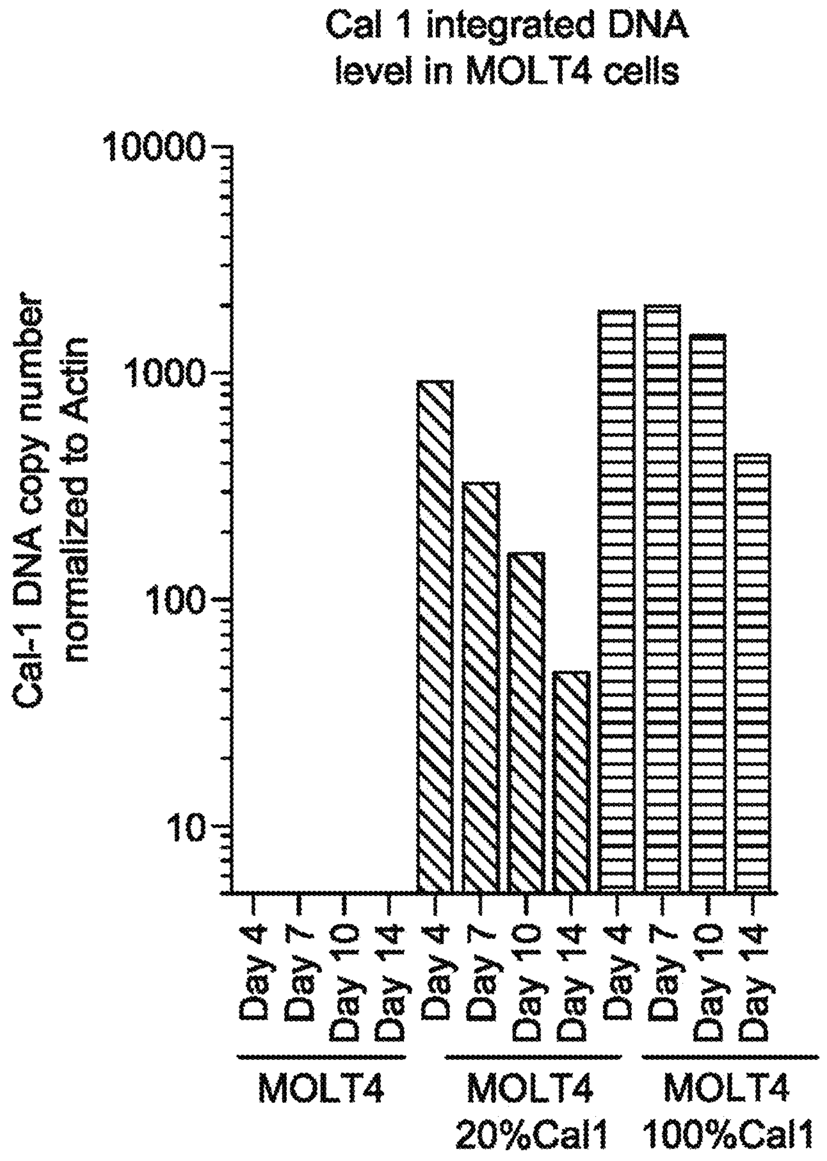
Figure 6C:
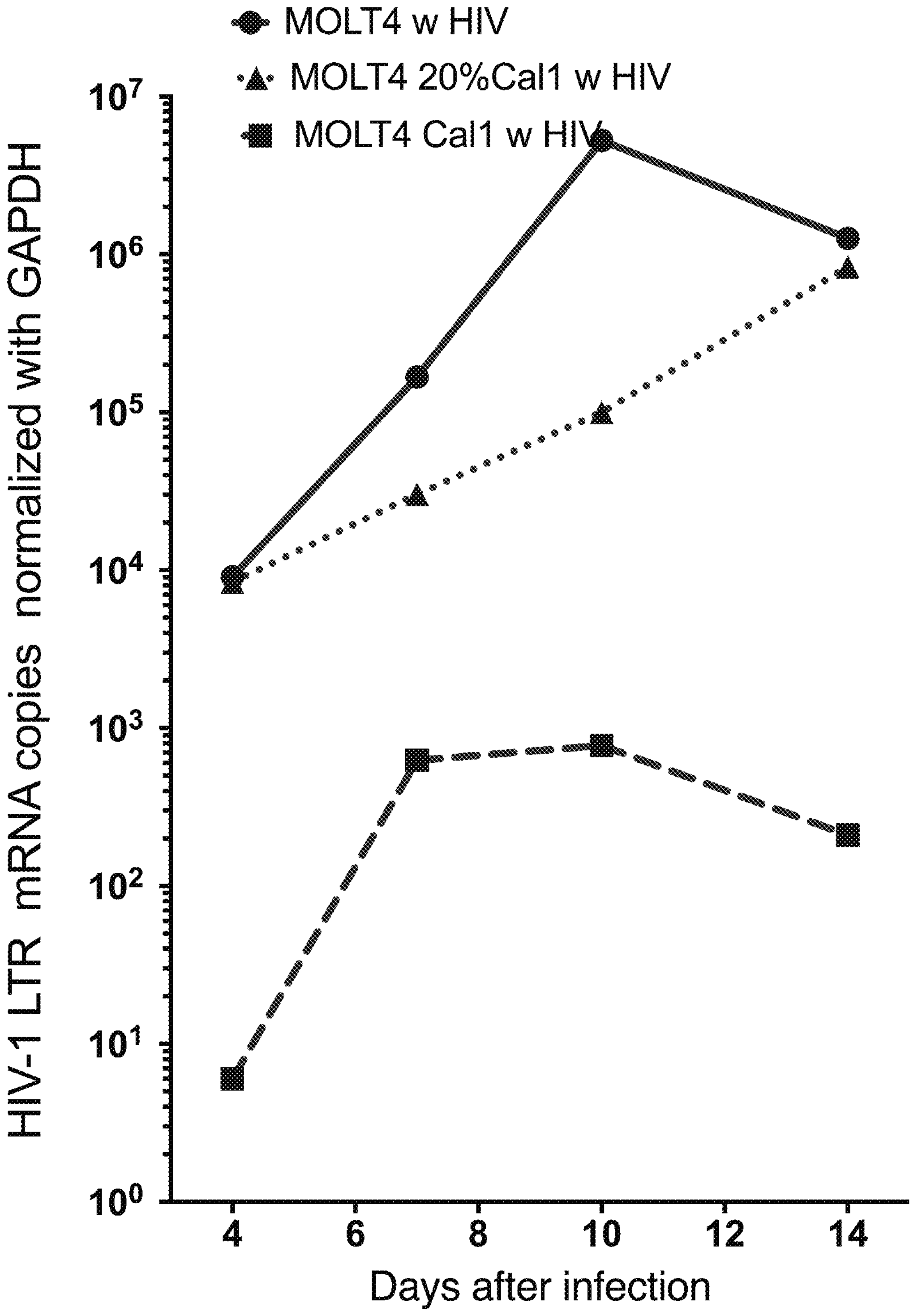

Cal-1 integrated DNA data was normalized with 106 copies of GAPDH (FIG. 6B). A significant increase in Cal-1 DNA levels was observed in Cal-1 100% transduced MOLT4 cells during the culture period. This was indicative of a high level of HIV-1 integration in MOLT4 cells.

MOLT4 Cal-1-20% showed that HIV-1 DNA was detected on day 4 and day 7. However, the level of Cal-1 DNA was observed to be 20-60 fold lower as compared to Cal-1 100% transduced MOLT4 cells. A decreased level of Cal-1 DNA was observed on day 10 and day 14 in MOLT4 Cal-1-20%. This was correlated with HIV-1 DNA data. Because of the loss of Cal-1 DNA with this experimental setting, HIV-1 DNA levels were elevated on day-10 and day 14 (FIG. 6A). Cal-1 DNA was not detected in MOLT4 cells alone. Cal-1

Example 2B

FIG. 6C provide graphs showing the results of experiments enabling the identification of HIV-1 RNA copy number using Method-1. In order to detect HIV-1 intercellular RNA level, HIV-1 specific LTR mRNA was analyzed (FIG. 6C). RNA was extracted from the cell pellets prepared at day 4, 7, 10, 14 using ReliaPrep RNA Miniprep system (Promega) with 60 ul of elution volume.

Note: LightCycler 480 (Roche) and the white 96-well plate for LightCycler-480 were used in this analysis one step reverse transcriptase real-time (RT)-PCR analysis.

A two Master mix per protocol was made for 8 standards and samples analysis.

PCR Master 1 mix: Master mix is for HIV-1 mRNA detection.

PCR Master 2 mix: Master mix is for GAPDH mRNA detection.

TABLE 4

| PCR Master 1 mix is for HIV-1 mRNA detection. | |
|---|---|
| DNase RNase free water | 11.20 |
| 2 × B (from kit) | 20.00 |
| Tata forward primer (20 μM) | 0.50 |
| Imai-LTR-Rev (20 μM) | 0.50 |
| HIV-1 Tata Probe (5 μM) with FAM label | 0.60 |
| RT enzyme (from Kit) | 0.40 |
| RNase Inhibitor (from kit | 0.80 |

TABLE 5

| Master mix 2 is for detection detecting GAPDH mRNA | |
|---|---|
| DNase RNase free water | 5.60 |
| 2 × B (from kit) | 10.00 |
| GAPDH forward primer (20 μM) | 0.25 |
| GAPDH forward primer (20 μM) | 0.25 |
| GAPDH Taq Probe (5 μM) Cy5 label | 0.30 |
| RT enzyme (from Kit) | 0.20 |
| RNase Inhibitor (from kit | 0.40 |

Figure 15C:
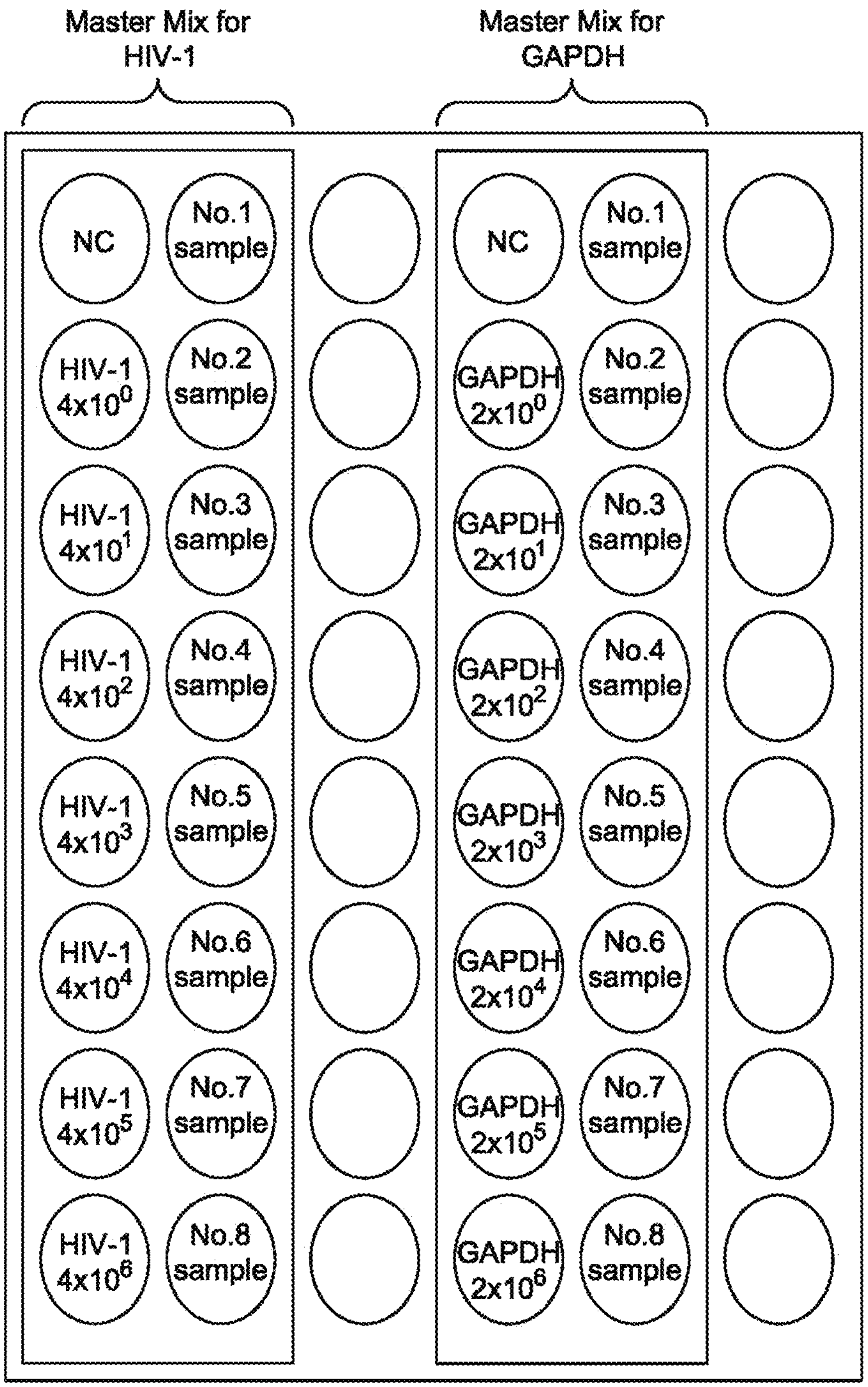

An aliquot of 34 μL of Master mix-1 (HIV-1 detection) was dispensed into the each well of a 96-well plate of the designed position as in an assay format below and an aliquot of 16 μL of Master 2 mix (GAPDH detection) was dispensed into each well of a separate 96-well plate as in an assay format below (see FIG. 15C).

After addition of 6 μL of HIV-1 standards and test samples for each well of the designed position and 3 μL of GAPDH standards and test samples for each well of the designed position. RT-PCR was started with the following condition: 45° C.-20 min, 95° C.-2 min, 45 cycles of (94° C.-7 sec, 60° C.-30 sec)

Reagents

SensiFAST Probe One step kit (BioLine #BIO-76005)

Standards

HIV-1 standards: 0, 4, 4×10, 4×102, 4×103, 4×104, 4×105, 4×106 copies/μL

GAPDH standards: 0, 2, 2×10, 2×102, 2×103, 2×104, 2×105, 2×106 copies/μL

HIV-1 mRNA analysis data was normalized with 106 copies of mRNA expression of GAPDH (FIG. 6C). High levels of HIV-1 specific cell associated HIV-1 LTR mRNA were detected in untransduced MOLT4 cells (●) during the culture period.

On the other hand, a significant reduction (approximately 1000 fold) of HIV-1 cell associated HIV-1 LTR mRNA was observed in Cal-1 100% transduced MOLT4 cells (■) on day 10 and day 14. The level of reduction the MOLT4 Cal-1-20% experimental group (10-100 fold) in HIV-1 cell associated HIV-1 LTR mRNA (▲) was indicative of partial protection from HIV infection at day 10. These observations suggested that Cal-1 was able to induce over 1000 times reduction of HIV infection in MOLT4 cells.

Despite the HIV DNA level not being detected in Cal-1 transduced MOLT4 cells, HIV-1 cell associated LTR-mRNA was still detectable (■), as illustrated in FIG. 6C. This was an indication that a very low level of RNA transcription was taking place from presumably a very small population of HIV-1 integrated DNA in MOLT-4 cells.

The amount of DNA added to each PCR reaction had an estimated cell equivalence of 1-2x10e5 cells. Therefore, the HIV-1 detection sensitivity in this assay method was 2 copies per 1-2x10e5 cells. If the frequency HIV-1 integration was less than 2 copies per 1-2x10e5 cells, the assay could not detect HIV-1 DNA using this assay method.

It was possible that the HIV-1 LTR-mRNA levels observed were the result of a very small fraction of MOLT4 cells, which failed to be transduced with Cal-1.

Example 3

Example 3 illustrates the results of two different assay methods illustrated in FIG. 2 (Method-1) and FIG. 3 (Method-2), where the methods were compared using DNA, obtained from the Example 1, herein. The result in Table 6 utilizes a multiplex assay method, taking place in a single reaction tube (Method-1); whereas the result in Tables 7 and 8 utilizes a multiplex assay method taking place in two separate reaction tubes (Method-2). Based on the data in Tables 6, 7, and 8 both assays perform similarly, i.e. the quantitative data obtained from both methods was similar. Accordingly, both methods, as disclosed herein, are able to amplify a lentiviral nucleic acid and an HIV nucleic acid and quantify levels of amplified lentiviral nucleic acid and amplified HIV nucleic acid.

TABLE 6

Assay using single primer set with both Cy5-labelled Cal-1 and FAM-labelled HIV-1 specific probes in a single PCR tube

| Cy5-labelled Cal-1 data | | | | copy | Normalized Copy number/ 1000 copy |
|---|---|---|---|---|---|
| Well | Fluor | Content | Cq | number/μL | GAPDH |
| A02 | Cy5 | NTC | N/A | N/A | |
| B02 | Cy5 | Cal-1 Std-01 | N/A | 2 | |

TABLE 6-continued

Assay using single primer set with both Cy5-labelled Cal-1 and FAM-labelled HIV-1 specific probes in a single PCR tube

| | | | | | |
|---|---|---|---|---|---|
| C02 | Cy5 | Std-02 | 38.34 | 20 | |
| D02 | Cy5 | Std-03 | 34.2 | 200 | |
| E02 | Cy5 | Std-04 | 29.82 | 2000 | |
| F02 | Cy5 | Std-05 | 27.25 | 20000 | |
| G02 | Cy5 | Std-06 | 25.54 | 200000 | |
| H02 | Cy5 | Std-07 | 18.68 | 2000000 | |
| A04 | Cy5 | MOLT4 only | N/A | N/A | |
| B04 | Cy5 | MOLT4 only | N/A | N/A | |
| C04 | Cy5 | MOLT4 with HIV-1 infection | N/A | N/A | |
| D04 | Cy5 | MOLT4 with HIV-1 infection | N/A | N/A | |
| E04 | Cy5 | MOLT4 withCat1 transduction | 22.85 | 308600 | 48575 |
| F04 | Cy5 | MOLT4 withCat1 transduction | 23.01 | 279000 | 43916 |

FAM-labelled HIV-1 data

| Well | Fluor | Content | Cq | SQ | |
|---|---|---|---|---|---|
| A03 | FAM | NTC | N/A | N/A | |
| B03 | FAM | HIV Std-11 | N/A | 2 | |
| C03 | FAM | Std-12 | 38.67 | 20 | |
| D03 | FAM | Std-13 | 34.67 | 200 | |
| E03 | FAM | Std-14 | 30.64 | 2000 | |
| F03 | FAM | Std-15 | 27.27 | 20000 | |
| G03 | FAM | Std-16 | 23.3 | 200000 | |
| H03 | FAM | Std-17 | 18.17 | 2000000 | |
| A04 | FAM | MOLT4 only | N/A | N/A | |
| B04 | FAM | MOLT4 only | N/A | N/A | |
| C04 | FAM | MOLT4 with HIV-1 infection | 30.67 | 2134 | 818 |
| D04 | FAM | MOLT4 with HIV-1 infection | 29.01 | 2003 | 768 |
| E04 | FAM | MOLT4 withCat1 transduction | N/A | N/A | |
| F04 | FAM | MOLT4 withCat1 transduction | N/A | N/A | |

TABLE 7

Using a single tube of the primer set with a Cy5-labeled Cal-1 specific probe

| Well | Fluor | Content | Cq | copy number/μL | Normalized Copy number/ 1000 copy GAPDH |
|---|---|---|---|---|---|
| A05 | Cy5 | NTC | N/A | N/A | |
| B05 | Cy5 | Std-21 | N/A | 2 | |
| C05 | Cy5 | Std-22 | 37.75 | 20 | |
| D05 | Cy5 | Std-23 | 34.75 | 200 | |
| E05 | Cy5 | Std-24 | 30.23 | 2000 | |
| F05 | Cy5 | Std-25 | 28.18 | 20000 | |
| G05 | Cy5 | Std-26 | 26.06 | 200000 | |
| H05 | Cy5 | Std-27 | 19.83 | 2000000 | |
| A06 | Cy5 | MOLT4 only | N/A | N/A | |
| B06 | Cy5 | MOLT4 only | N/A | N/A | |
| C06 | Cy5 | MOLT4 with HIV-1 infection | N/A | N/A | |
| D06 | Cy5 | MOLT4 with HIV-1 infection | N/A | N/A | |
| E06 | Cy5 | MOLT4 withCat1 transduction | 23.45 | 388000 | 61074 |
| F06 | Cy5 | MOLT4 withCat1 transduction | 23.26 | 441300 | 69463 |

TABLE 8

Reaction using another single tube of the HIV-1 specific primer set with FAM-labelled probe.

| Well | Fluor | Content | Cq | copy number/μL | Normalized Copy No./ 1000 copy GAPDH |
|---|---|---|---|---|---|
| A08 | FAM | NTC | N/A | N/A | |
| B08 | FAM | HIV Std-31 | N/A | 2 | |
| C08 | FAM | Std-32 | 38.65 | 20 | |
| D08 | FAM | Std-33 | 33.86 | 200 | |
| E08 | FAM | Std-34 | 30.13 | 2000 | |
| F08 | FAM | Std-35 | 25.66 | 20000 | |
| G08 | FAM | Std-36 | 21.74 | 200000 | |
| H08 | FAM | Std-37 | 17.61 | 2000000 | |
| A09 | FAM | MOLT4 only | N/A | N/A | |
| B09 | FAM | MOLT4 only | N/A | N/A | |
| C09 | FAM | MOLT4 with HIV-1 infection | 31.35 | 966 | 370 |
| D09 | FAM | MOLT4 with HIV-1 infection | 31.55 | 862 | 331 |
| E09 | FAM | MOLT4 withCat1 transduction | N/A | N/A | |
| F09 | FAM | MOLT4 withCat1 transduction | N/A | N/A | |
| A08 | FAM | NTC | N/A | N/A | |
| B08 | FAM | HIV Std-31 | N/A | 2 | |
| C08 | FAM | Std-32 | 38.65 | 20 | |
| D08 | FAM | Std-33 | 33.86 | 200 | |
| E08 | FAM | Std-34 | 30.13 | 2000 | |
| F08 | FAM | Std-35 | 25.66 | 20000 | |
| G08 | FAM | Std-36 | 21.74 | 200000 | |
| H08 | FAM | Std-37 | 17.61 | 2000000 | |
| A09 | FAM | MOLT4 only | N/A | N/A | |
| B09 | FAM | MOLT4 only | N/A | N/A | |
| C09 | FAM | MOLT4 with HIV-1 infection | 31.35 | 966 | 370 |
| D09 | FAM | MOLT4 with HIV-1 infection | 31.55 | 862 | 331 |
| E09 | FAM | MOLT4 withCat1 transduction | N/A | N/A | |
| F09 | FAM | MOLT4 withCat1 transduction | N/A | N/A | |

Example 4

HIV-1 clinical samples were tested to assess HIV-1 detection sensitivity for the newly developed LTR based assay. In general, the study was conducted to assess the detection sensitivity of the developed HIV-1 assay and to confirm any cross-reactivity to the HIV-1 DNA, clinical HIV-1 patient samples were used. Fourteen HIV-1 clinical samples were tested to assess HIV-1 detection sensitivity. DNA extracted from 1 mL of patients' blood samples with QIAamp DNA Blood Mini kit (Qiagen Cat No. 51104) with elution volume of 60 μL. PCR analysis was done as in the protocol provided in Example 5.

Aims

1) To determine whether the HIV-1 assay is sensitive enough to detect HIV-1 DNA extracted from HIV-1 positive patients with the assay of Method-2.

2) To determine whether the Cal-1 assay is not able to make any cross reaction to the DNA extracted from HIV-1 positive patients.

Preparation of the Samples

Fourteen HIV-1 positive samples were used for the analyses. DNA was extracted from 1 mL of blood (about 0.3-0.7×10e6 CD4+ cells) for analysis of HIV-1 and Cal-1 detection.

Result

HIV-1 and Cal-1 copy numbers were calculated by standards and normalized by 1,000,000 copies of ACTIN DNA.

Figure 9:
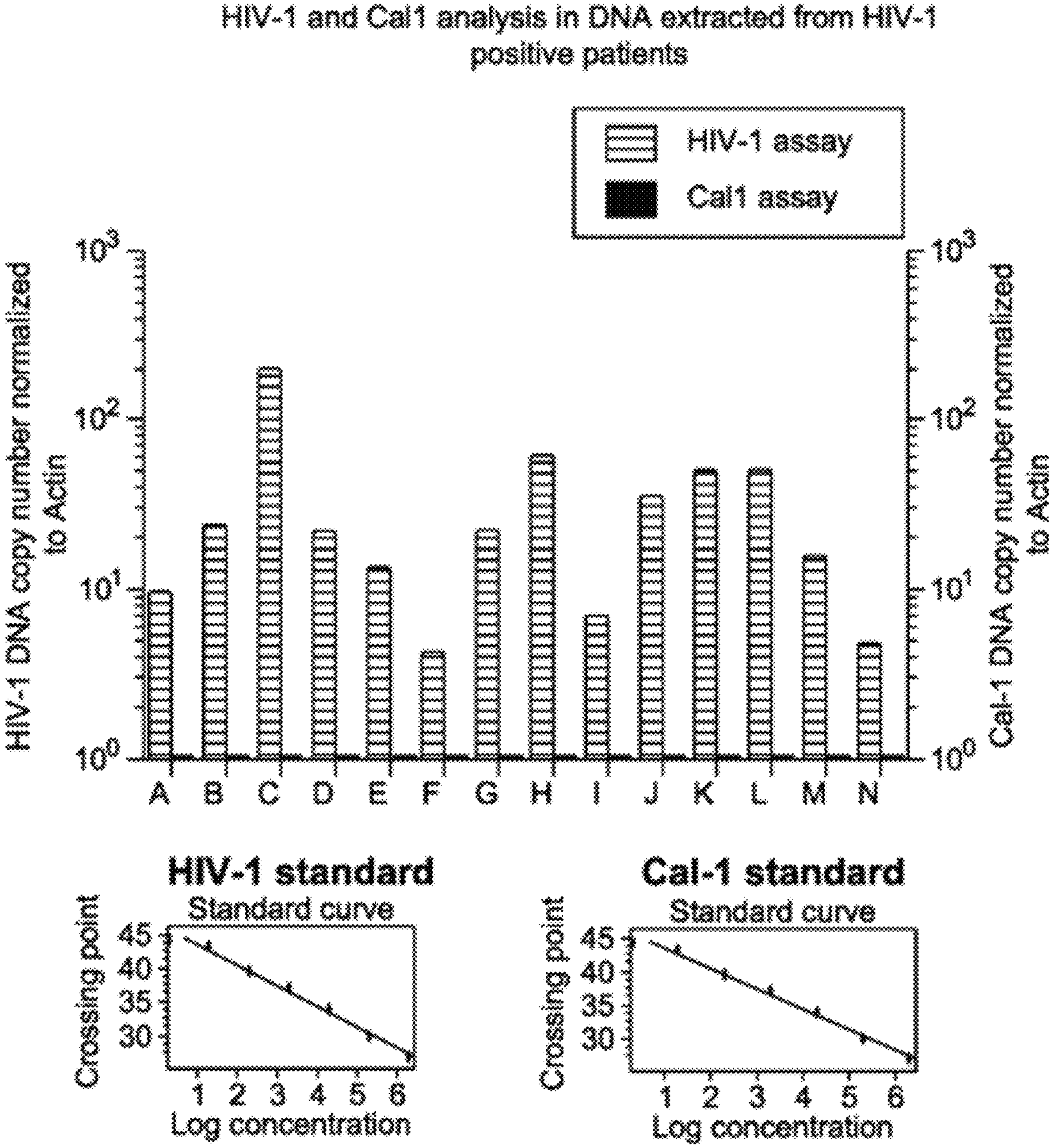
FIG. 9 provide graphs showing the results of experiments enabling identifications HIV-1 DNA copy number using two separate tube assays in accordance Method-2, as described herein FIG. 10A provides a flow analysis of the second in-vitro experiments based on MOLT-4 Cells transduced with lenti-ccr5 and Cal-1 (ccr5 and C46). MOLT-4 Cell were transduced with either with lenti-sh5 and lenti-Cal-1 with MOI 2.5. Transduction was determined after a 48-hour incubation period, utilizing 2F5 staining followed by flowcytometry analysis. Lenti-sh5 transduced MOLT-4 cells indicated a 75% reduction in CCR5 expression. Lenti-Cal-1 indicated a 60% knockdown of CCR5. 72 hours post transduction of lenti-Cal-1, approximately 89% of cells expressed C46 with a 60% reduction in CCR5 expression of transduced MOLT-4 cells.

Both standards generated linear lines, see FIG. 9. Both HIV-1 and Cal-1 assays were valid. HIV-1 DNA assay was able to detect 14 out of 14 samples (A-N samples), indicated in FIG. 9. Cal-1 DNA assay was not detected in any of the 14 samples. Cal-1 assay did not have any cross-reactivity to the DNA extracted from the HIV-1 positive patients. Levels of HIV-1 DNA assay in the clinical samples were in the similar levels obtained with 2 and 20 U1 cells spiked data, indicating the experimental setting in Example 4 herein was at a similar level of to the actual clinical setting.

Example 5

Another experiment was performed based on Example 5, showing the results of the experiment enabling the identification of HIV-1 and Cal-1 DNA copy number two separate tube assays in accordance with Method-2

Three sets of samples were prepared based on ex-vivo CD4+ T cell samples, obtained from singe donor:

a) Untransduced CD4+ T cells b) Transduced CD4 with Cal-1-lenti at MOI-2 (5×106 cells)

c) Transduced CD4 with Cal-1-lenti at MOI-10 (5×106 cells)

The setting-a) is negative control of the experiment. The setting-b) is Cal-1 transduced $CD4^+$ T cells with MOI-2. The setting-c) is Cal-1 transduced $CD4^+$ T cells with MOI-10.

These samples were obtained at day 14 after transduction of the CD4+ T cells with Cal-1-lenti with a standard Cal-1 transduction protocol. On day 14, 5 million cells of three souses of untransduced and transduced CD+ T cells were stored in a vapor phase of liquid nitrogen with cryopreserved manner.

U1 cells were counted. Aliquots of 2, 20, 200, 2000 U1 cells were spiked into the CD4 cells containing 1×106 cells. Another aliquot of $1\times10^6$ cells CD4 cells was used without spiked control (Please note that 5×106 cells of the transduced CD4 were divided into equal amount of five aliquots, containing 1×106 cells per aliquot). DNA was extracted with PurLink Genomic DNA kits (ThermoFisher) with 60 μL of elution volume. Basically we created mimic clinical samples by spiking U1 cells into the above three groups of $CD4^+$ T cells. U1 cell was selected because it is carries two copies of the integrated HIV-1 genome in a single cell. Experimental setting is listed as following:

a) 0, 2, 20, 200, and 2000 U1 cells per $1\times10^6$ of Untransduced CD4+ T cells b) 0, 2, 20, 200, and 2000 U1 cells per $1\times10^6$ of transduced CD4 with Cal-1-lenti at MOI-2 c) 0, 2, 20, 200, and 2000 U1 cells per $1\times10^6$ of transduced CD4 with Cal-1-lenti at MOI-10

HIV-1 integrated DNA (FIG. 8A) and Cal-1 integrated DNA (FIG. 8B) data were obtained using two separate tube assays in accordance with Method-2.

Three Master mixes per protocol were made for 8 standards and samples analysis.

i) Master mix 1 is for detection of HIV-1 DNA (Table 9)

ii) Master mix 2 is for detection of Cal-1 DNA (Table 10)

iii) Master mix 3 is for detection of Actin detection (Table 11)

TABLE 9

| PCR Master mix 1 for detecting HIV-1 DNA, total amounts were 34 microliters. | |
|---|---|
| DNase RNase free water | 12.40 |
| 2 × B (from the kit) | 20.00 |
| Tata forward primer (20 μM) | 0.50 |
| Imai-LTR-Rev (20 μM) | 0.50 |
| TAR Probe (5 μM) with FAM label | 0.60 |

TABLE 10

| PCR Master mix 2 for detecting Cal-1 DNA, total amounts were 34 microliters. | |
|---|---|
| DNase RNase free water | 12.40 |
| 2 × B (from the kit) | 20.00 |
| NuAf (20 μM) | 0.50 |
| Imai-LTR-Rev (20 μM) | 0.50 |
| Cal-1 Probe (5 μM) with Cy5 label | 0.60 |

TABLE 11

| PCR Master 3 mix for detecting actin, total amounts were 17 microliters | |
|---|---|
| DNase RNase free water | 6.20 |
| 2 × B (from the kit) | 10.00 |
| Actin forward primer (20 μM) | 0.25 |
| Actin reverse primer (20 μM) | 0.25 |
| Actin Probe (5 μM) with FAM | 0.30 |

Figure 15D:
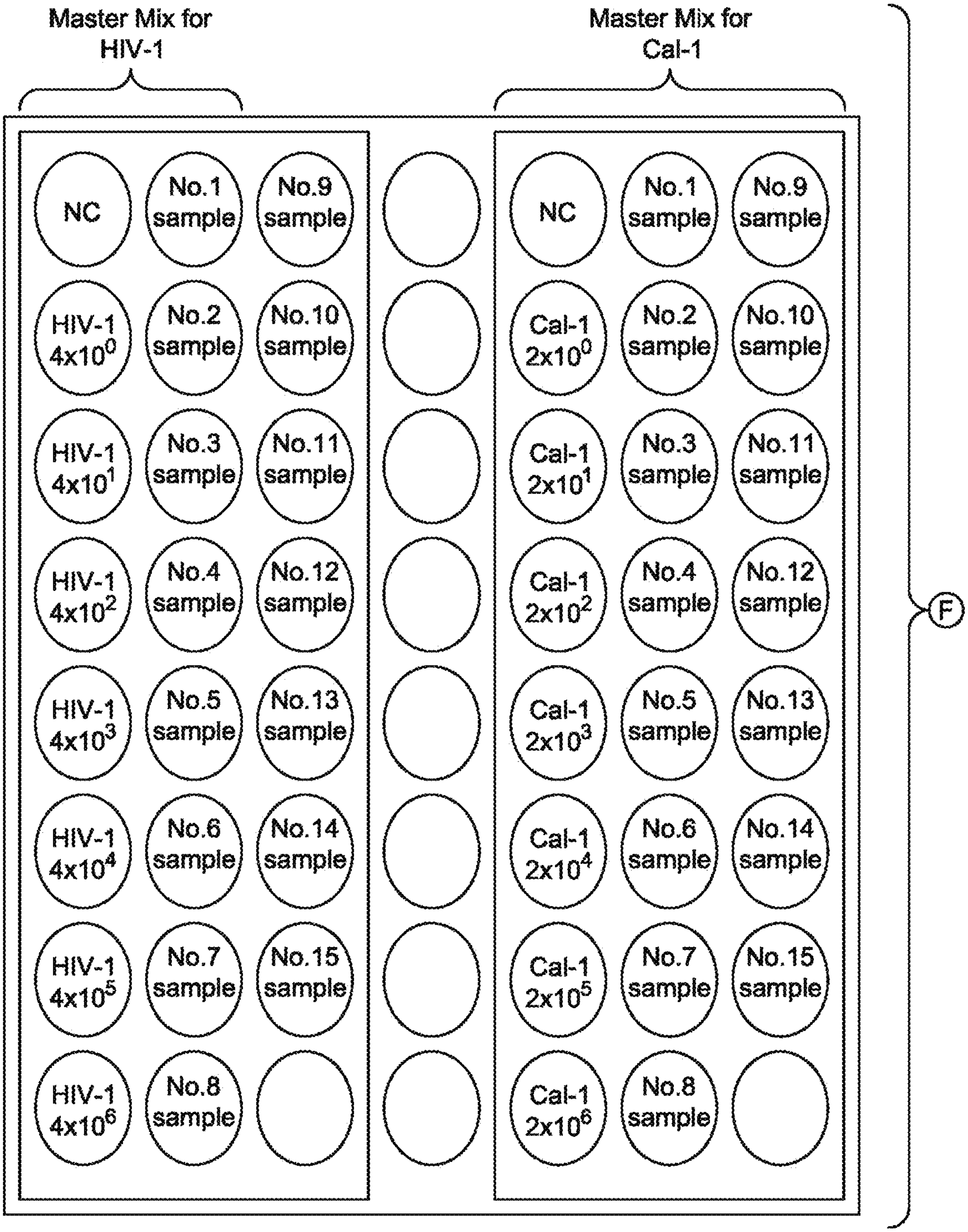
Figure 15E:
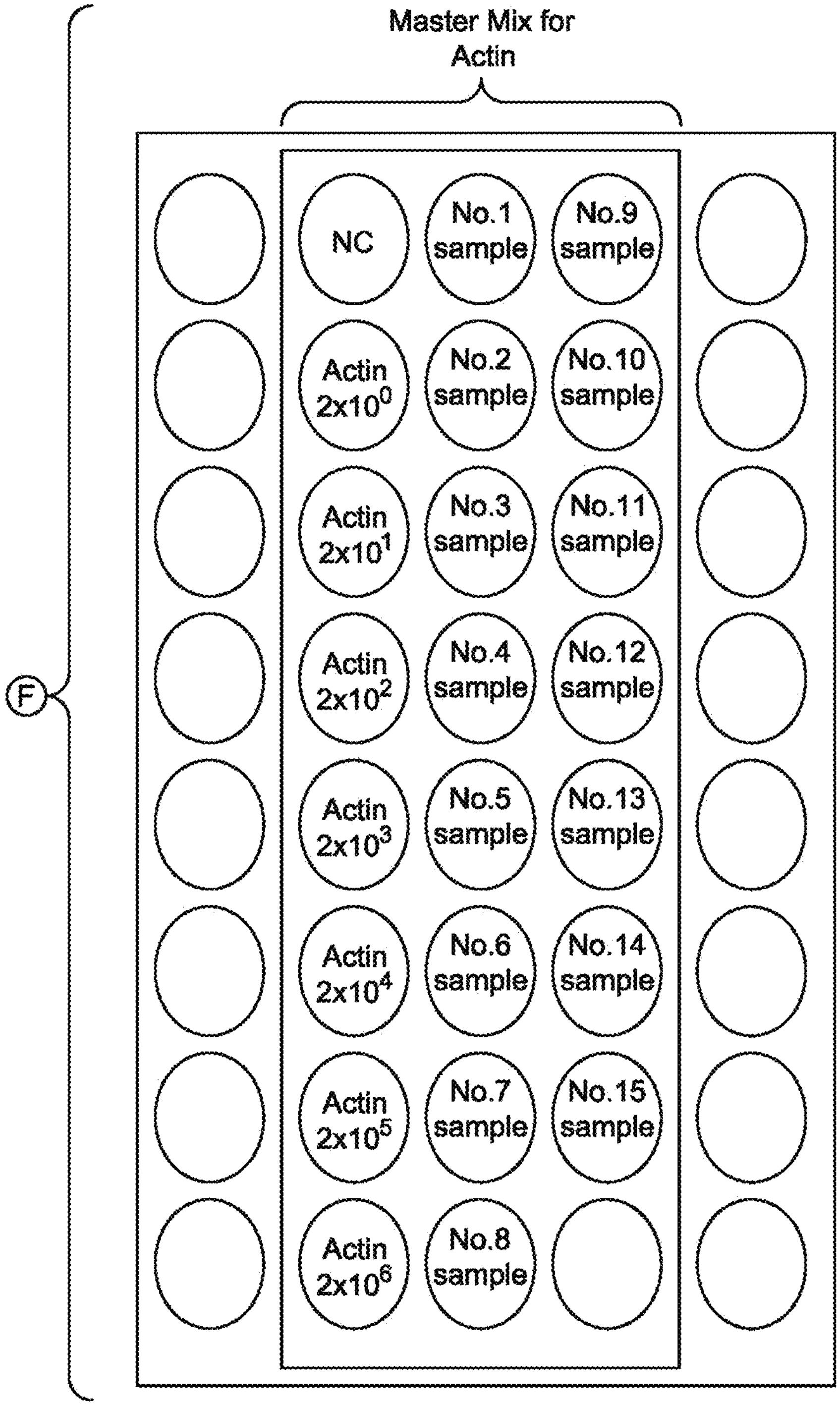
Figure 18A:
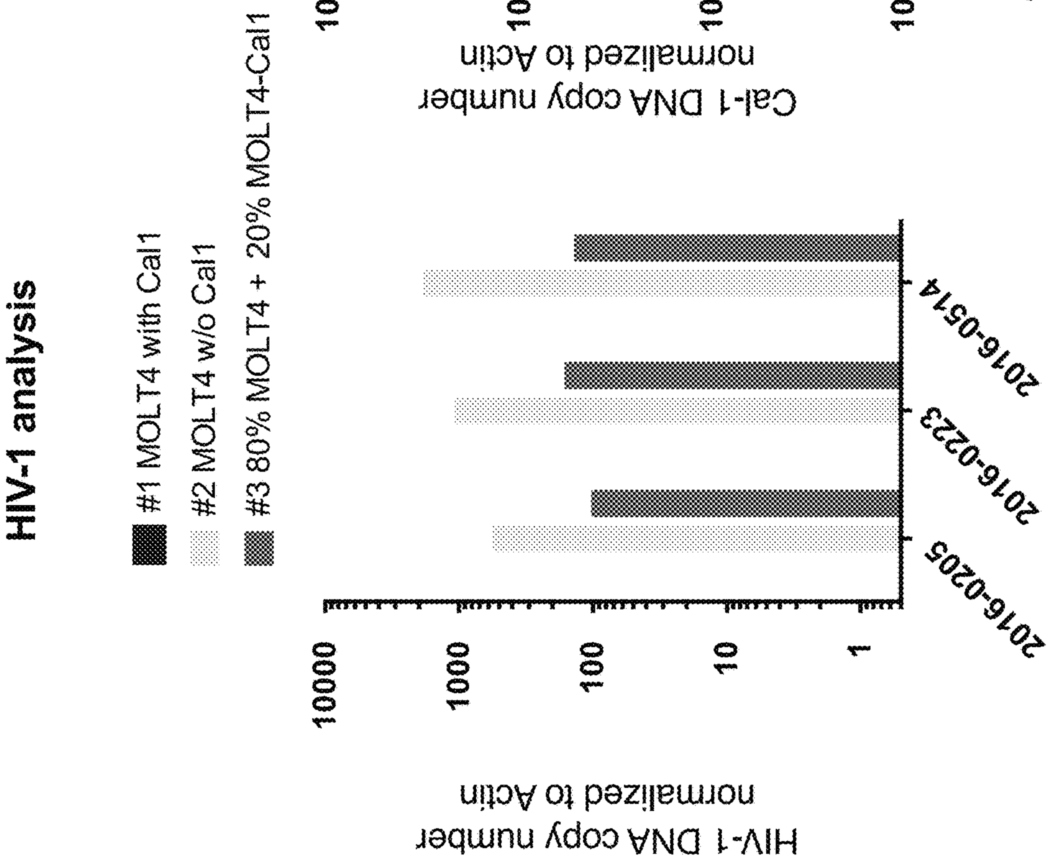
FIGS. 18A and 18B provide HIV-1 DNA copy number or Cal-1 DNA copy number, both normalized to actin.
Figure 18B:
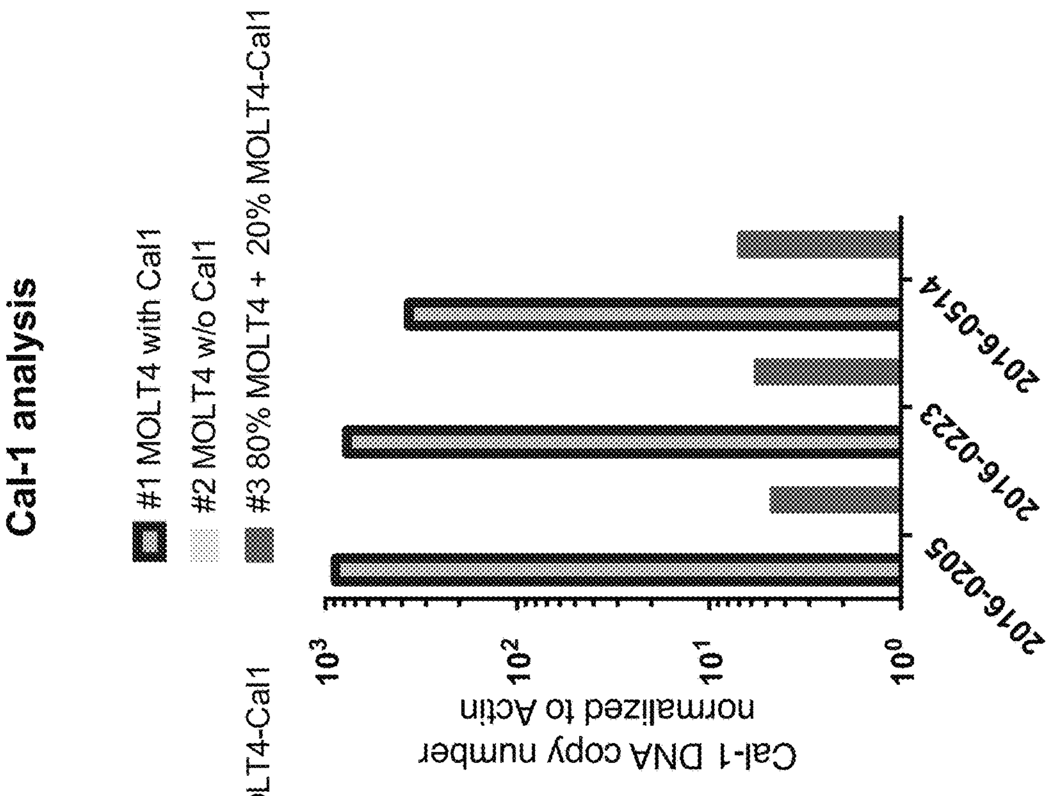

An aliquot of 34 μL of Master mix-1 (HIV-1 detection) and Master mix-2 (Cal-1 detection) was dispensed into the each well of a 96-well plate of the designed position as in an assay format below and an aliquot of 16 μL of Master 3 mix (Actin detection) was dispensed into each well of a separate 96-well plate as in an assay format below (see FIGS. 15D and 15E).

After addition of 6 μL of HIV-1 and Cal-1 standards and test samples for each well of the designed position and 3 μL of Actin standards and test samples for each well of the designed position. PCR was performed using the following condition: 95° C.-2 min 45 cycles of (94° C.-7 sec, 60° C.-30 sec)

Reagents

SentiFast Probe kit (Line Cat No. BIO-86005)

Standards

HIV-1 standards: 0, 4, 4×10, 4×102, 4×103, 4×104, 4×105, 4×106 copies/μL

Cal-1 standards: 0, 2, 2×10, 2×102, 2×103, 2×104, 2×105, 2×106 copies/μL

Actin standards: 0, 2, 2×10, 2×102, 2×103, 2×104, 2×105, 2×106 copies/μL

Figure 8A:
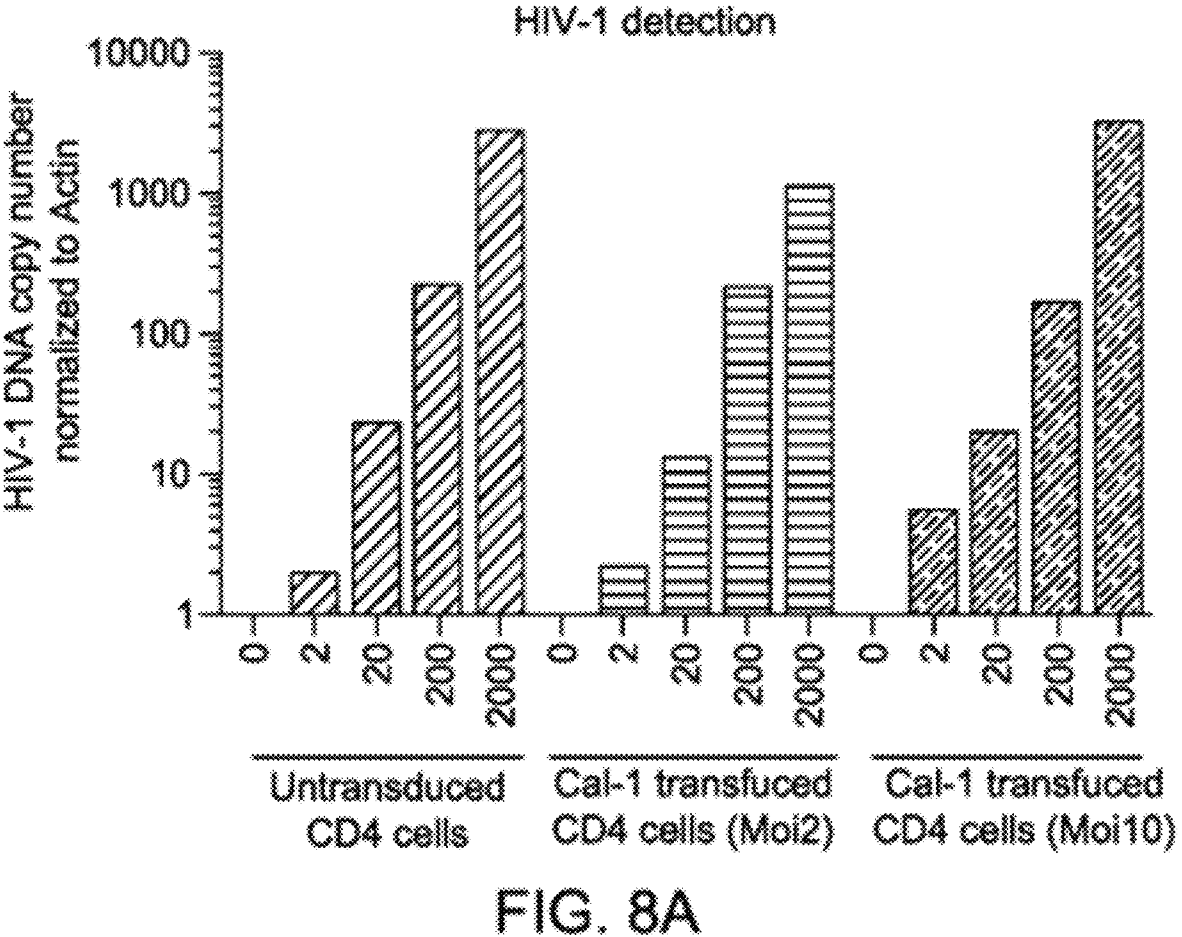
FIGS. 8A and 8B provide graphs showing the results of experiments enabling identifications HIV-1 DNA and Cal-1 DNA copy number using two separate tube assays in accordance with Method 2, as described herein.

HIV-1 integrated DNA data was normalized with 106 copies of Actin (FIG. 8A).

Analysis

Analysis of the Untransduced CD4 cells showed that two U1 cells spiked into 1×10e6 CD4 cells was detected by this assay, as well as 20, 200, and 2000 U1 cells are detected. Linearly increased HIV-1 DNA copies number were detected to the proportion of spiked amount of U1 cells.

In the analysis of the Cal-1 transduced CD4 cells (MOI2), the results showed that the spiked 2, 20, 200, 2000 U1 cells were detected linearly.

In the analysis of the Cal-1 transduced CD4 cells (MOI10), the results showed that the spiked 2, 20, 200, 2000 U1 cells were also detected linearly.

The HIV-1 detected value in the analysis of 2, 20, 200, 2000 U1 cells showed equivalent data across the three groups, indicating that integrated Cal-1 DNA did not interfere with HIV-1 detection (FIG. 8A).

Figure 8B:
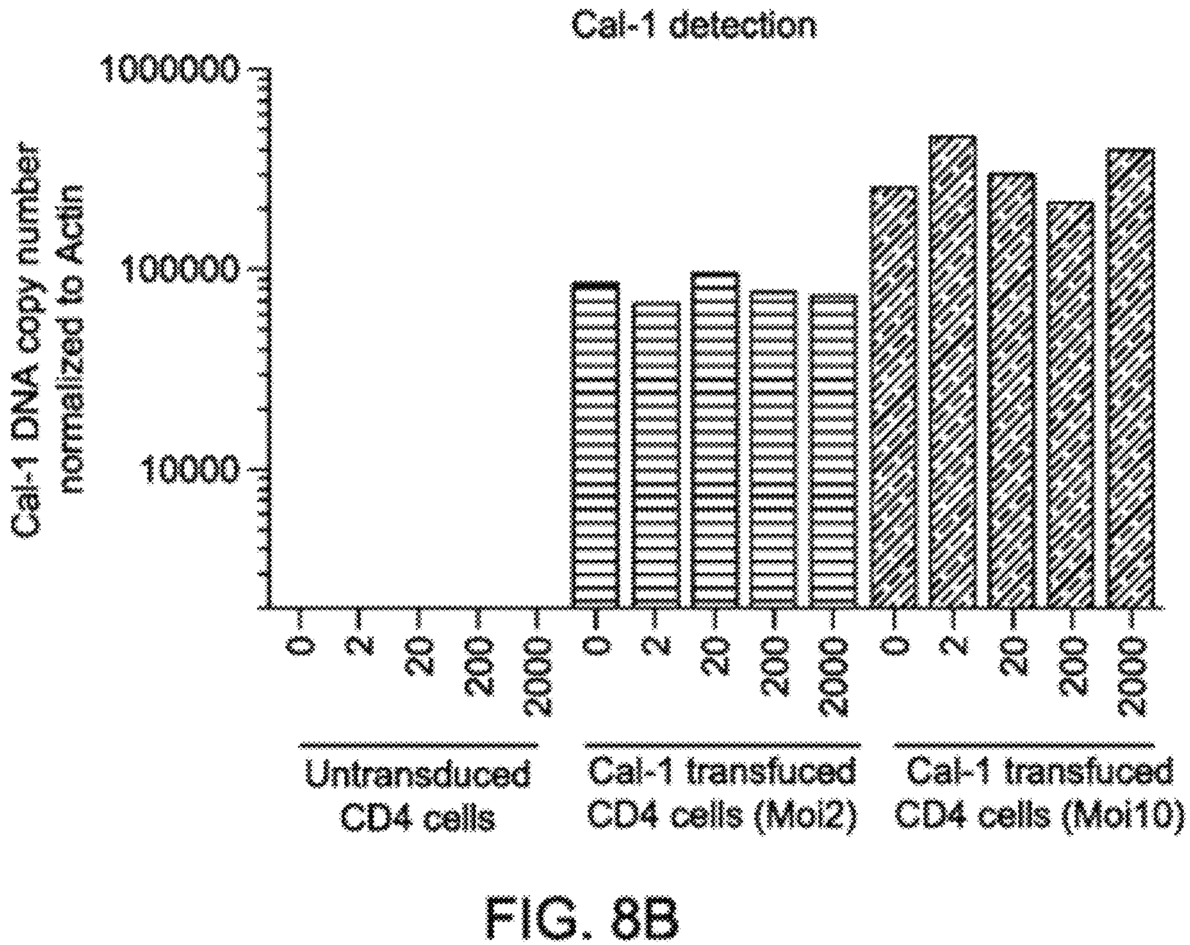

The Cal-1 integrated DNA data was normalized with 106 copies of Actin (FIG. 8B).

The Cal-1 DNA assay did not detect Cal-1 DNA in the Untransduced CD4 cells, despite spiking U1 cells into CD4 cells.

A consistent detection of Cal-1 DNA level was observed for the analysis of Cal-1 transduced CD4 cells (MOI2)".

A consistent detection of Cal-1 DNA level was also observed for the analysis of "Cal-1 transduced CD4 cells (MOI10)". The Cal-1 detected value with MOI=10 were about 50 times higher than that of Cal-1 with MOI=2, indicated more integration of Cal-1 DNA into CD4+ T cells.

Conclusion

1) The HIV-1 assay is sensitive enough to detect HIV-1 DNA obtained from 1 mL of blood from the patients (14 out of 14 HIV-1 positive samples)

2) The Cal-11 assay did not have any cross reactivity to the DNA extracted from the HIV-1

Example 6

Three samples were tested:

1. Untransduced CD4 cells
2. Transduced CD4 with Cal-1-lenti at MOI2
3. Transduced CD4 with Cal-1-lenti at MOI10

These samples were prepared from the same donor.

Sample number 1 is negative control of the experiment, Sample number 2 is Cal-1 transduced CD4+ cells with MOI2, and Sample number 3 is Cal-1 transduced CD4+ cells with MOI10. These samples were obtained at day 14 after transduction of the CD4 cells with Cal-1-lenti.

Aims

A) Evaluation of the New assay based on LTR regions is able to detect CAL-1 integrated DNA using actual donor samples.

B) Checking increased copy number in CAL-1 integrated DNA level with higher MOI transduced cells.

C) Checking cross reactivity of HIV-1 assay: HIV-1 LTR assay should not detect any HIV level in those clinical samples, which have only CAL-1 integrated DNA, since these samples has no HIV-1 infection.

D) Checking in-house control performance: Establishment of the in-house controls is important to assess assay validation for actual sample analysis.

Three in-house controls:

No. 1 <MOLT4 w Cal-1> MOLT4 cells were transduced with Cal-1

No. 2 <80% MOLT4 20% MOLT4-Cal-1> Degree of transduced cells was determined by flow analysis of C46 expression. This experimental setting is for transgene effect of mixture population of original MOLT-4 cells (80%) and Cal-1 transduced MOLT-4 cells (20%).

No. 3 <MOLT4 (w/o Cal-1)> MOLT4 cells only without any transduction of Cal-1

These three group of samples were infected with BaL HIV-1. DNA samples were prepared after 14 days of infection of MOLT-4.

Results (Tables 12, 13, and 14), showing the results of the experiment enabling the identification of HIV-1 and Cal-1 DNA copy number using two separate tube assay (Method-2).

HIV-1 Assay

HIV standard showed good linear detection of HIV-1 DNA from 4-4,000,000 copies/μL Three samples with the same donor, showed no HIV-1 DNA detection: (a) control No. 1 <MOLT4 w Cal-1> showed no HIV; (b) control No. 2 <80% MOLT4 20% MOLT4-Cal-1> showed some level of HIV detection; (c) control No. 3 <MOLT4 without Cal-1> showed much higher levels of HIV detection.

Cal-1 Assay

Cal-1 standard showed good linear detection of Cal-1 DNA from 2-2,000,000 copies/μL: (a) JE #1-3 shows no Cal-1 integration; (b) JE #1-3 transduced with MOI=2 shows 70.5 copes of Cal-1 integration; (c) JE #1-3 transduced with MOI=10 shows 160 copes of Cal-1 integration which is double of the value than that in MOI2; (d) control No. 1 <MOLT4 w Cal-1> showed high level of CAL-1 DNA 773 copes; (d) control No. 2 <80% MOLT4 20% MOLT4-Cal-1> showed much lower level of CAL-1 DNA copies; (e) control No. 3 <MOLT4 without Cal-1> showed no levels of Cal-1 detection.

Conclusions

A) The new assay based on LTR regions is able to detect CAL-1 integrated DNA using actual clinical samples with the same donor.

B) The new assay is able to detect increased copy number in CAL-1 integrated DNA level with higher MOI transduced cells by comparing data with MOI2 and with MOI10.

C) The new assay based on the HIV-1 LTR region does not show any cross reactivity of CAL-1 integrated DNA into the samples.

D) Three new in-house controls are working very well to evaluate this new assay. These three controls are useful for every run of Cal-1 and HIV-1 analysis.

As to HIV-1 assay: (a) HIV-1 copy numbers in the samples are calculated by HIV-1 standards; (b) HIV-1 copy number was normalized by ACTIN DNA copy number in the same extracted DNA, The Normalized HIV copy numbers are calculated by 1000 copies of Actin, which is highlighted with blue letter in the last column.

As to Cal-1 assay: (a) Cal-1 copy numbers in the samples were calculated by Cal-1 standards; (b) Cal-1 copy number was normalized by ACTIN DNA copy number in the same extracted DNA, The Normalized CA1-1 copy numbers were calculated by 1000 copies of Actin, which is highlighted with blue letter in the last column.

As to Actin assay: (a) actin copy numbers in the samples were calculated by Actin standards; (b) these copy numbers were used for normalization of HIV-1 and Cal-1 copy number in the samples.

Table 12 provides: HIV-1 copy numbers in the samples calculated by HIV-1 standards; the HIV-1 copy number was normalized by ACTIN DNA copy number in the same extracted DNA. The Normalized HIV copy numbers were calculated by 1000 copies of Actin, which is listed in the last column. Note: The cp (crossing point-PCR-cycle) value is the cycle at which fluorescence achieved a defined threshold. The HIV standard showed good linear detection of HIV-1 DNA from 4-4,000,000 copies/μL. Three samples with the same donor (untransduced, transduced with MOI2, transduced with MOI10) showed no HIV-1 DNA detection. In house control No. 1 <MOLT4 with Cal-1 > with HIV infected samples showed no HIV. In house control No. 2 <80% MOLT4 20% MOLT4-Cal1> with HIV infected samples showed some level of HIV detection. In house control No. 3 <MOLT4 without Cal1> with HIV infected samples showed much higher levels of HIV detection.

Table 13 provides Cal-1 analysis data. Cal-1 copy numbers in the samples were calculated by Cal-1 standards. Cal-1 copy number was normalized by ACTIN DNA copy number in the same extracted DNA. The Normalized CA1-1 copy numbers were calculated by 1000 copies of Actin, which is listed in the last column. Cal-1 standard showed good linear detection of Cal-1 DNA from 2-2,000,000 copies/μL. Untrancduced JE #1-3 showed no CAL1 integration. JE #1-3 transduced with MOI=2 showed 70.5 copes of CAL1 integration. JE #1-3 transduced with MOI=10 showed 160 copies of CAL1 integration, which is double of the value than that in MOI2. In-house control No. 1 <MOLT4 w Cal1> with HIV infected sample, showed high level of CAL1 DNA 773 copes. In house control No. 2 <80% MOLT4 20% MOLT4-Cal1> with HIV infected samples showed much lower level of CAL1 DNA copies. In house control No. 3 <MOLT4 without Cal1> with HIV infected samples showed no levels of Cal-1 detection.

Table 14 provides Actin analysis data. Actin copy numbers in the samples were calculated by Actin standards. These copy numbers were used for normalization of HIV-1 and Cal-1 copy number in the samples.

TABLE 12

HIV CAL Actin Assay

| Position | Name | Cp | HIV-1 Concentration | Actin | HIV-1 copy per 10(3) Actin copy |
|---|---|---|---|---|---|
| A2 | NC | | 0 | | |
| B2 | HIV standard | 38.22 | 4 | | |
| C2 | HIV standard | 33.21 | 40 | | |
| D2 | HIV standard | 29.88 | 400 | | |
| E2 | HIV standard | 27.44 | 4000 | | |
| F2 | HIV standard | 23.41 | 40000 | | |
| G2 | HIV standard | 20.33 | 400000 | | |
| H2 | HIV standard | 16.73 | 4000000 | | |
| A3 | <Untrancduced JE #1-3> using $5 \times 10^6$ | | 0 | 11137166 | 0 |
| B3 | <JE #1-3 transduced with MOI = 2> $5 \times 10^6$ | | 0 | 8705100 | 0 |
| C3 | <JE #1-3 transduced with MOI = 10> $5 \times 10^6$ | | 0 | 3901724 | 0 |
| D3 | NO. 1 control <MOLT4 w Cal1> with HIV day 14 | | 0 | 44498 | 0 |
| E3 | NO. 2 control <80% MOLT4 20% MOLT4-Cal1> with HIV day 14 | 25.57 | 10598 | 67407 | 157 |
| F3 | NO. 3 control <MOLT4 (w/o Cal1)> with HIV day14 | 22.35 | 90697 | 86849 | 1,044 |

TABLE 13

HIV CAL Actin Assay

| Position | Name | Cp | Cal-1 Concentration | Actin | Cal-1 copy per 10(3) Actin copy |
|---|---|---|---|---|---|
| A5 | NC | | 0 | | |
| B5 | Cal standard | 37.7 | 2 | | |
| C5 | Cal standard | 36.8 | 20 | | |
| D5 | Cal standard | 34.13 | 200 | | |
| E5 | Cal standard | 30.76 | 2000 | | |
| F5 | Cal standard | 27.48 | 20000 | | |
| G5 | Cal standard | 23.6 | 200000 | | |
| H5 | Cal standard | 20.45 | 2000000 | | |
| A6 | <Untrancduced JE #1-3> using $5 \times 10^6$ | | | 11137166 | 0.0 |
| B6 | <JE #1-3 transduced with MOI = 2> $5 \times 10^6$ | 22.6 | 613511 | 8705100 | 70.5 |
| C6 | <JE #1-3 transduced with MOI = 10 > $5 \times 10^6$ | 22.58 | 622911 | 3901724 | 159.7 |
| D6 | NO. 1 control <MOLT4 w Cal1> with HIV day 14 | 26.39 | 34388 | 44498 | 772.8 |
| E6 | NO. 2 control <80% MOLT4 20% MOLT4-Cal1> with HIV day 14 | 32.29 | 388 | 67407 | 5.7 |
| F6 | NO. 3control <MOLT4 (w/o Cal1)> with HIV day14 | | 0 | 86849 | 0.0 |

TABLE 14

| HIV CAL Actin Assay | | | |
|---|---|---|---|
| Position | Name | Cp | Actin Concentration |
| A8 | NC | | 0 |
| B8 | Actin standard | 39.56 | 2 |
| C8 | Actin standard | 39.56 | 20 |
| D8 | Actin standard | 34.78 | 200 |
| E8 | Actin standard | 30.85 | 2000 |
| F8 | Actin standard | 28.03 | 20000 |
| G8 | Actin standard | 24.26 | 200000 |
| H8 | Actin standard | 21.48 | 2000000 |
| A9 | <Untrancduced JE #1-3> using $5 \times 10^6$ | 18.97 | 11137166 |
| B9 | <JE #1-3 transduced with MOI = 2> $5 \times 10^6$ | 19.32 | 8705100 |
| C9 | <JE #1-3 transduced with MOI = 10> $5 \times 10^6$ | 20.46 | 3901724 |
| D9 | NO. 1 control <MOLT4 w Cal1> with HIV day 14 | 26.81 | 44498 |
| E9 | NO. 2 control <80% MOLT4 20% MOLT4-Call> with HIV day 14 | 26.22 | 67407 |
| F9 | NO. 3control <MOLT4 (w/o Cal1)> with HIV day 14 | 25.86 | 86849 |

Example 7

Three sets of samples were prepared based on MOLT-4 infectious model. FIG. 10 provides graphs showing transduction efficiency in MOLT-4 cells (FIG. 10A) and cultured supernatants analyses to detect amount of HIV-1 virus released from the HIV-1 infected MOLT-4 cells by RT assay (FIG. 10B, C) and by one step reverse transcriptase real-time (RT)-PCR analysis (FIG. 10D).

Three sets of samples were prepared based on MOLT-4 cells to see an impact of Cal-1 protection from HIV-1 infection.

A) MOLT-4 cells only without any transduction of Cal-1 lenti-vector;

B) MOLT-4 cells transduced with lenti-ccr5 vector;

C) MOLT-4 cells transduced with Cal-1 lenti-vector.

MOLT-4 Cell were transduced with either with lenti-sh5 and lenti-Cal-1 with MOI 2.5. Transduction was determined after 48 hours incubation, utilizing 2F5 and ccr5 staining on MOLT-4 cells with flow cytometry analysis.

Figure 10A:
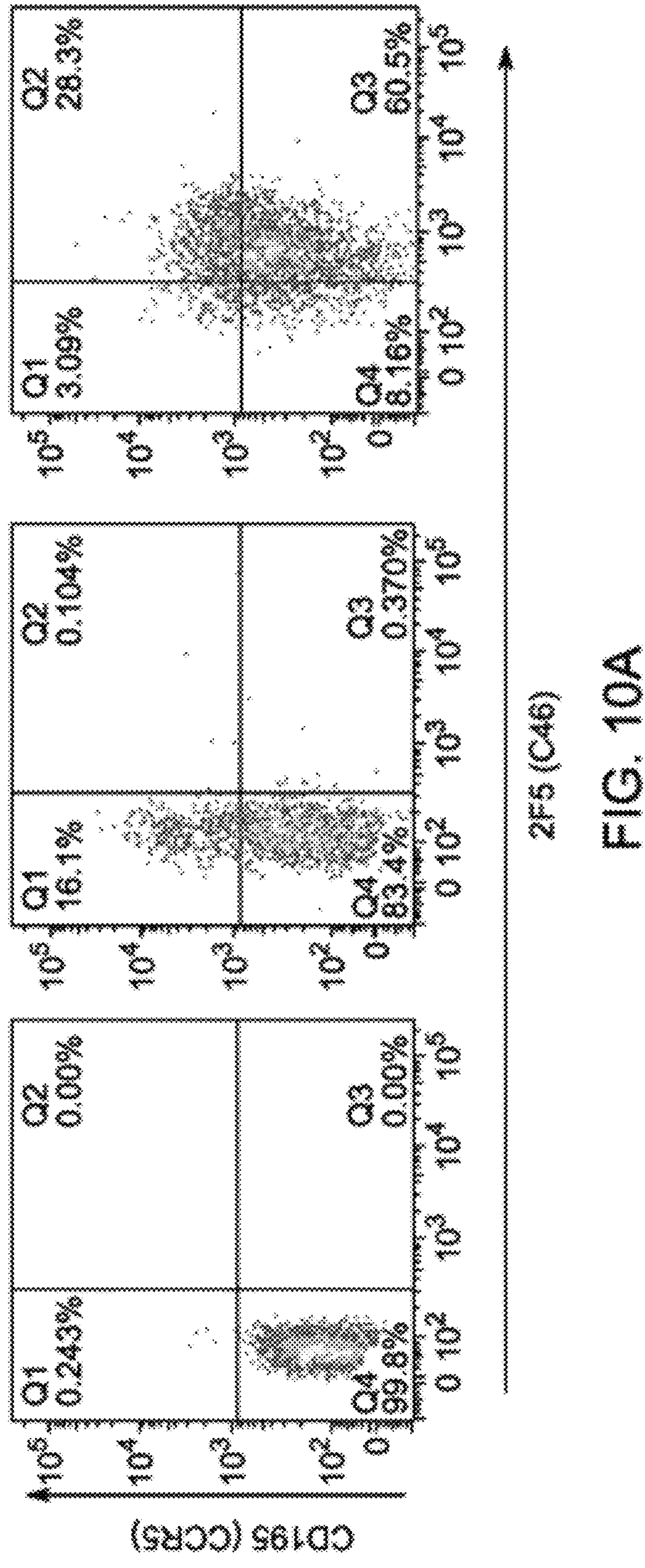
FIG. 10B provides a reverse transcriptase assay of MOLT4 with ccr5 and MOLT4 with Cal-1, after HIV-1 infection. 48 hours post transduction MOLT4 cells were infected with BaL at MOI 0.2. 7-days post transduction, reverse transcriptase activity in the cultured supernatant was tested. The combination of CCR5 and the C46 fusion inhibitor (Cal-1) showed significantly suppressed in reverse transcriptase activity compared with those of lenti-sh5 transduced MOLT4 cells and untransduced MOLT4 cells.
FIG. 10C provides time course data for a reverse transcriptase assay of three conditions: (a) MOLT4 transduced with Cal-1; (b) 80% untransduced MOLT4 mixed with 20% Cal-1 transduced; and (c) MOCK control. The figure illustrates an over 2 log reduction in reverse transcriptase activity was observed in Cal-1-transduced with MOLT4 cells at day 14, compared with a mixed culture of 20% Cal-1-transduced and 80% untransduced MOLT4 cells and untransduced MOLT4 cells (MOCK control) at day-14.
FIG. 10D provides time course data for reverse transcriptase real time PCR analysis of these three in-vitro experimental sets. The previous RT data were confirmed by this TaqMan based reverse transcriptase real-time PCR assay. The figure illustrates an over 2 log reduction in HIV-1 RNA extracted from the cultured supernatant of Cal-1-transduced MOLT4 cells at day 14 was observed, compared with data from a mixed culture of 20% Cal-1-transduced and 80% untransduced MOLT4 cells and untransduced MOLT4 cells (MOCK control).

FIG. 10A provides a flow analysis of MOLT-4 cells with lenti-ccr5 and Cal-1 (ccr5 and C46). Lenti-ccr5 alone transduced MOLT-4 cells indicated about a 75% reduction in CCR5 expression. The data of Lenti-Cal-1 transduced MOLT-4 cells revealed that about 89% of the cells expressed C46 and about a 68% reduction in CCR5 expression was also observed.

Figure 10B:
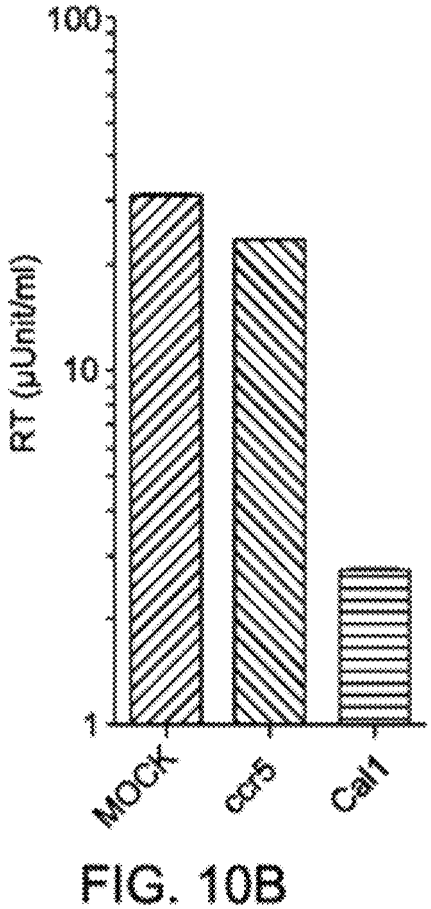

FIG. 10B provides a reverse transcriptase assay of MOLT4 with lenti-ccr5 and MOLT4 with Cal-1, after HIV-1 infection using two separate tube assays in accordance with Method-2. 48 hours post transduction MOLT4 cells were infected with BaL at MOI 0.2. 7-days post transduction, reverse transcriptase activity in the cultured supernatant was tested. The combination of CCR5 and the C46 fusion inhibitor (Cal-1) showed significantly suppressed in reverse transcriptase activity compared with those of lenti-ccr5 transduced MOLT4 cells and untransduced MOLT4 cells.

We set up another three sets of samples were prepared based on MOLT-4 cells, which were identical to the experimental settings described in Example 1 in order to confirm the previous data with this repeated experiment.

a. MOLT-4 cells only without any transduction of Cal-1 lentivirus;

b. 80% of MOLT-4 cells and 20% of MOLT-4 cells with transduction of Cal-1 lentivirus. Degree of transduced cells was determined by flow cytometry analysis of C46 expression. This experimental setting is for transgene effect of mixture population of original MOLT-4 cells (80%) and Cal-1 transduced MOLT-4 cells (20%);

c. MOLT4 Cal-1 (100%). 100% of Cells were transduced with Cal-1 as determined by C46 expression on Flow cytometry.

The experimental procedure was the same as in Example 1 herein. Briefly, about 0.5 million of these cells were infected with HIV-1 BaL. These cells were cultured in a 25-cm$^2$ culture Flask using 10 mL of a standard RPMI-1640 based medium containing 10% FBS with of ix glutamax supplement in CO2 incubator. Cultured supernatant samples (1 mL) were taken at day 4, 7, 10, 14 for analysis of both RT assay (FIG. 10C) and reverse transcriptase real-time (RT)-PCR assay (FIG. 10D). Cultured cell samples were also prepared at day 4, 7, 10, 14 for analysis of both Intracellular analyses of DNA (FIG. 11AB) and RNA (FIG. 12AB). At each time point, 0.6 mL of the cultured cell suspension for DNA analysis and 0.4 mL of the cultured cell suspension for RNA analysis were transferred 2.0 mL of standard Eppendorf tubes. These tubes were centrifuged at 900 g for 3 min. The supernatant was removed. One mL of PBS was added to each tube, followed by centrifuge at 900 g for 3 min. The supernatant was removed. The cell pellets were used for RNA and DNA analysis.

Figure 10C:
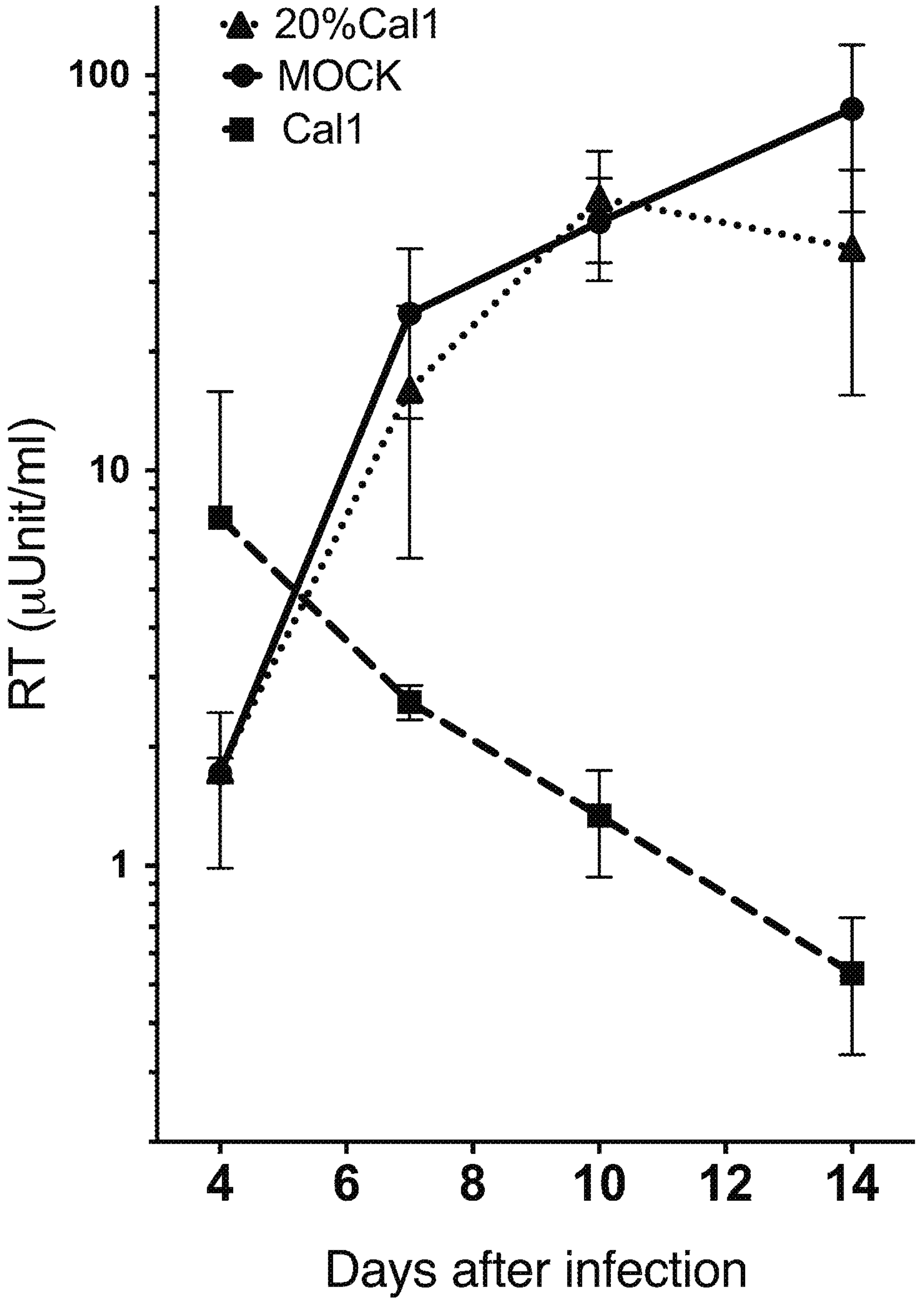
Figure 10D:
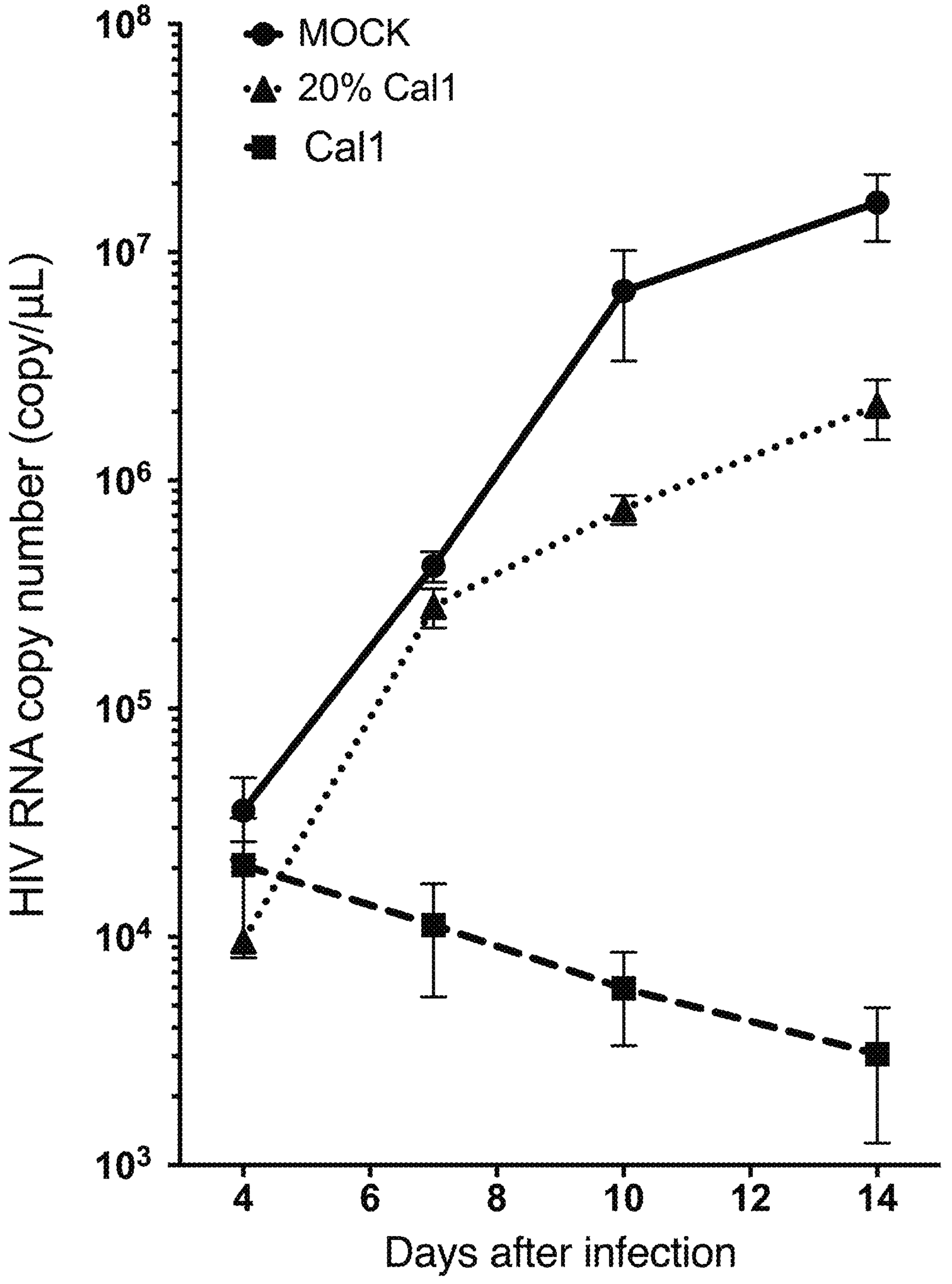

FIG. 10C provides time course data for a reverse transcriptase assay of three conditions: (a) MOLT4 transduced with Cal-1; (b) 80% untransduced MOLT4 mixed with 20% Cal-1 transduced; and (c) MOCK control. The data reveals that an over 2 log reduction in reverse transcriptase activity was observed in Cal-1-transduced with MOLT4 cells at day 14, compared with a mixed culture of 20% Cal-1-transduced and 80% untransduced MOLT4 cells and untransduced MOLT4 cells (MOCK control) at day-14.

Reverse Transcriptase assay (RT assay) (FIG. 10C) was used to measure amount of HIV-1 in 10 μL of culture supernatant, released from infected MOLT-4 (Suzuki K, et al: Poly A-linked non-isotopic microtiter plate reverse transcriptase assay for sensitive detection of clinical human immunodeficiency virus isolates. J Virol Methods 1995, 55:347-356).

FIG. 10D provides a graph showing the results of the experiment enabling the identification of HIV-1 RNA copy number with Method 2 using 500 μL of cultured supernatant. RNA was extracted from cultured supernatant using an automated extraction system (EasyMag, bioMerieux) with 60 μL of elution volume setting.

The LightCycler-480 (Roche) and the white 96-well plate for LightCycler-480 were used in one step reverse transcriptase real-time PCR analysis.

A Master mix per protocol was made for 8 standards and samples analysis (see Table 15).

TABLE 15

| PCR Master mix for the detection of HIV-1 mRNA, where a total volume of the mix was 34 microliters. | |
|---|---|
| DNase RNase free water | 11.20 |
| 2 × B (from kit) | 20.00 |
| Tata forward primer 20 μM) | 0.50 |
| Imai-LTR-Rev (20 μM) | 0.50 |

TABLE 15-continued

| PCR Master mix for the detection of HIV-1 mRNA, where a total volume of the mix was 34 microliters. | |
|---|---|
| HIV-1 Tata Probe (5 μM) with FAM label | 0.60 |
| RT enzyme (from Kit) | 0.40 |
| RNase Inhibitor (from kit | 0.80 |

An aliquot of 34 μL of Master mix was dispensed into the each well of a 96-well plate.

After addition of 6 μL of standards and samples for each well at the designated position.

RT-PCR was started with the following condition: 45° C.-20 min, 95° C.-2 min 45 cycles of (94° C.-7 sec, 60° C.-30 sec)

Reagents

SensiFAST Probe One step kit (BioLine #BIO-76005)

Standards

HIV-1 standards: 0, 4, 4×10, 4×102, 4×103, 4×104, 4×105, 4×106 copies/μL

FIG. 10D provides time course data for one step reverse transcriptase real-time (RT)-PCR analysis. The previous RT data were confirmed by this TaqMan based real time PCR assay. The figure reveals that an over 2 log reduction in HIV-1 RNA extracted from the cultured supernatant of Cal-1-transduced MOLT4 cells at day 14 was observed, compared with data from a mixed culture of 20% Cal-1-transduced and 80% untransduced MOLT4 cells and untransduced MOLT4 cells (MOCK control).

Note: No Cal-1 assay was performed for these samples. Only HIV-1 specific detection was conducted for these samples.

Example 8

Figure 11A:
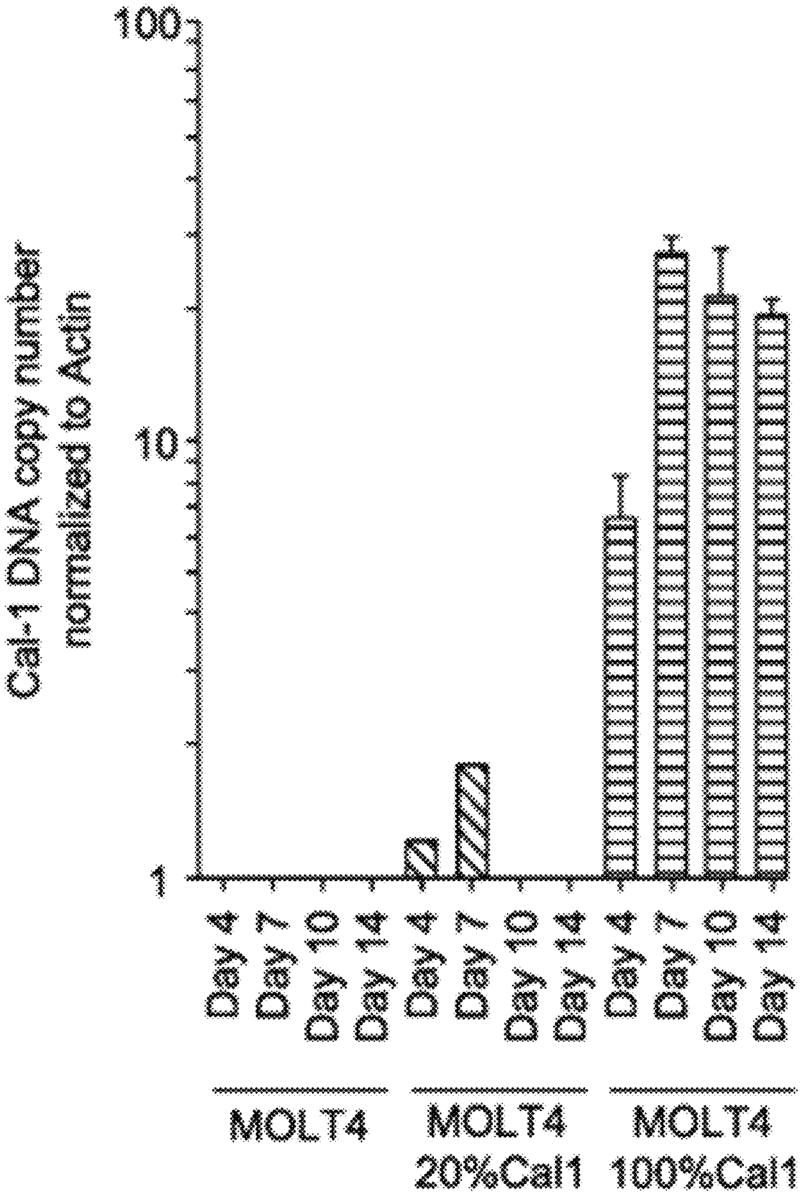
FIG. 11A illustrates the results of Cal-1 detection according to embodiments of the present disclosure, using two separate tube assays in accordance with Method 2, herein. Cal-1 integrated DNA was amplified by a TaqMan based DNA PCR method based on assay methods disclosed herein. Real-time DNA PCR was conducted with the extracted DNA from three sets of MOLT4 based infectious experiments. The data show that consistent presence of integrated Cal-1 DNA levels (normalized by Actin) were detected in Cal-1 transduced MOLT4 cells throughout experiment from day-4 to day-14. Cal-1 DNA was not detected in MOLT4 cells (MOCK control). Significant reduction of integrated level of Cal-1 DNA in a mixed culture of 20% Cal-1-transduced and 80% untransduced MOLT4 cells was evident at day 4 and 7. By day 10 and 14 these levels had further dropped to down to an undetectable level. Cal-1 copy numbers were normalized with 1000 copies of Action DNA.
Figure 11B:
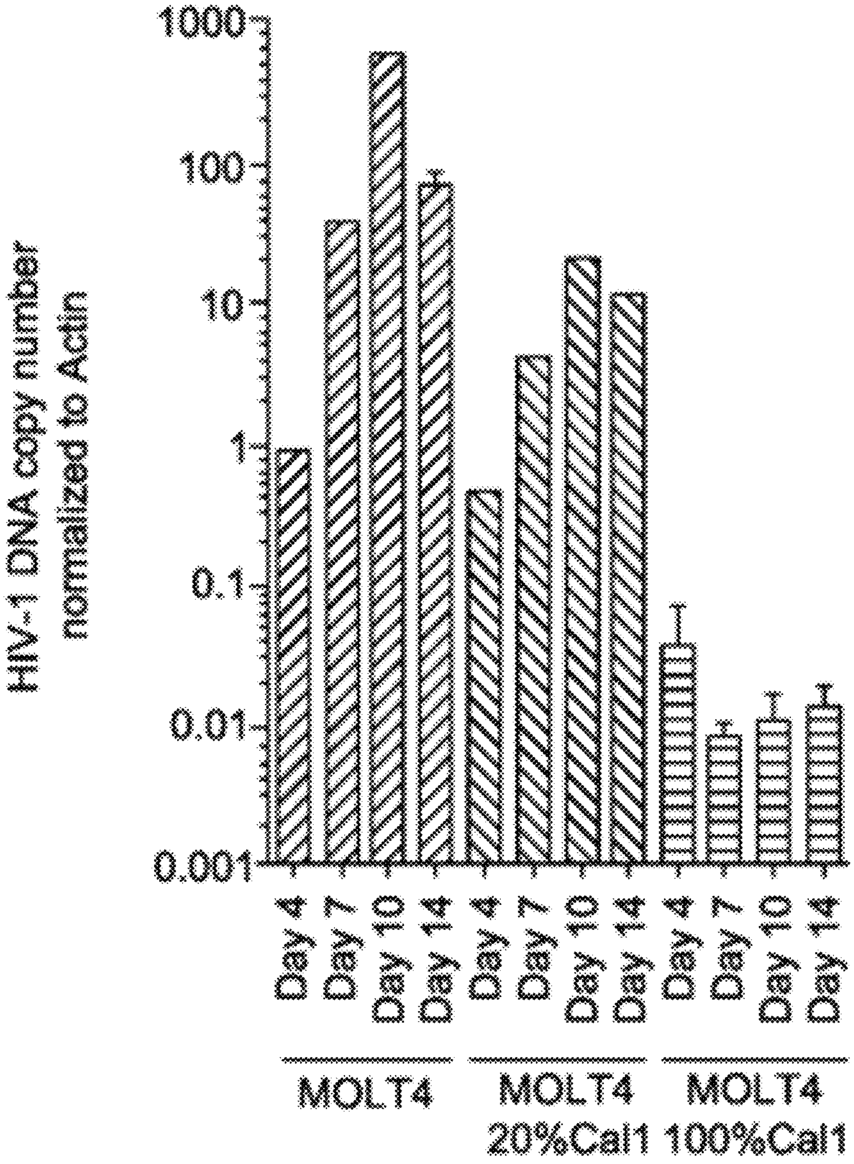
FIG. 11B illustrates the results of HIV-1 detection according to embodiments of the present disclosure using two separate tube assays in accordance with Method 2 herein. Over a three log reduction in the integrated level of HIV-1 DNA was observed in the Cal-1 transduced MOLT4 cells compared with that of untransduced MOLT4 cells throughout day-4 to day-14 after HIV-1 infection. This data confirms the protection in MOLT4 cells from HIV-1 infection after transduction of Cal-1 lentiviral vector. Elevated level of HIV-1 DNA in a mixed culture of 20% Cal-1-transduced and 80% untransduced MOLT4 cells on day 10 and day 14, compared with those of day 4 and day 7. The Cal-1 DNA data in a mixed culture of 20% Cal-1-transduced and 80% untransduced MOLT4 cells on day 10 and day 14 suggested that loss of integrated Cal-1 DNA in those time points. Therefore, increasing HIV-1 DNA levels in a mixed culture on day 10 and day 14 was observed. Those data also are suggesting that Cal-1 transgene function of protection of HIV-1 infection. HIV-1 copy numbers were normalized with 1000 copies of Action DNA.
Figure 12A:
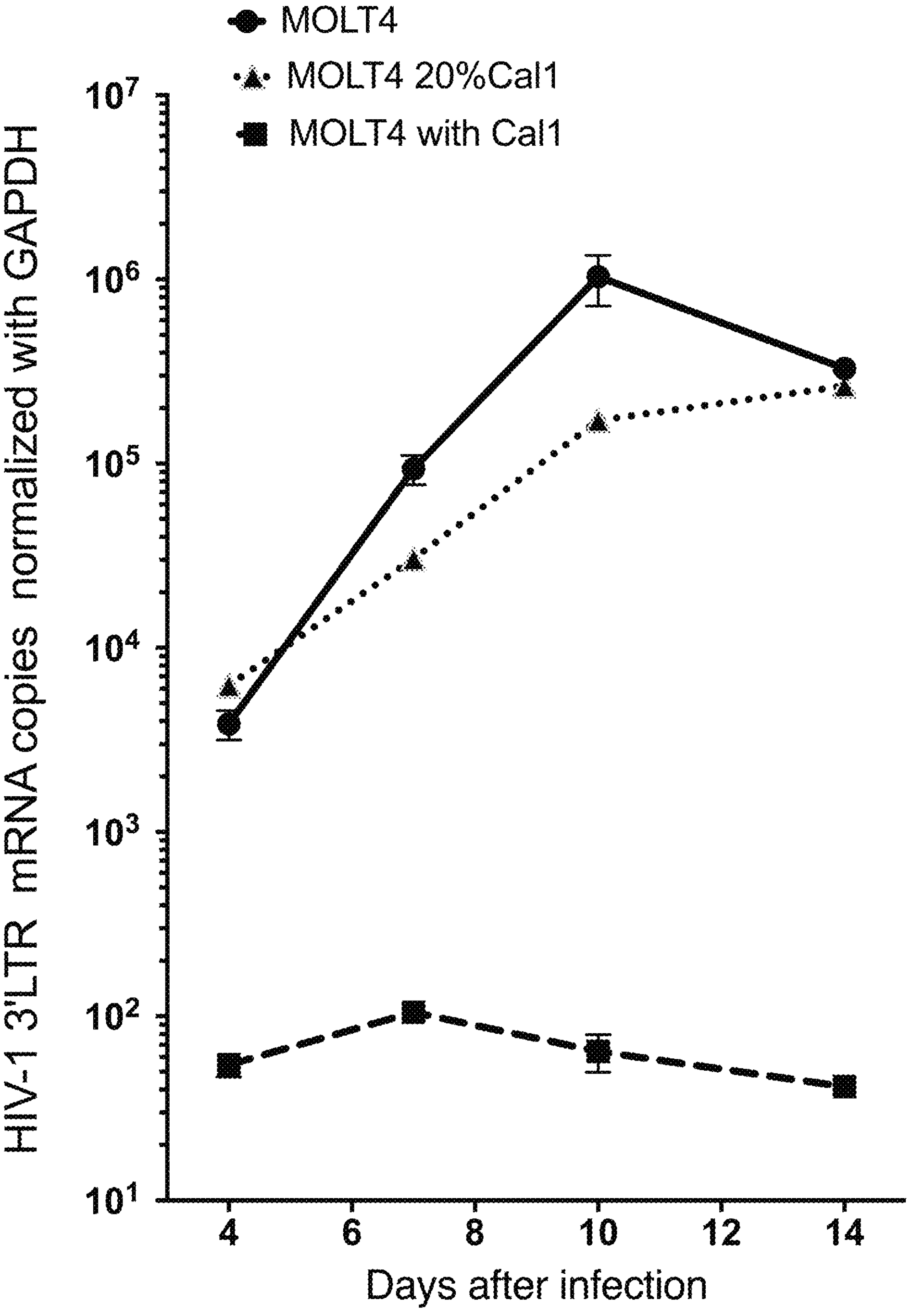
FIG. 12A sets forth an intracellular analysis of HIV-1 RNA in MOLT-4 cells, based on a 3'LTR assay with Method 2, herein. Over a 3 log reduction of integrated level of HIV-1 viral RNA in the Cal-1 transduced MOLT4 cells was observed compared to untransduced MOLT4 cells throughout days 4 to 14 after HIV-1 infection.
Figure 12B:
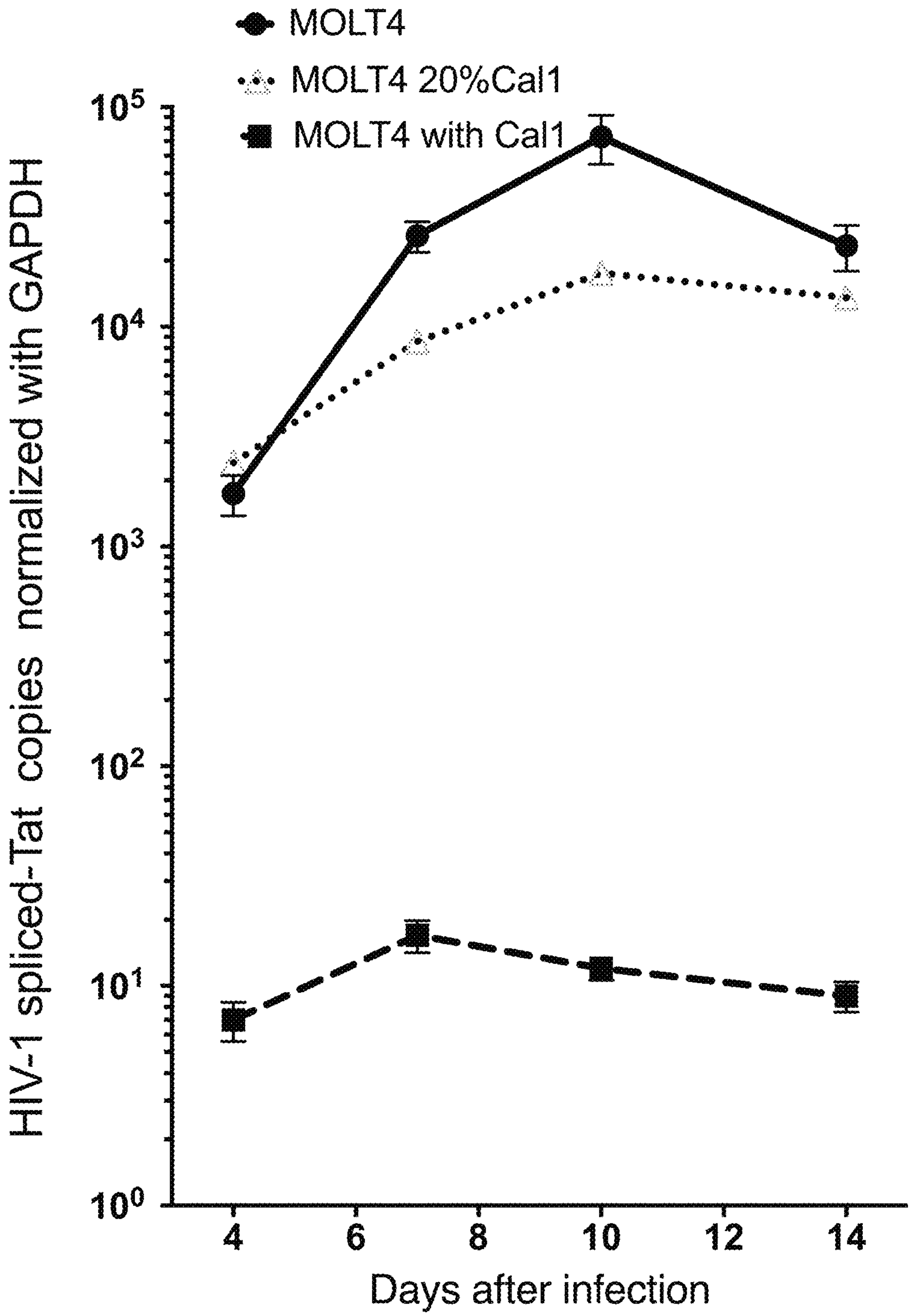
FIG. 12B sets forth an intracellular analysis of HIV-1 RNA in MOLT-4 cells, based on spliced-Tat assay. The similar level of massive reduction was observed RNA in the Cal-1 transduced MOLT4 cells based on spliced-Tat assay. TAT protein generated by the spliced-Tat mRNA is able to drive massive amount of un-spliced HIV-1 mRNA. Detection of spliced-Tat mRNA is critical marker of an initial HIV-1 transcript. HIV-1 RNA copy numbers were normalized with 1,000,000 copy of GAPDH mRNA. Both FIGS. 12A and 12B data suggested that a massive reduction of HIV-1 intracellular mRNA levels was observed, which is supported by the observed large reduction of integrated DNA levels in the Cal-1 transduced MOLT4 cells (see FIGS. 11A and 11B).

FIGS. 11A and 11B provide graphs showing the results of experiments enabling the identification of HIV-1 DNA and Cal-1 DNA copy number using two separate tube assays in accordance with Method-2.

DNA was extracted from the cell pellets prepared at day 4, 7, 10, 14 using PurLink Genomic DNA kits (ThermoFisher) with 60 ul of elution volume.

Note: LightCycler 480 (Roche) and the white 96-well plate for LightCycler-480 were used in this analysis one step real-time PCR analysis.

Three Master mixes per protocol were made for 8 standards and samples analysis (see Tables 16, 17, and 18).

i) Master mix 1 is for detection of HIV-1 DNA ii) Master mix 2 is for detection of Cal-1 DNA iii) Master mix 3 is for detection of Actin detection

TABLE 16

| PCR Master 1 mix for detecting HIV-1 DNA, where a total volume of the mix was 34 microliters. | |
|---|---|
| DNase RNase free water | 12.40 |
| 2 × B (from the kit) | 20.00 |
| Tata forward primer (20 μM) | 0.50 |
| Imai-LTR-Rev (20 μM) | 0.50 |
| TAR Probe (5 μM) with FAM label | 0.60 |

TABLE 17

| PCR Master mix 2 for detecting Cal-1 DNA, where a total volume of the mix was 34 microliters. | |
|---|---|
| DNase RNase free water | 12.40 |
| 2 × B (from the kit) | 20.00 |

TABLE 17-continued

| PCR Master mix 2 for detecting Cal-1 DNA, where a total volume of the mix was 34 microliters. | |
|---|---|
| NuAf (20 μM) | 0.50 |
| Imai-LTR-Rev (20 μM) | 0.50 |
| Cal-1 Probe (5 μM) with Cy5 label | 0.60 |

TABLE 18

| PCR Master mix 3 for the detection of actin, where a total volume of the mix was 17 microliters. | |
|---|---|
| DNase RNase free water | 6.20 |
| 2 × B (from the kit) | 10.00 |
| Actin forward primer (20 μM) | 0.25 |
| Actin reverse primer (20 μM) | 0.25 |
| ActinProbe (5 μM) with FAM | 0.30 |

An aliquot of 34 μL of Master 1 mix was dispensed into the each well of 96-well plate in the designed position of the well. An aliquot of 340 μL of Master 2 mix was dispensed into the each well of 96-well plate. and an aliquot of 170 μL of Master 3 mix was dispensed into the each well of 96-well plate After addition of 6 μL of standards and samples for each well of the Master 1 mix and Master 2, and addition of 3 μL of standards and samples for each well of the Master 3 mix PCR was started with the following condition: 95° C.-2 min 45 cycles of (94° C.-7 sec, 60° C.-30 sec)

Reagents

SentiFast Probe kit (Line Cat No. BIO-86005)

Standards

HIV-1 standards: 0, 4, 4×10, 4×102, 4×103, 4×104, 4×105, 4×106 copies/μL

Cal-1 standards: 0, 2, 2×10, 2×102, 2×103, 2×104, 2×105, 2×106 copies/μL

Actin standards: 0, 2, 2×10, 2×102, 2×103, 2×104, 2×105, 2×106 copies/μL

Cal-1 integrated DNA and HIV-1 integrated DNA data were normalized with 1000 copies of Actin (FIG. 11AB).

FIG. 11A illustrates the results of Cal-1 detection according to embodiments of the present disclosure. Cal-1 integrated DNA was amplified by a TaqMan based DNA PCR method based on assay methods, illustrated in FIG. 3, disclosed herein. Real-time DNA PCR was conducted with the extracted DNA from three sets of MOLT4 based infectious experiments. The data show that consistent presence of integrated Cal-1 DNA levels (normalized by Actin) were detected in Cal-1 transduced MOLT4 cells throughout experiment from day-4 to day-14. Cal-1 DNA was not detected in MOLT4 cells (MOCK control). A significant reduction of integrated level of Cal-1 DNA was observed in a mixed culture of 20% Cal-1-transduced and 80% untransduced MOLT4 cells as evident at day 4 and 7. By day 10 and 14 these levels had further dropped down to an undetectable level. Cal-1 copy numbers were normalized with 1000 copies of Action DNA.

FIG. 11B illustrates the results of HIV-1 detection according to embodiments of the present disclosure. Over 3 log reduction in the integrated level of HIV-1 DNA was observed in the Cal-1 transduced MOLT4 cells compared with that of untransduced MOLT4 cells throughout day-4 to day-14 after HIV-1 infection. This data confirms the protection in MOLT4 cells from HIV-1 infection after transduction of Cal-1 lentiviral vector. Elevated level of HIV-1

DNA in a mixed culture of 20% Cal-1-transduced and 80% untransduced MOLT4 cells on day 10 and day 14, compared with those of day 4 and day 7. The Cal-1 DNA data in a mixed culture of 20% Cal-1-transduced and 80% untransduced MOLT4 cells on day 10 and day 14 suggested that loss of integrated Cal-1 DNA in those time points. Therefore, increasing HIV-1 DNA levels in a mixed culture on day 10 and day 14 was observed. The data also suggest that Cal-1 transgene functions to protect against HIV-1 infection. HIV-1 copy numbers were normalized with 1000 copies of Action DNA.

Example 9

FIG. 12A provides graphs showing the results of experiments enabling the identification of HIV-1 RNA copy number with Method-2. In order to detect HIV-1 intercellular RNA level, HIV-1 specific LTR mRNA was analyzed (FIG. 12A). RNA was extracted from the cell pellets prepared at day 4, 7, 10, 14 using ReliaPrep RNA Miniprep system (Promega) with 60 ul of elution volume.

Note: LightCycler 480 (and the white 96-well plate for LightCycler-480 were used in this analysis one step reverse transcriptase real-time (RT)-PCR analysis.

A two Master mix per protocol was made for 8 standards and samples analysis (see Tables 19 and 20).

PCR Master 1 mix: Master mix is for HIV-1 mRNA detection.

PCR Master 2 mix: Master mix is for GAPDH mRNA detection.

TABLE 19

PCR Master 1 mix for HIV mRNA detection, where the mix had a total volume of 34 microliters.

| | |
|---|---|
| DNase RNase free water | 11.20 |
| 2 × B (from kit) | 20.00 |
| NuAf (20 μM) | 0.50 |
| Imai-LTR-Rev (20 μM) | 0.50 |
| HIV-1 Tata Probe (5 μM) with FAM label | 0.60 |
| RT enzyme (from Kit) | 0.40 |
| RNase Inhibitor (from kit | 0.80 |

TABLE 20

PCR Master 2 mix for detection of GAPDH mRNA, where the mix had a total volume of 17 microliters.

| | |
|---|---|
| DNase RNase free water | 5.60 |
| 2 × B (from kit) | 10.00 |
| GAPDH forward primer (20 μM) | 0.25 |
| GAPDH forward primer (20 μM) | 0.25 |
| GAPDH Taq Probe (5 μM) Cy5 label | 0.30 |
| RT enzyme (from Kit) | 0.20 |
| RNase Inhibitor (from kit | 0.40 |

An aliquot of 34 μL of Master 1 mix was dispensed into the each well of 96-well plate and an aliquot of 17 μL of Master 2 mix was dispensed into the each well of 96-well plate in the designed position of the well.

After addition of 6 μL of standards and samples for each well of the Master 1 mix and addition of 3 μL of standards and samples for each well of the Master 2 mix. PCR was started with the following condition: 45° C.-20 min 95° C.-2 min 45 cycles of (94° C.-7 sec, 60° C.-30 sec)

Reagents

SensiFAST Probe One step kit (BioLine #BIO-76005)

Standards

HIV-1 standards: 0, 4, 4×10, 4×102, 4×103, 4×104, 4×105, 4×106 copies/μL

GAPDH standards: 0, 2, 2×10, 2×102, 2×103, 2×104, 2×105, 2×106 copies/μL

HIV-1 mRNA analysis data was normalized with 106 copies of mRNA expression of GAPDH (FIG. 12A).

Example 10

Two sets of samples were prepared based on PBMCs infectious model. The cultured supernatants analyses to detect amount of HIV-1 virus released from the HIV-1 infected PBMCs by RT assay (FIG. 13A) and by one step reverse transcriptase real-time (RT)-PCR analysis (FIG. 13B).

Two sets of samples were prepared based on PBMCs to see an impact of Cal-1 protection from HIV-1 infection.

A) PBMCs only without any transduction of Cal-1 lentiviral vector.

B) PBMCs transduced with Cal-1 lentiviral vector.

PBMCs were prepared by a single healthy donor. A standard PHA stimulation method was used to stimulate PNMCs for 3-days pre-culture, followed by the transduction with lenti-Cal-1 with MOI 2.5.

Experimental procedure was as following. Three million of both transduced-PBMCs and PBMCs alone without transduction were infected with HIV-1 BaL. These cells were cultured in a 6-well cultured plate using 4 mL of a standard RPMI-1640 based medium containing 10% FBS with of 1× glutamax supplement in CO2 incubator. Cultured supernatant samples (1 mL) were taken at day 4, 7, 10, 14 for analysis of both RT assay (FIG. 13A) and reverse transcriptase real-time (RT)-PCR assay (FIG. 13B). Cultured cell samples were also prepared at day 4, 7, 10, 14 for analysis of both Intracellular analyses of DNA (FIG. 14AB) and RNA (FIG. 14C). At each time point, 0.6 mL of the cultured cell suspension for DNA analysis and 0.4 mL of the cultured cell suspension for RNA analysis were transferred 2.0 mL of standard Eppendorf tubes. These tubes were centrifuged at 900 g for 3 min. The supernatant was removed. One mL of PBS was added to each tube, followed by centrifuge at 900 g for 3 min. The supernatant was removed. The cell pellets were used for RNA and DNA analysis.

FIG. 13B illustrates a reverse-transcriptase real time PCR analysis on RNA in cultured supernatants in accordance with Method-2. The reverse-transcriptase data in FIG. 14*a* were confirmed by a TaqMan based real time reverse-transcriptase-PCR assay using the extracted RNA from the cultured supernatant. A five-fold reduction in HIV-1 RNA from the cultured supernatant of Cal-1-transduced PBMCs at day 7 and day 10 was observed, compared against untransduced PBMCs (MOCK control).

Reverse Transcriptase assay (RT assay) (FIG. 13A) was used to measure amount of HIV-1 in 10 μL of culture supernatant, released from infected PBMCs (Suzuki K, et al: Poly A-linked non-isotopic micro titer plate reverse transcriptase assay for sensitive detection of clinical human immunodeficiency virus isolates. J Virol Methods 1995, 55:347-356).

Figure 13A:
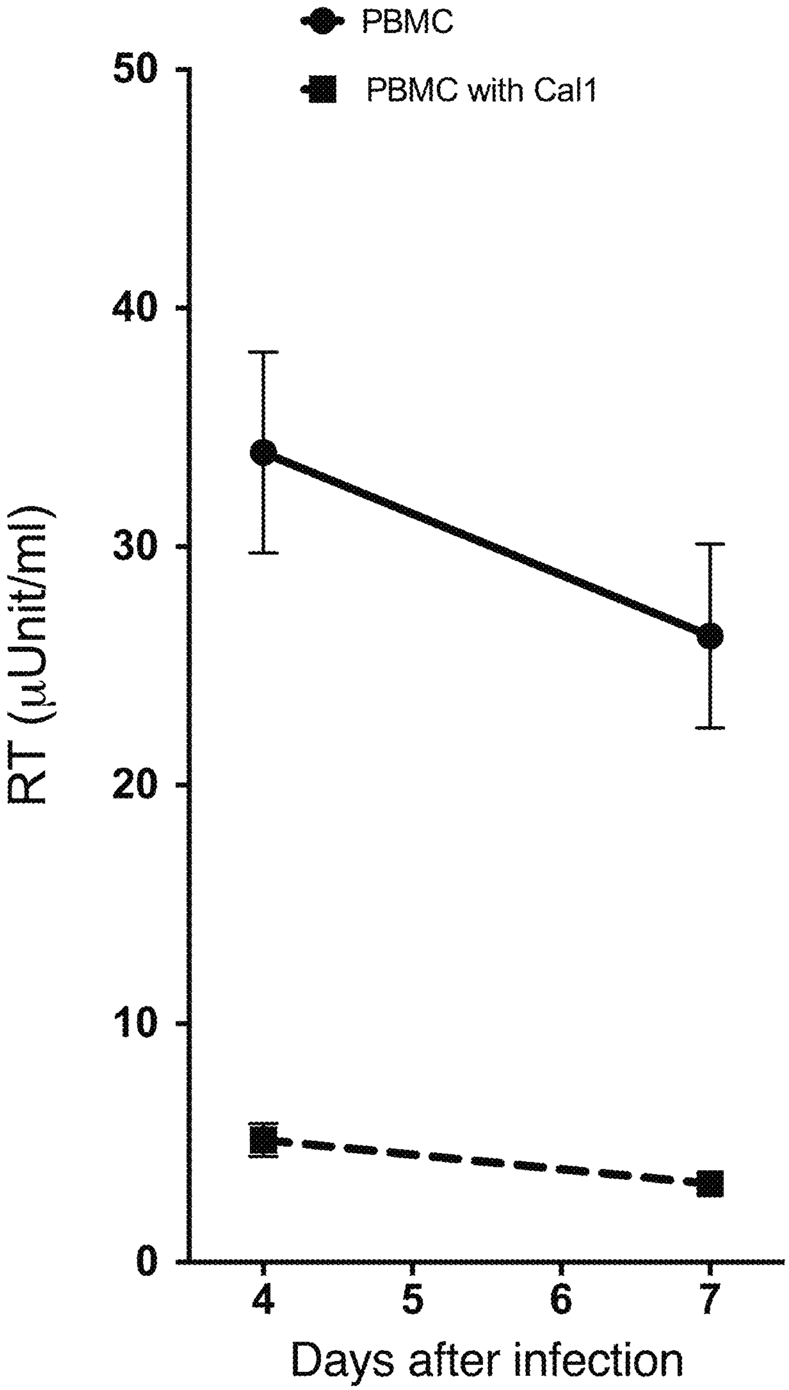
FIG. 13A illustrates a reverse-transcriptase assay data based on PBMCs from a healthy donor. HIV-1 infection experiments were conducted based on PBMCs from a healthy donor. The lenti-Cal-1 transduction was conducted in the same manner as in MOLT4 based experiment above. Over 5 times reduction level of reverse-transcriptase activity was observed in Cal-1 transduced PBMCs after HIV-1 infection on day 4 and day 7, compared with that of untransduced PBMCs.
Figure 13B:
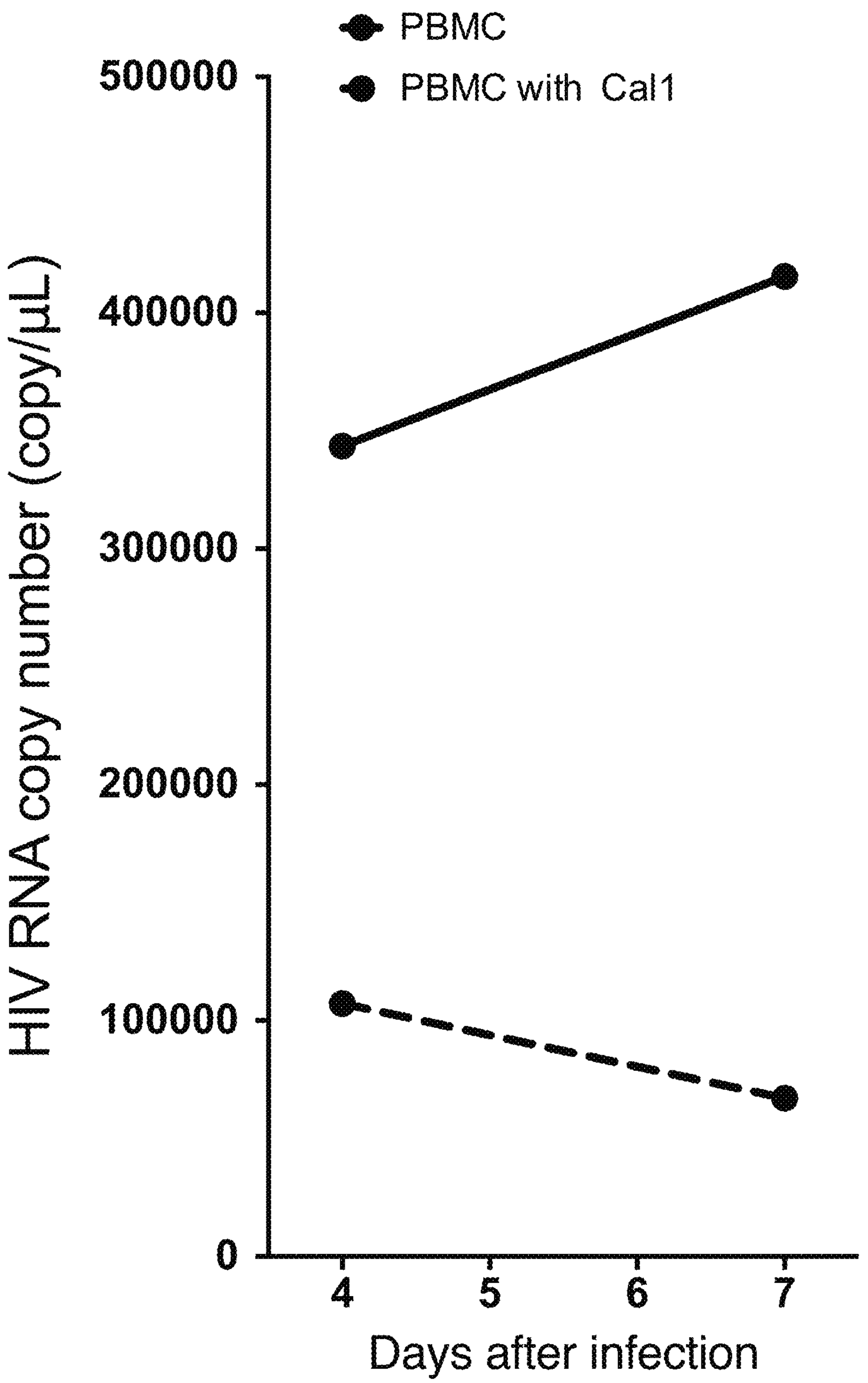
FIG. 13B illustrates a reverse-transcriptase real-time PCR analysis on RNA in cultured supernatants with Method 2. The reverse-transcriptase data in FIG. 13A were confirmed by a TaqMan based reverse-transcriptase real time PCR assay using the extracted RNA from the cultured supernatant. A five-fold reduction in HIV-1 RNA from the cultured supernatant of Cal-1-transduced PBMCs at day 7 and day 10 was observed, compared against untransduced PBMCs (MOCK control).
Figure 14A:
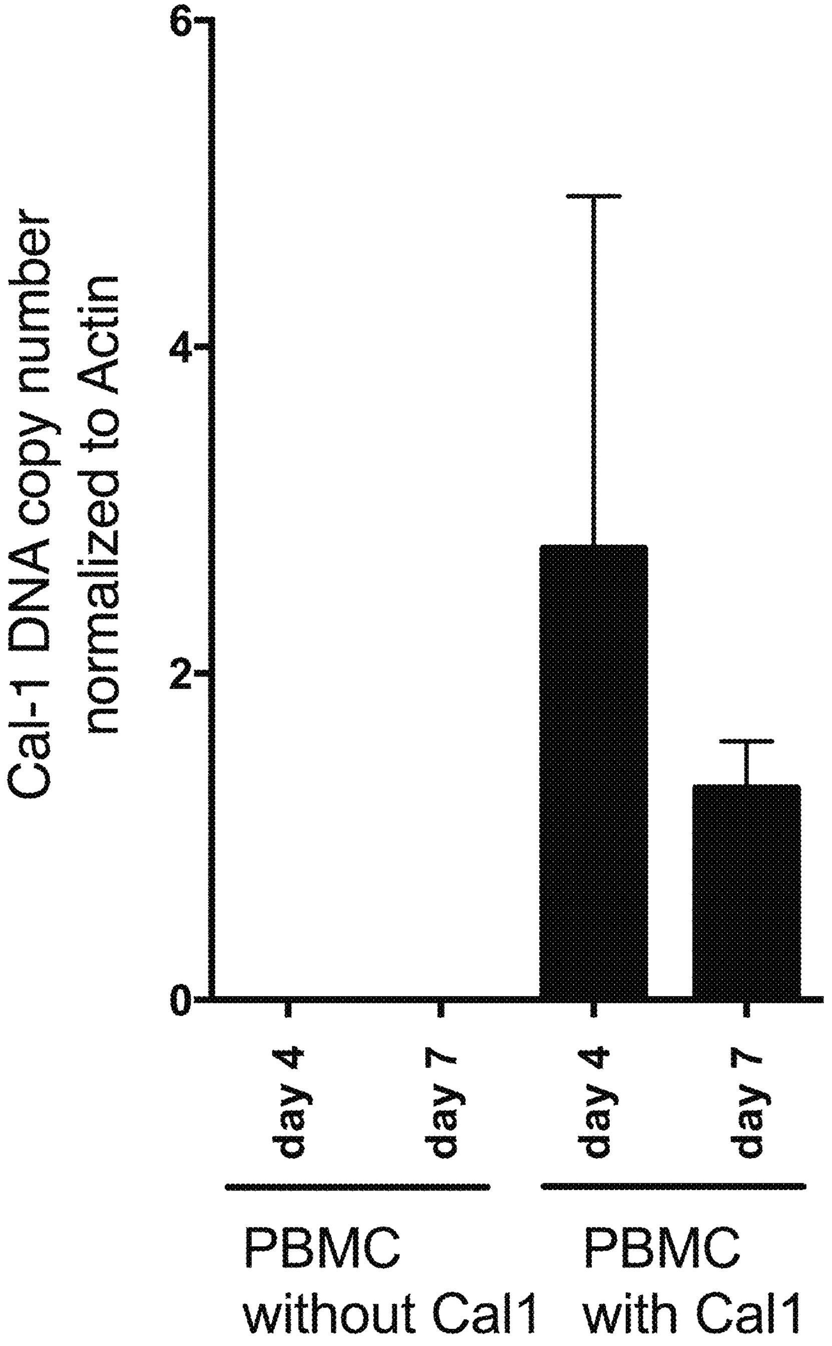
FIG. 14A illustrates the results of Cal-1 DNA detection in PBMCs using two separate tube assays in accordance with a Method 2. Cal-1 integrated DNA was amplified by a TaqMan based DNA PCR method described herein. DNA was extracted from two sets of PBMCs infectious experiments. The data indicates a consistent presence of integrated Cal-1 DNA level (normalized by Actin) in Cal-1 transduced PBMCs from day-4 to 10. Cal-1 DNA was not detected in untransduced PBMCs (MOCK control). Cal-1 copy numbers were normalized with 1000 copies of Action DNA.
Figure 14B:
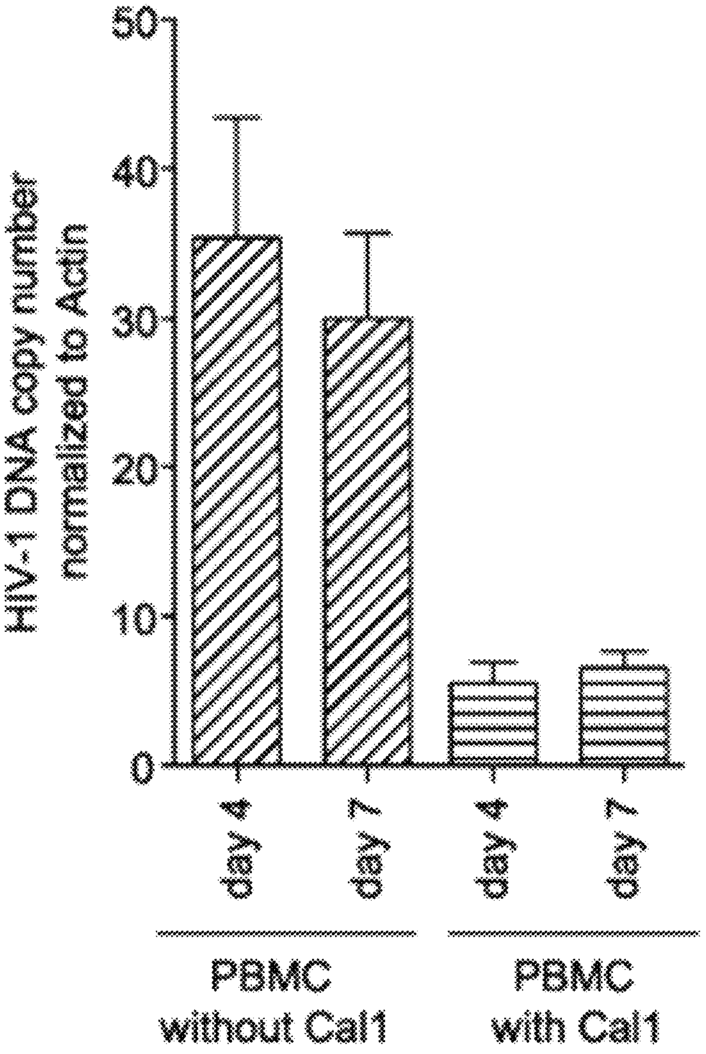
FIG. 14B illustrates the HIV-1 DNA detection in PBMCs. HIV-1 integrated DNA was amplified by a TaqMan based DNA PCR method using two separate tube assays in accordance with Method 2. A five-fold reduction in the integrated levels of HIV-1 DNA was observed in Cal-1 transduced PBMCs compared against untransduced PBMCs on Day-4. The data confirms the protection in PBMCs from HIV-1 infection after transduction of Cal-1 lentiviral vector. HIV-1 copy numbers were normalized with 1000 copies of Action DNA. While PBMCs are difficult to transduce with Cal-1, the data positively supports Cal-1 protection from HIV-1.
Figure 14C:
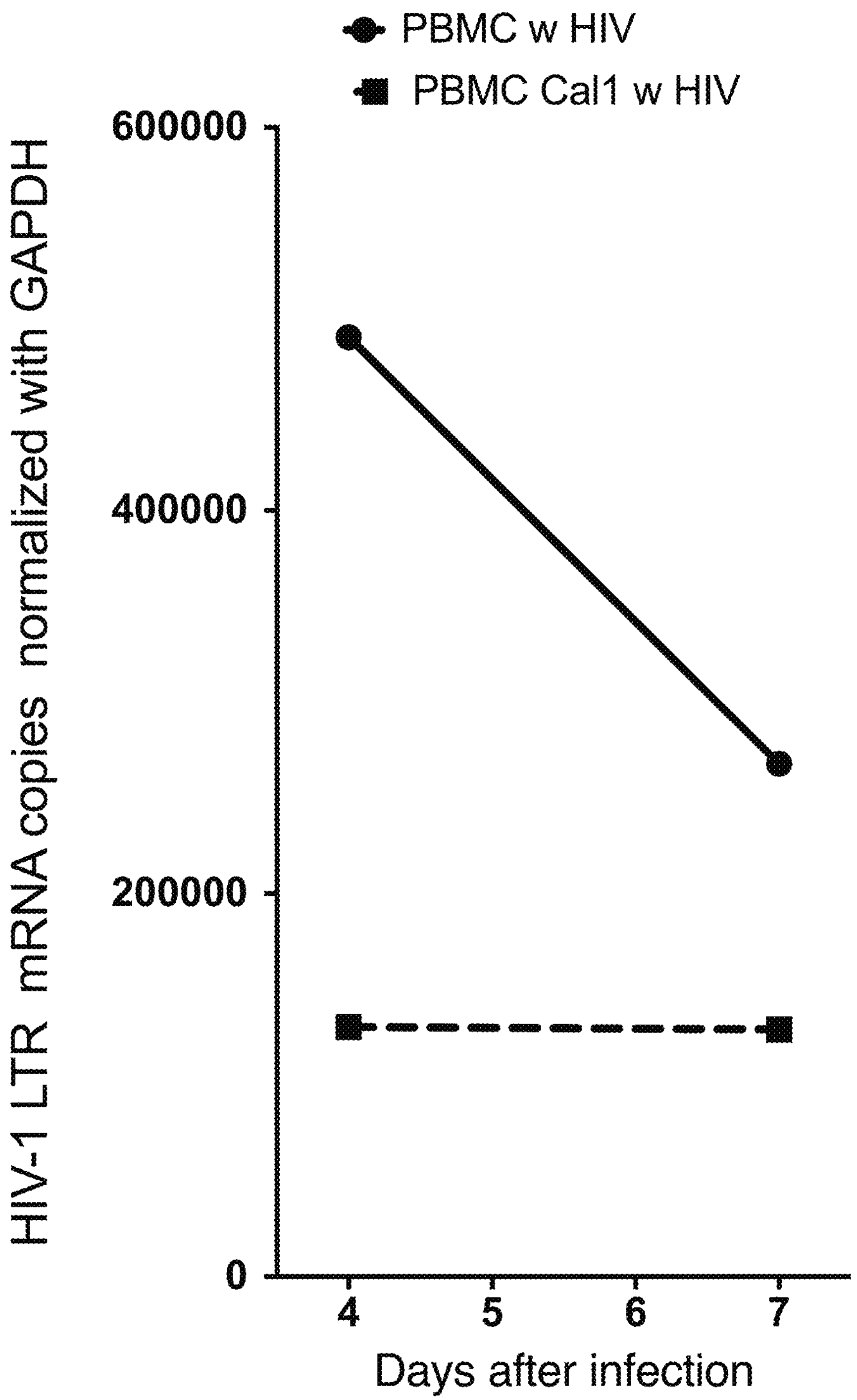
FIG. 14C illustrates the results of an intracellular analysis of HIV-1 RNA in PBMCs, based on 3'LTR assay with Method 2. HIV-1 intracellular mRNA was amplified by a TaqMan based one-step reverse transcriptase real-time PCR method described herein. A greater than 4× reduction of integrated level of HIV-1 viral RNA in the Cal-1 transduced PBMCs was observed in compared with that of untransduced PBMCs on day-4. HIV-1 RNA copy numbers were normalized with 1,000,000 copies of GAPDH mRNA.
Figure 14D:
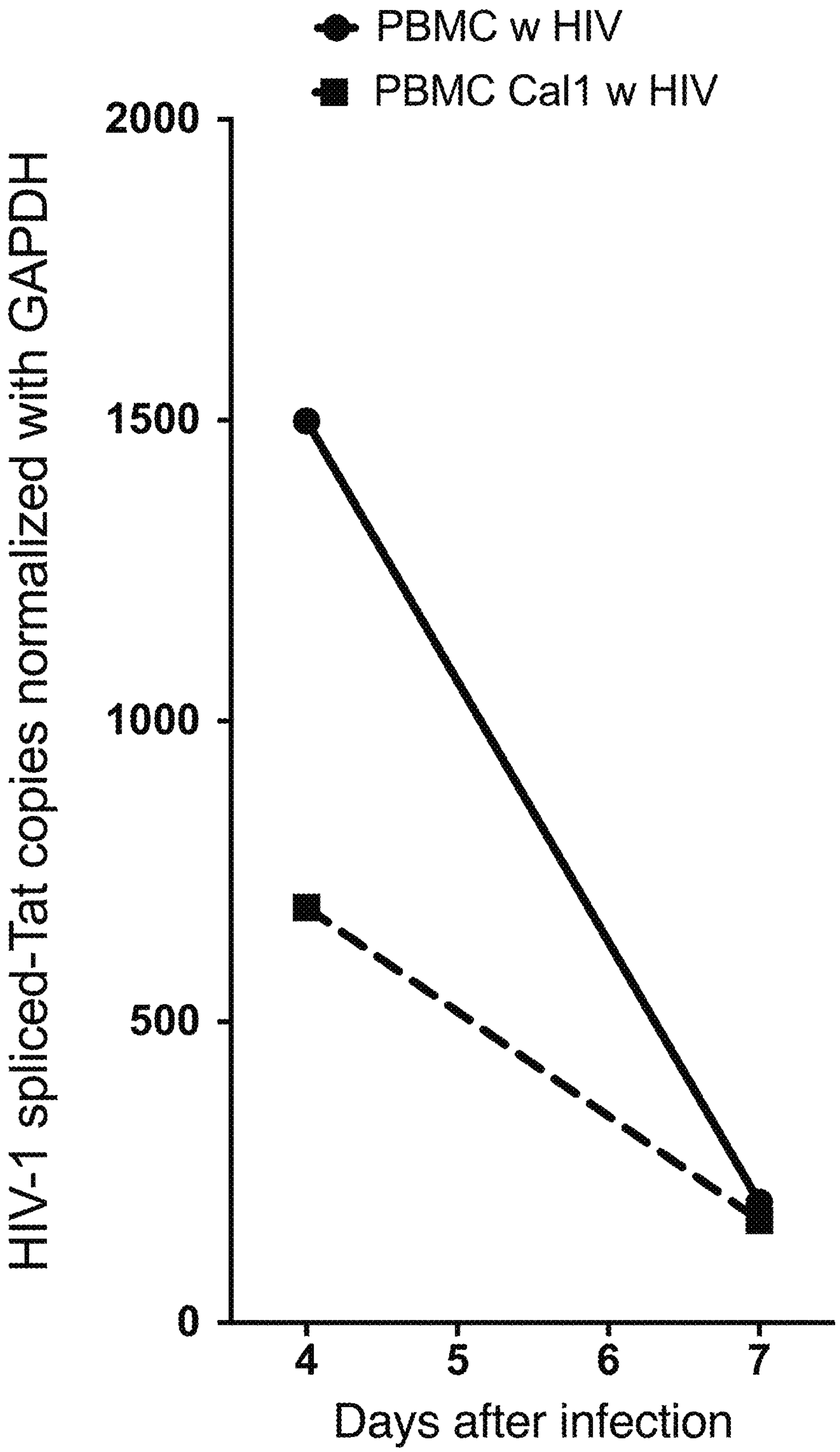
FIG. 14D illustrates the results of an intracellular analysis of HIV-1 RNA in PBMCs, based on spliced-Tat assay. The similar level of massive reduction was observed in the Cal-1 transduced PBMCs based on the spliced-Tat assay. The data in FIGS. 14A and 14B confirm that impact of reduction of integrated HIV-1 DNA levels in the Cal-1 transduced PBMCs. Therefore, a substantial reduction of HIV-1 intracellular mRNA levels was observed in the Cal-1 transduced PBMCs (FIG. 14C and Figure D). HIV-1 RNA copy numbers were normalized with 1,000,000 copies of GAPDH mRNA.

FIG. 13A illustrates a reverse-transcriptase assay data based on PBMCs from a healthy donor. Over 5 times reduction level of reverse-transcriptase activity was observed in Cal-1 transduced PBMCs after HIV-1 infection on day 4 and day 7, compared with that of untransduced PBMCs Additional Embodiments 1. A composition comprising (a) a probe comprising a nucleotide sequence having at least 80% identity to that of SEQ ID NO: 14, the probe conjugated to a reporter moiety; (b) a forward primer comprising a nucleotide sequence having at least 80% identity to that of SEQ ID NO: 2; and (c) a reverse primer comprising a nucleotide sequence having at least 80% identity to that of SEQ ID NO: 6; wherein each of the forward and reverse primers are capable of annealing to a target sequence to amplify the target sequence.

2. The composition of embodiment 1, wherein the reporter moiety is selected from the group consisting of Tex-615, Tye-563, Tye-665, Joe, Cy3, Max, Rox, Tet, Texas Red-X, Tamara, and Yakima Yellow.

3. A composition comprising (a) a probe comprising a nucleotide sequence having at least 80% identity to that of SEQ ID NO: 10; the probe conjugated to a reporter moiety; (b) a forward primer comprising a nucleotide sequence having at least 80% identity to that of SEQ ID NO: 2; and (c) a reverse primer comprising a nucleotide sequence having at least 80% identity to that of SEQ ID NO: 6; wherein each of the forward and reverse primers are capable of annealing to a target sequence to amplify the target sequence.

4. The composition of embodiment 3, wherein the reporter moiety is selected from the group consisting of Tex-615, Tye-563, Tye-665, Joe, Cy3, Max, Rox, Tet, Texas Red-X, Tamara, and Yakima Yellow.

5. A composition comprising (a) a probe comprising a nucleotide sequence having at least 80% identity to that of SEQ ID NO: 8, the probe conjugated to a reporter moiety; (b) a forward primer comprising a nucleotide sequence having at least 80% identity to that of SEQ ID NO: 4; and (c) a reverse primer comprising a nucleotide sequence having at least 80% identity to that of SEQ ID NO: 6; wherein each of the forward and reverse primers are capable of annealing to a target sequence to amplify the target sequence.

6. The composition of embodiment 5, wherein the reporter moiety is selected from the group consisting of Tex-615, Tye-563, Tye-665, Joe, Cy3, Max, Rox, Tet, Texas Red-X, Tamara, and Yakima Yellow.

7. A kit for discriminating between lentiviral nucleic acids and HIV nucleic acids in a sample, the kit comprising the composition of embodiment 1 and the composition of either of embodiments 3 or 5.

8. A method for quantifying a first target sequence comprising contacting a first sample comprising the first target sequence with the probe and primers of the composition of embodiment 1; performing a real-time polymerase chain reaction using the first target sequence as the template; and quantifying an amount of a generated first amplicon.

9. The method of embodiment 8, further comprising quantifying a second target sequence comprising contacting a second sample comprising the second target sequence with the probe and primers of the composition of either embodiment 2 or embodiment 3; and performing real-time polymerase chain reaction using the second target sequence as the template; and quantifying an amount of a generated second amplicon.

10. The method of embodiment 9, wherein the first and second samples are derived from the same source and wherein the quantification of the first and second target sequences takes place in a single reaction chamber.

11. The method of embodiment 9, wherein the first and second samples are derived from the same source and wherein the quantification of the first and second target sequences takes place in separate reaction chambers.

12. The method of embodiment 9, wherein the first target sequence is a lentiviral nucleic acid sequence and wherein the second target sequence is a HIV nucleic acid sequence.

13. The method of embodiment 9, wherein the step of quantifying the amount of the generated first amplicon comprises detecting signals from a first reporter moiety; and wherein the step of quantifying the amount of the generated second amplicon comprises detecting signals from a second reporter moiety, wherein the first and second reporter moieties are different.

14. The method of embodiment 13, further comprising assessing an efficacy of gene transfer from a lentiviral vector by comparing (i) a first ratio of the quantified amount of the generated first amplicon to the quantified amount of the generated second amplicon at a first time point; (ii) to a second ratio of the quantified amount of the generated first amplicon to the quantified amount of the generated second amplicon at a second time point, wherein an increasing ratio of lentiviral nucleic acid to HIV nucleic acid is indicative of therapeutic efficacy.

15. The method of embodiment 8, wherein the first target sequence and the second target sequence are independently DNA or RNA.

16. A method of detecting a lentiviral nucleic acid and/or a HIV nucleic acid in a sample, the method comprising: (a) performing multiplex real-time PCR with a lentiviral nucleic acid template and a HIV nucleic acid template in the sample using: (i) a first forward primer having a nucleotide sequence having at least 80% identity to that of SEQ ID NO: 2, a first reverse primer having a nucleotide sequence having at least 80% identity to that of SEQ ID NO: 6, and a first probe having a nucleotide sequence having at least 80% identity to that of SEQ ID NO:14, the first probe having a first reporter moiety; (ii) a second forward primer having a nucleotide sequence having at least 80% identity to that of SEQ ID NO: 2, a second reverse primer having a nucleotide sequence having at least 80% identity to that of SEQ ID NO: 6, and a second probe having a nucleotide sequence having at least 80% identity to that of SEQ ID NO: 10, the second probe having a second reporter moiety, where the first and second reporter moieties are different; (b) detecting an amplicon generated by (i) the first forward and reverse primers, and (ii) the second forward and reverse primers; and wherein detecting comprises detecting first and second signals from the first and second reporter moieties.

17. A method of detecting a lentiviral nucleic acid and/or a HIV nucleic acid in a sample, the method comprising: (a) performing multiplex real-time PCR with a lentiviral nucleic acid template and a HIV nucleic acid template in the sample using: (i) a first forward primer having a nucleotide sequence having at least 80% identity to that of SEQ ID NO: 2, a first reverse primer having a nucleotide sequence having at least 80% identity to that of SEQ ID NO: 6, and a first probe having a nucleotide sequence having at least 80% identity to that of SEQ ID NO: 14, the first probe having a first reporter moiety; (ii) a second forward primer having a nucleotide sequence having at least 80% identity to that of SEQ ID NO: 4, a second reverse primer having a nucleotide sequence having at least 80% identity to that of SEQ ID NO: 6, and a second probe having a nucleotide sequence having at least 80% identity to that of SEQ ID NO: 8, the second probe having a second reporter moiety, where the first and second reporter moieties are different; (b) detecting an amplicon generated by (i) the first forward and reverse primers, and (ii) the second forward and reverse primers; and wherein detecting comprises detecting first and second signals from the first and second reporter moieties.

18. A method of detecting an amount of a lentiviral nucleic acid in a sample comprising: (a) contacting the sample with a first forward primer and a first reverse primer; (b) contacting the sample with a junction probe specific for a junction site within the 3'LTR of the lentiviral nucleic acid, wherein the junction probe comprises a first portion which is capable of hybridizing to at least a portion of a sequence within the U3 region of the lentiviral nucleic acid 3'LTR and a second portion which is capable of hybridizing to at least a portion of a sequence within the R region of the lentiviral nucleic acid 3'LTR, and wherein the junction probe comprises a first detectable moiety; and detecting signals from the first detectable moiety.

19. The method of embodiment 18, wherein the first portion of the junction probe hybridizes to a nucleotide sequence having at least 80% identity to that of SEQ ID NO: 12.

20. The method of embodiment 18, wherein the second portion of the junction probe hybridizes to a nucleotide sequence having at least 80% identity to that of SEQ ID NO: 13.

21. The method of embodiment 18, wherein the junction probe comprises a nucleotide sequence having at least 80% identity to that of SEQ ID NO: 14.

22. The method of embodiment 18, wherein the junction probe comprises a nucleotide sequence having at least 90% identity to that of SEQ ID NO: 14.

23. The method of embodiment 18, further comprising detecting an amount of an HIV nucleic acid in the sample.

24. The method of embodiment 23, wherein the detection of the amount of the lentiviral nucleic acid and the amount of HIV nucleic acid in the sample takes place in the same reaction tube.

25. The method of embodiment 24, wherein the detection of the amount of the HIV nucleic acid comprises contacting the sample with a second probe specific for a TATA-box sequence within a 3'LTR of an HIV nucleic acid sequence, the second probe conjugated to a second detectable moiety; and detecting signals from the second detectable moiety.

26. The method of embodiment 26, wherein the second probe has a nucleotide sequence having at least 90% identity to that of SEQ ID NO: 10.

27. The method of embodiment 26, wherein the first forward primer is a NuAf primer and the first reverse primer is a LTR-rev primer.

28. The method of embodiment 27, wherein the NuAf primer has the sequence of SEQ ID NO: 2.

29. The method of embodiment 27, wherein the LTR-rev primer has the sequence of SEQ ID NO: 6.

30. The method of embodiment 23, wherein the detection of the amount of the lentiviral nucleic acid and the amount of HIV nucleic acid in the sample takes place in different reaction tubes.

31. The method of embodiment 30, wherein the detection of the amount of the HIV nucleic acid comprises contacting the sample with a second forward primer, a second reverse primer, and a second probe having a nucleotide sequence having at least 90% identity to that of SEQ ID NO: 8, wherein the second probe comprises a second detectable moiety; and detecting signals from the second detectable moiety.

32. The method of embodiment 31, wherein the second forward primer hybridizes to a nucleotide sequence of SEQ ID NO: 3.

33. The method of embodiment 31, wherein the second forward primer comprises a nucleotide sequence having at least 80% identity to that of SEQ ID NO: 4.

34. The method of embodiment 31, wherein the second reverse primer comprises the sequence of SEQ ID NO: 6.

35. A method of detecting a lentiviral nucleic acid in a sample comprising: (a) contacting the sample with a first forward primer and a first reverse primer; (b) contacting the sample with a junction probe specific for a junction site within a 3'LTR of the lentiviral nucleic acid, wherein the 3'LTR of the lentiviral nucleic acid does not comprise a TATA-box sequence, and wherein the junction site spans a portion of the U3 region of the lentiviral nucleic acid 3'LTR and a portion of the R region of the lentiviral nucleic acid 3'LTR, and wherein at least a portion of the junction probe hybridizes to a nucleotide sequence of SEQ ID NO: 13.

36. The method of embodiment 35, further comprising contacting the sample with a second probe specific for a TATA-box sequence within a 3'LTR of an HIV nucleic acid sequence, the second probe having a second detectable moiety, wherein the first and second detectable moieties are different, and detecting signals from the second detectable moiety.

37. The method of embodiment 35, further comprising contacting the sample with a second forward primer, a second reverse primer, and a second probe having a nucleotide sequence having at least 80% identity to that of SEQ ID NO: 8, wherein the second probe comprises a second detectable moiety, wherein the first and second detectable moieties are different; and detecting signals from the second detectable moiety.

38. A method of quantifying an amount of a lentiviral nucleic acid and an amount of an HIV nucleic acid in a sample, the lentiviral nucleic acid and the HIV nucleic acid comprising different 3'LTRs, the method comprising amplifying both the lentiviral nucleic acid and the HIV nucleic acid with a forward primer which hybridizes to a sequence within both the 3'LTR of the lentiviral nucleic acid and the 3'LTR of the HIV nucleic acid, and a reverse primer which hybridizes to a sequence within both the 3'LTR of the lentiviral nucleic acid and the 3'LTR of the HIV nucleic acid, and wherein the amplification of both the lentiviral nucleic acid and the HIV nucleic acid occur in a single reaction tube.

39. The method of embodiment 38, wherein the 3'LTR of the lentiviral nucleic acid comprises at least 50 nucleotides less than the 3'LTR of the HIV nucleic acid.

40. The method of embodiment 39, wherein the 3'LTR of the lentiviral nucleic acid does not comprise a TATA-box sequence.

41. The method of embodiment 39, wherein amplification produces a lentiviral nucleic acid amplicon having a first size and a HIV nucleic acid amplicon having a second size, wherein the amplicon of the lentiviral nucleic acid is smaller than the amplicon of the HIV nucleic acid.

42. The method of embodiment 41, wherein an electrophoretic separation is used to separate the lentiviral nucleic acid amplicon and the HIV nucleic acid amplicon.

43. The method of embodiment 38, wherein the lentiviral nucleic acid 3'LTR comprises a U3 region having a nucleotide sequence of SEQ ID NO: 15.

44. The method of embodiment 38, wherein the HIV nucleic acid 3'LTR comprises a U3 region having a nucleotide sequence of SEQ ID NO: 16.

45. An amplicon obtainable by amplification from a lentiviral nucleic acid-containing sample with a pair of primers, the primers having SEQ ID NO: 2 and SEQ ID NO: 6, the amplicon comprising a 3'LTR that does not comprise a TATA-box sequence.

46. An isolated nucleic acid sequence comprising a nucleotide sequence having at least 90% identity to that of SEQ ID NO: 14.

47. The isolated nucleic acid sequence of embodiment 46, wherein the sequence is conjugated to a detectable moiety.

48. An isolated nucleic acid sequence comprising a nucleotide sequence having at least 90% identity to that of SEQ ID NO: 15.

49. An isolated nucleic acid sequence comprising a nucleotide sequence having at least 70% identity to that of SEQ ID NO: 14 and capable of hybridizing to a fragment of a nucleotide sequence of SEQ ID NO: 15.

50. An isolated nucleic acid sequence having a first portion capable of hybridizing to a nucleotide sequence having at least 70% identity to that of SEQ ID NO:12, and a second portion capable of hybridizing to a nucleotide sequence of SEQ ID NO: 13.

51. The isolated nucleic acid sequence of embodiment 50, wherein the sequence is conjugated to a detectable moiety.

52. An isolated nucleic acid sequence comprising a nucleotide sequence having at least 90% identity to that of SEQ ID NO: 8.

53. The isolated nucleic acid sequence of embodiment 52, wherein the sequence is conjugated to a detectable moiety.

54. An isolated nucleic acid sequence comprising a nucleotide sequence having at least 90% identity to that of SEQ ID NO: 10.

55. The isolated nucleic acid sequence of embodiment 54, wherein the sequence is conjugated to a detectable moiety.

56. A method of treating an HIV positive patient, comprising:

(i) obtaining cells from a patient;

(ii) treating the obtained cells with a Cal-1 lentiviral vector under conditions favoring uptake of Cal-1 into the cells;

(iii) assaying the treated cells for a presence of a genetic modification;

(iv) administering to the patient the treated cells, provided that the cells were positively assayed for the presence of the genetic modification.

57. The method of embodiment 56, wherein the step of assaying for the presence of the genetic modification comprises detecting a junction site within the treated cells.

58. The method of embodiment 57, wherein the detection of the junction site comprises contacting the sample with a junction probe, the junction probe comprising a nucleic acid sequence having at least 90% identity to that of SEQ ID NO: 14.

59. The method of embodiment 56, wherein the detection of the genetic modification is performed at a DNA or RNA level.

60. A method for determining therapeutic efficacy of an HIV-based recombinant vector in a patient, comprising:

(i) obtaining cells from the patient;

(ii) treating the obtained cells with a Cal-1 lentiviral vector under conditions favoring uptake of Cal-1 into the obtained cells;

(iii) assaying for levels of a wild-type HIV nucleic acid present in the obtained cells at a first time point;

(iv) assaying for levels of the wild-type HIV nucleic acid present in the obtained cells at a second time point, (v) assaying for levels of a Cal-1 nucleic acid present in the obtained cells at a first time point;

(vi) assaying for levels of the Cal-1 nucleic acid present in the obtained cells at a second time point, wherein the assaying of the levels of the Cal-1 nucleic acid and the wild-type HIV nucleic acid is performed as in any one of embodiments 16 and 17; and wherein lower levels of the wild-type HIV nucleic acid and higher levels of the Cal-1 nucleic acid at a second time point is indicative of therapeutic efficacy of Cal-1.

61. The method of embodiment 6, wherein steps (iii) through (vi) are repeated at additional time points.

62. A method of detecting an amount of a lentiviral RNA in a sample comprising: (a) converting the lentiviral RNA to cDNA; (b) contacting the sample with a first forward primer and a first reverse primer; (c) contacting the sample with a junction probe specific for a junction site within the 3'LTR of the lentiviral nucleic acid, wherein the junction probe comprises a first portion which is capable of hybridizing to at least a portion of a sequence within the U3 region of the lentiviral nucleic acid 3'LTR and a second portion which is capable of hybridizing to at least a portion of a sequence within the R region of the lentiviral nucleic acid 3'LTR, and wherein the junction probe comprises a first detectable moiety; and detecting signals from the first detectable moiety.

63. The method of embodiment 61, further comprising detecting an amount of a HIV nucleic acid in the same, wherein the HIV nucleic acid is DNA or RNA.

64. A method of treating an HIV positive patient, comprising: (i) treating cells obtained from the HIV positive patient with a Cal-1 lentiviral vector under conditions favoring uptake of Cal-1 into the cells; (ii) assaying the treated cells for a presence of a genetic modification, wherein the step of assaying for the presence of the genetic modification comprises detecting a junction site, wherein the detection of the junction site comprises contacting the treated cells with a junction probe, the junction probe comprising a nucleic acid sequence having at least 90% identity to that of SEQ ID NO: 14; (iii) administering the treated cells to the patient, provided that the treated cells were positively assayed for the presence of the genetic modification.

65. The method of embodiment 64, wherein the detection of the genetic modification is performed using DNA or RNA extracted from the treated cells.

66. The method of embodiment 64, wherein the Cal-1 lentiviral vector comprises a short hairpin RNA against CCR5 and a C46 fusion inhibitor.

67. A method for determining therapeutic efficacy of an HIV-based recombinant vector in a patient, comprising: (i) treating cells derived from the patient with a Cal-1 lentiviral vector under conditions favoring uptake of Cal-1; (ii) administering the treated cells to the patient; (iii) assaying for levels of a wild-type HIV nucleic acid and a Cal-1 nucleic acid present in DNA derived from cells obtained from the patient at a first time point; and (iv) assaying for levels of the wild-type HIV nucleic acid and the Cal-1 nucleic acid present in DNA derived from cells obtained from the patient at a second time point; wherein the assaying of the levels of the Cal-1 nucleic acid and the wild-type HIV nucleic acid at the first and second time points is achieved by (a) performing multiplex real-time PCR using: (i) a first forward primer having a nucleotide sequence having at least 80% identity to that of SEQ ID NO: 2, a first reverse primer having a nucleotide sequence having at least 80% identity to that of SEQ ID NO: 6, and a first probe having a nucleotide sequence having at least 80% identity to that of SEQ ID NO:14, the first probe having a first reporter moiety; (ii) a second forward primer having a nucleotide sequence having at least 80% identity to that of SEQ ID NO: 2, a second reverse primer having a nucleotide sequence having at least 80% identity to that of SEQ ID NO: 6, and a second probe having a nucleotide sequence having at least 80% identity to that of SEQ ID NO: 10, the second probe having a second reporter moiety, where the first and second reporter moieties are different; and (b) quantifying the levels of the Cal-1 nucleic acid generated by the first forward and reverse primers by detecting signals from the first reporter moiety, and quantifying the levels of the wild-type HIV nucleic acid generated by the second forward and reverse primers by detecting signals from the second reporter moiety; and wherein lower levels of the wild-type HIV nucleic acid and higher levels of the Cal-1 nucleic acid at the second time point as compared with the first time point is indicative of therapeutic efficacy of Cal-1.

67. The method of embodiment 67, wherein steps (iii) through (iii) are repeated at additional time points.

68. The method of embodiment 67, wherein the Cal-1 lentiviral vector comprises a short hairpin RNA against CCR5 and a C46 fusion inhibitor.

69. The method of embodiment 67, wherein the first probe has a nucleotide sequence having at least 90% identity to that of SEQ ID NO:14.

70. A method of treating an HIV positive patient, comprising:

(i) transducing cells obtained from the HIV positive patient with a Cal-1 lentiviral vector under conditions favoring uptake of the Cal-1 lentiviral vector into the obtained cells; (ii) assaying the transduced cells for a presence of a genetic modification, wherein the assaying for the presence of the genetic modification comprises detecting a junction site within DNA derived from the transduced cells, wherein the detection of the junction site comprises contacting the DNA derived from the transduced cells with a junction probe, the junction probe comprising a nucleic acid sequence having at least 90% identity to that of SEQ ID NO: 14; and (iii) administering the transduced cells to the patient, provided that the transduced cells were positively assayed for the presence of the genetic modification.

71. The method of embodiment 70, wherein the cells positively assayed for the presence of the genetic modification comprise a Cal-1 lentiviral transgene inserted into DNA or RNA of the transduced cells.

72. The method of embodiment 71, wherein the junction probe is conjugated to a reporter moiety, and wherein detection of the junction probe comprises detecting signals from the reporter moiety.

73. The method of embodiment 70, wherein the reporter moiety is a fluorescent reporter.

74. The method of embodiment 70, wherein the assaying of the transduced cells for the presence of the genetic modification comprises performing real-time polymerase chain reaction on the DNA derived from the transduced cells.

75. The method of embodiment 74, wherein the assaying of the transduced cells for the presence of the genetic modification further comprises contacting the DNA derived from the transduced cells with a forward primer and a reverse primer, wherein each of the forward and reverse primers are capable of annealing to a target sequence to amplify the target sequence.

76. The method of embodiment 75, wherein the forward primer comprises a nucleotide sequence having at least 80% identity to that of SEQ ID NO: 2.

77. The method of embodiment 75, wherein the reverse primer comprises a nucleotide sequence having at least 80% identity to that of SEQ ID NO: 6.

78. The method of embodiment 75, wherein the performing of the real-time polymerase chain reaction on the DNA derived from the transduced cells produces an amplicon corresponding to a Cal-1 lentiviral transgene.

79. The method of embodiment 78, wherein a first portion of the junction probe hybridizes to a nucleic acid sequence within the amplicon comprising a sequence having at least 90% identity to that of SEQ ID NO: 12; and wherein a second portion of the junction probe hybridizes to a nucleic acid sequence within the amplicon comprising a sequence having at least 90% identity to that of SEQ ID NO: 13.

80. The method of embodiment 78, further comprising quantifying an amount of amplicon produced.

81. The method of embodiment 70, wherein the Cal-1 lentiviral vector comprises a short hairpin RNA against CCRS and a C46 fusion inhibitor.

82. The method of embodiment 67, wherein the cells obtained from the patient are stem cells.

All publications mentioned in this specification are herein incorporated by reference in their entirety. It will be appreciated by persons skilled in the art that numerous variations and/or modifications may be made to the disclosure as shown in the specific embodiments without departing from the spirit or scope of the disclosure as broadly described. The present embodiments are, therefore, to be considered in all respects as illustrative and not restrictive.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A composition comprising:

(a) a junction probe conjugated to a first reporter moiety, wherein the junction probe comprises a nucleic acid sequence having a first portion which hybridizes to a nucleotide sequence within a U3 region of a lentiviral nucleic acid 3' LTR and a second portion which hybridizes to a nucleotide sequence within an R region of the lentiviral nucleic acid 3' LTR, wherein the nucleotide sequence within the U3 region of the lentiviral nucleic acid 3' LTR to which the first portion of the junction probe hybridizes comprises SEQ ID NO: 12, and wherein the nucleotide sequence within the R region of the lentiviral nucleic acid 3' LTR to which the second portion of the junction probe hybridizes comprises SEQ ID NO: 13;

(b) a first forward primer comprising a nucleic acid sequence having at least 90% identity to that of SEQ ID NO: 2; and (c) a first reverse primer comprising a nucleic acid sequence having at least 80% identity to that of SEQ ID NO: 6.

2. The composition of claim 1, wherein the junction probe comprises at least 90% sequence identity to SEQ ID NO: 14.

3. The composition of claim 1, wherein the junction probe comprises at least 95% sequence identity to SEQ ID NO: 14.

4. The composition of claim 1, wherein the first reporter moiety is selected from the group consisting of Tex-615, Tye-563, Tye-665, Joe, Cy3, Max, Rox, Tet, Texas Red-X, Tamara, and Yakima Yellow.

5. The composition of claim 1, further comprising a TATA-forward primer, a LTR-reverse primer, and a TAR-probe.

6. The composition of claim 1, wherein the junction probe, the first forward primer, and the first reverse primer are provided in a first container; and wherein the TATA-forward primer, the LTR-reverse primer, and the TAR-probe are provided in a second container.

7. The composition of claim 6, wherein TATA-forward primer comprises a nucleotide sequence having at least 80% identity to that of SEQ ID NO: 4; and wherein the LTR-reverse primer comprises nucleotide sequence having at least 80% identity to that of SEQ ID NO: 6.

8. A method of detecting a lentiviral nucleic acid and/or a HIV nucleic acid in a sample, the method comprising: (a) performing multiplex real-time PCR with a lentiviral nucleic acid template and a HIV nucleic acid template in the sample using: (i) a first forward primer having a nucleotide sequence having at least 80% identity to that of SEQ ID NO: 2, a first reverse primer having a nucleotide sequence having at least 80% identity to that of SEQ ID NO: 6, and a first probe having a nucleotide sequence having at least 80% identity to that of SEQ ID NO: 14, the first probe having a first reporter moiety; (ii) a second forward primer having a nucleotide sequence having at least 80% identity to that of SEQ ID NO: 4, a second reverse primer having a nucleotide sequence having at least 80% identity to that of SEQ ID NO: 6, and a second probe having a nucleotide sequence having at least 80% identity to that of SEQ ID NO: 8, the second probe having a second reporter moiety, where the first and second reporter moieties are different; (b) detecting an amplicon generated by (i) the first forward and reverse primers, and (ii) the second forward and reverse primers; and wherein detecting comprises detecting first and second signals from the first and second reporter moieties.

9. The method of claim 8, wherein the detecting of the lentiviral nucleic acid and/or the HIV nucleic acid take place in separate containers.

* * * * *